(12) United States Patent
Skelton et al.

(10) Patent No.: US 8,437,861 B2
(45) Date of Patent: May 7, 2013

(54) POSTURE STATE REDEFINITION BASED ON POSTURE DATA AND THERAPY ADJUSTMENTS

(75) Inventors: Dennis M. Skelton, Bloomington, MN (US); Jon P. Davis, St. Michael, MN (US)

(73) Assignee: Medtronic, Inc., Minneapolis, MN (US)

( * ) Notice: Subject to any disclaimer, the term of this patent is extended or adjusted under 35 U.S.C. 154(b) by 521 days.

(21) Appl. No.: 12/433,858

(22) Filed: Apr. 30, 2009

(65) Prior Publication Data

US 2010/0010574 A1 Jan. 14, 2010

Related U.S. Application Data

(60) Provisional application No. 61/080,089, filed on Jul. 11, 2008.

(51) Int. Cl.
*A61N 1/00* (2006.01)

(52) U.S. Cl.
USPC .......................................................... 607/62

(58) Field of Classification Search ............... 607/62
See application file for complete search history.

(56) References Cited

U.S. PATENT DOCUMENTS

| | | | |
|---|---|---|---|
| 4,297,685 A | 10/1981 | Brainard, II | |
| 4,365,633 A | 12/1982 | Loughman | |
| 4,543,955 A | 10/1985 | Schroeppel | |
| 4,550,736 A | 11/1985 | Broughton et al. | |
| 4,566,456 A | 1/1986 | Koning et al. | |
| 4,771,780 A | 9/1988 | Sholder | |
| 4,776,345 A | 10/1988 | Cohen et al. | |
| 4,846,180 A | 7/1989 | Buffet | |
| 4,846,195 A | 7/1989 | Alt | |
| 5,031,618 A | 7/1991 | Mullett | |
| 5,040,534 A | 8/1991 | Mann et al. | |

(Continued)

FOREIGN PATENT DOCUMENTS

| | | |
|---|---|---|
| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Christopher D Koharski
*Assistant Examiner* — Philip Edwards
(74) *Attorney, Agent, or Firm* — Shumaker & Sieffert, P.A.

(57) ABSTRACT

The disclosure is directed towards posture-responsive therapy. To avoid interruptions in effective therapy, an implantable medical device may include a posture state module that detects the posture state of the patient and automatically adjusts therapy parameter values according to the detected posture state. A system may include a posture state module that records a current posture of a patient, a user interface that receives a therapy adjustment, a processor that associates a posture that the posture state module recorded when the user interface received the therapy adjustment with the therapy adjustment, determines whether the posture falls within a defined posture state, compares the therapy adjustment to therapy information associated with the defined posture state, and updates the set of posture state definitions based on the determination and comparison.

28 Claims, 32 Drawing Sheets

U.S. PATENT DOCUMENTS

| | | |
|---|---|---|
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,469,861 A | 11/1995 | Piscopo et al. |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,833,713 A | 11/1998 | Moberg |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |

| | | |
|---|---|---|
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 * | 2/2008 | Heruth et al. ........... 607/17 |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 * | 11/2005 | Miesel ........... 607/46 |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 * | 6/2007 | Bourget et al. ........... 607/62 |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 * | 10/2008 | Gerber et al. ........... 607/2 |

| | | |
|---|---|---|
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | Kristofer et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089649 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

IBM and Citizen Watch develop Linux-Based "WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308,1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.

Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.

Goodrich et al., "The Prediction of Pain Using Measures of Sleep Quality," Pain Digest, 8:23-25, 1998.

Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.

Hendelman et al., "Validity of Accelerometry for the Assessment of Moderate Intensity Physical Activity in the Field," Medicine & Science in Sports & Exercise, pp. S442-S449, 2000.

Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.

Husak, "Model of Tilt Sensor Systems, "ICECS 2002, $9^{th}$ IEEE International Conference on Electronics, Circuits and Systems, vol. 1, pp. 227-230, 2002.

Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.

Kassam, "2005 EDP Topic "MK4": Tremor Data-Logger for Parkinson's Disease Patients," http://www.ee.ryerson.ca/~courses/edp2005/MK4.html, 3 pp., 2005.

Kerr et al., "Analysis of the sit-stand-sit movement cycle in normal subjects," Clinical Biomechanics, vol. 12, No. 4, pp. 236-245, 1977.

Kiani et al., "Computerized Analysis of Daily Life Motor Activity for Ambulatory Monitoring," Technology and Health Care 5, pp. 307-318, 1997.

Kitchin et al., "Compensating for the 0 g Offset Drift of the ADXL50 Accelerometer," Analog Devices Application Note AN-380, 2 pp.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.

Lorussi, "Wearable, Redundant Fabric-Based Sensor Arrays for Reconstruction of Body Segment Posture," IEEE Sensors Journal, vol. 4, No. 6, pp. 808-817, Dec. 2004.

Mathie et al., "A Pilot Study of Long-Term Monitoring of Human Movements in the Home Using Accelerometer," Journal of Telemedicine and Telecare10:144-151, Jun. 2007.

Mathie et al., "Determining Activity Using a Triaxial Accelerometer," Proceedings of the Second Joint EMBS/BMES Conference, Houston, TX, pp. 2481-2482, Oct. 23-26, 2002.

Mattmann et al., "Recognizing Upper Body Postures Using Textile Strain Sensors," Proceedings Eleventh IEEE International Symposium on Wearable Computers, ISWC, pp. 29-36, 2007.

Mendez et al., "Interactions Between Sleep and Epilepsy," Journal of Clinical Neurophysiology, American Clinical Neurophysiology Society, 18(2), pp. 106-127, 2001.

Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.

Slyper et al., "Action Capture with Accelerometers," Eurographics/ACM SIGGRAPH Symposium on Computer Animation, Carnegie Mellon University, 7 pp. 2008.

Smith et al., "How do sleep disturbance and chronic pain inter-relate? Insights from the longitudinal and cognitive-behavioral clinical trials literature," Sleep Medicine Reviews, YSMRV 286, pp. 1-14, 2003.

Smith et al., "Presleep cognitions in Patients with Insomnia Secondary to Chronic Pain," Journal of Behavioral Medicine, vol. 24, No. 1, pp. 93-114, 2001.

Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.

Trolier-Mckinstry et al., "Thin Film Piezoelectrics for MEMS," Journal of Electroceramics, v. 12, No. 1-2, pp. 7-17, Jan./Mar. 2004.

Tuck, "Implementing Auto-Zero Calibration Technique for Accelerometers," Freescale Semiconductor Application Note AN3447, 5 pp. Mar. 2007.

Tuisku, "Motor Activity Measured by Actometry in Neuropsychiatric Disorders," Department of Psychiatry, University of Helsinki, Helsinki, Finland, 115 pp. 2002.

Vega-Gonzalez, "Upper Limb Activity Monitoring," Arch Phys Med Rehabil, vol. 86, pp. 541-548, Mar. 2005.

Velten et al., "A New Three-Axis Accelerometer," Sensor '99-$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.

U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

* cited by examiner

POSTURE STATE REDEFINITION BASED ON POSTURE DATA AND THERAPY ADJUSTMENTS

This application claims the benefit of U.S. Provisional Application Ser. No. 61/080,089, to Skelton et al., filed Jul. 11, 2008, and entitled "POSTURE STATE MANAGEMENT FOR POSTURE-RESPONSIVE THERAPY," which is incorporated herein by reference in its entirety.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure is directed to posture state-responsive therapy. The disclosure contemplates a variety of features for managing association of therapy parameter values with different posture states to support posture state-responsive therapy. To deliver posture state-responsive therapy, an IMD detects a posture state of the patient, and adjusts therapy delivered to the patient according to the detected posture state.

A posture state may refer to a patient posture or a combination of patient posture and activity. As a patient's posture state changes, therapy can be adjusted to accommodate differences in symptoms or patient response to therapy. Adjustments to therapy may include selection of different therapy programs and/or adjustments to one or more therapy parameter values associated with one or more therapy programs.

A programmer for an implantable medical device may provide a variety of features to support association of therapy parameter values with different posture states. As an example, a patient may indicate a value for a previously undefined therapy parameter value for a defined posture state while the patient is in the posture state or transitioning to the posture state. The indicated value may be defined for the posture state. As another example, a user may link multiple posture states and select a set of therapy parameter values for delivery of therapy for each of the linked posture states. In this manner, it may not be necessary to specify separate sets of therapy parameter values for each individual posture state.

Also, a user may define therapy parameter values for delivery of therapy to a patient and associate the therapy parameter values with multiple posture states based on user input, e.g., simultaneously. As another example, upon storing a set of pre-established posture state definitions for delivery of posture state-responsive therapy, a device may permit a patient to submit a request via a patient programmer to update the set of pre-established posture state definitions.

As another feature, upon delivering therapy to a patient according to a set of therapy parameter values while the patient occupies a first posture state, one or more of the therapy parameter values may be associated with a second posture state different from the first posture state based on patient input. This feature may permit association of therapy parameter values with the second posture state without requiring the patient to actually occupy that posture state.

As an additional feature, a posture state definition may be modified based on user therapy adjustments and/or posture state information. In some cases, the posture state may be expanded and split. In other cases, the posture state may be reduced in size based on posture state information. Hence, using one or more of the features described in this disclosure, therapy parameter values may be flexibly, conveniently, and efficiently specified for various posture states, including predetermined posture states and patient-created posture states.

In one example, the disclosure provides a method comprising defining a plurality of posture states for a patient, defining therapy parameter values for at least some of the posture states, receiving patient input indicating a value for a previously undefined therapy parameter value for one of the defined posture states while the patient is in the respective posture state or transitioning to the respective posture state, and defining the previously undefined therapy parameter value for the respective posture state based on the patient input.

In another example, the disclosure provides a system comprising a memory that stores a definition of a plurality of posture states for a patient and a definition of therapy parameter values for at least some of the posture states, an external programmer comprising a user interface that receives patient input indicating a value for a previously undefined therapy parameter value for one of the defined posture states while the patient is in the respective posture state or transitioning to the respective posture state, a processor that defines the previously undefined therapy parameter value for the respective posture state based on the patient input, and an implantable medical device that detects the posture states, and delivers therapy to the patient input using the therapy parameter values defined for the detected posture states.

In another example, the disclosure provides a method comprising linking a plurality of posture states of a patient, selecting a set of therapy parameter values for delivery of therapy to the patient by an implantable medical device for each of the linked posture states; and defining the therapy to be delivered to the patient by the implantable medical device for each of the linked posture states based on the selection.

In another example, the disclosure provides an external programmer for an implantable medical device, the programmer comprising a user interface that receives user input linking a plurality of posture states of a patient, and selecting a set of therapy parameter values for delivery of therapy to the patient by the implantable medical device for each of a linked posture states, and a processor that defines the therapy to be delivered to the patient by the implantable medical device for each of the linked posture states based on the selection.

In another example, the disclosure provides a system comprising a user interface that receives user input linking a plurality of posture states of a patient, and selecting a set of therapy parameter values for delivery of therapy to the patient for each of a linked posture states, a processor that defines the therapy to be delivered to the patient for each of the linked posture states based on the selection, and an implantable medical device that delivers the therapy to the patient for each of the linked posture states based on the selection.

In another example, the disclosure provides a method comprising defining therapy parameter values for delivery of therapy to a patient, associating one or more of the therapy parameter values with a plurality of posture states based on user input, and automatically defining therapy parameter values for delivery of therapy to a patient when the patient occupies the posture states based on the association.

In another example, the disclosure provides an external programmer for an implantable medical device, the programmer comprising a user interface that receives user input defining therapy parameter values for delivery of therapy to a patient, and user input associating one or more of the therapy parameter values with a plurality of posture states based on user input, and a processor that automatically defining therapy parameter values for delivery of therapy to a patient when the patient occupies the posture states based on the association.

In another example, the disclosure provides a system comprising an external programmer comprising a user interface that receives user input defining therapy parameter values for delivery of therapy to a patient, and user input associating one or more of the therapy parameter values with a plurality of posture states based on user input, a processor that automatically defining therapy parameter values for delivery of therapy to a patient when the patient occupies the posture states based on the association, and an implantable medical device that delivers the therapy to the patient in response to detection of the posture states.

In another example, the disclosure provides a method comprising storing a set of pre-established posture state definitions for delivery of posture state-responsive therapy to a patient, receiving a request from a patient via a patient programmer to update the set of pre-established posture state definitions, and updating the set of pre-established posture state definitions in response to the request.

In another example, the disclosure provides an external programmer comprising a user interface that receives a request from a user to update a set of pre-established posture state definitions for delivery of posture responsive therapy to a patient, and a processor that updates the set of pre-established posture state definitions in response to the request.

In another example, the disclosure provides a system comprising a memory that stores a set of pre-established posture state definitions for delivery of posture responsive therapy to a patient, an external programmer comprising a user interface that receives a request from a user to update the set of pre-established posture state definitions, and a processor that updates the set of pre-established posture state definitions in response to the request.

In another example, the disclosure provides a method comprising receiving a request from a user to add a new posture state to a set of posture state definitions for delivery of posture responsive therapy to a patient, receiving a graphical representation of a desired location of the new posture state from the user, and defining the new posture state based on the desired location in response to the request.

In another example, the disclosure provides a method comprising delivering therapy to a patient according to a set of therapy parameter values while the patient occupies a first posture state, associating one or more of the therapy parameter values with a second posture state different from the first posture state based on patient input, and automatically defining therapy for delivery to the patient when the patient occupies the second posture state based on the associated therapy parameter values.

In another example, the disclosure provides a system comprising an implantable medical device that delivers therapy to a patient according to a set of therapy parameter values while the patient occupies a first posture state, a user interface that receives patient input associating one or more of the therapy parameter values with a second posture state different from the first posture state, and a processor that automatically defines therapy for delivery to the patient when the patient occupies the second posture state based on the associated therapy parameter values.

In another example, the disclosure provides an external programmer for an implantable medical device, the programmer comprising a user interface that receives patient input associating one or more therapy parameter values of therapy delivered from the implantable medical device to a patient when the patient occupies a first posture state with a second posture state different from the first posture state, and a processor that automatically defines therapy for delivery from the implantable medical device to the patient when the patient occupies the second posture state based on the associated therapy parameter values.

In another example, the disclosure provides a method comprising recording a plurality of postures of a patient over a period of time, identifying a set of the plurality of postures that fall within a posture state, and redefining a boundary of the posture state based on where the postures fall within the posture state.

In another example, the disclosure provides a system comprising a memory that stores posture state definitions, a posture state module that records a plurality of postures of a patient over a period of time, and a processor that identifies a set of the plurality of postures that fall within a posture state, and redefines a boundary of the posture state based on where the postures fall within the posture state.

In another example, the disclosure provides a method comprising recording a therapy adjustment and a posture of a patient corresponding to the therapy adjustment, determining whether the posture falls within a defined posture state, comparing the therapy adjustment to therapy information associated with the defined posture state, and updating a set of posture state definitions based on the determination and comparison.

In another example, the disclosure provides a system comprising a posture state module that records a current posture of a patient, a user interface that receives a therapy adjustment, a processor that associates a posture that the posture state module recorded when the user interface received the therapy adjustment with the therapy adjustment, determines whether the posture falls within a defined posture state, compares the therapy adjustment to therapy information associated with the defined posture state, and updates the set of posture state definitions based on the determination and comparison.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1A:
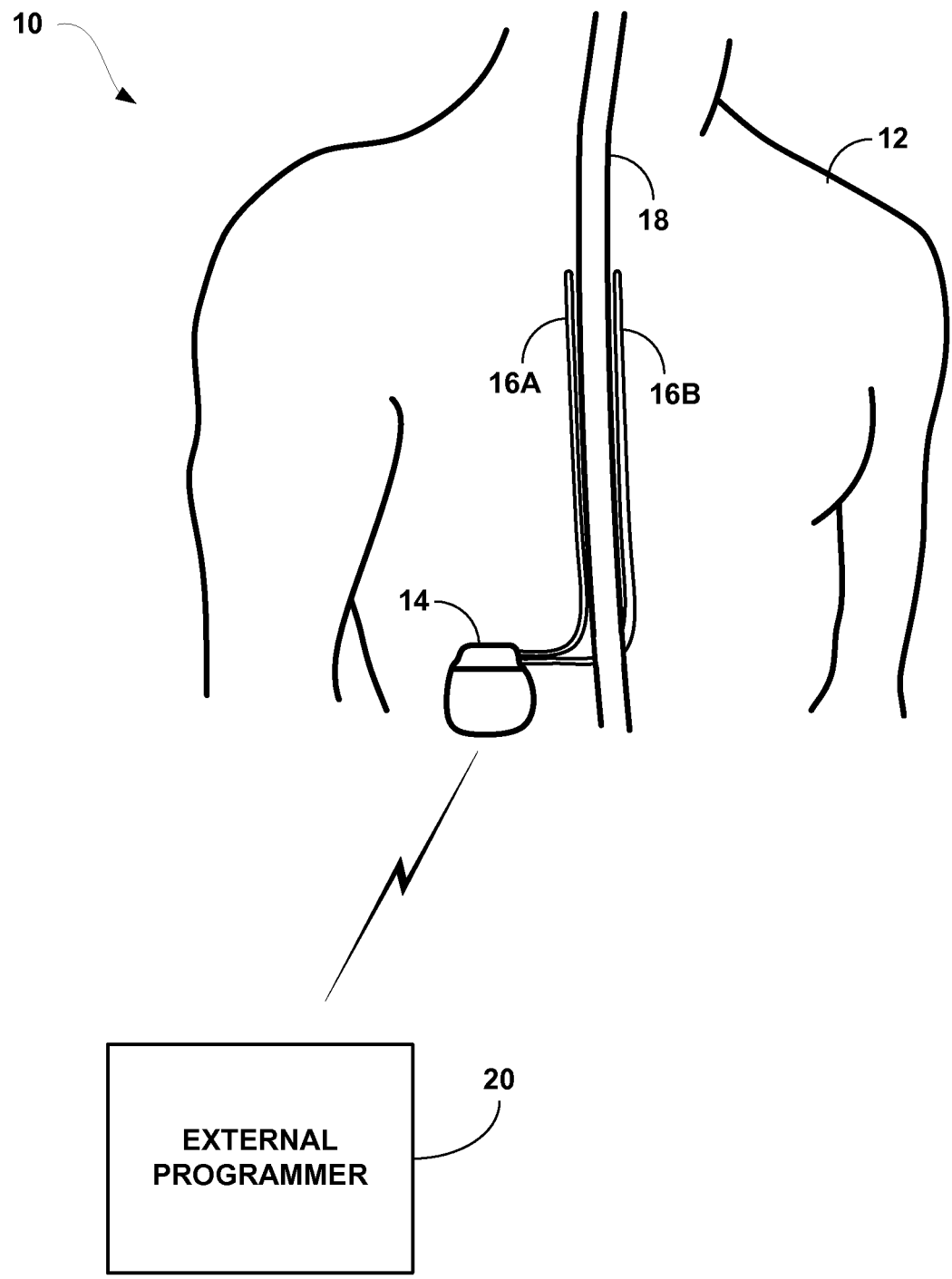
FIG. 1A is a conceptual diagram illustrating an implantable stimulation system including two implantable stimulation leads.

In some medical devices that deliver electrical stimulation therapy, therapeutic efficacy may change as the patient changes posture states. In general, a posture state may refer to a posture or a combination of posture and activity. Efficacy may refer, in general, to a combination of complete or partial alleviation of symptoms alone, or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. Also, posture state changes may present changes in symptoms or symptom levels, e.g., pain level. For example, for a given patient, sitting may be more painful on the patient's back than standing regardless of any migration or compression of the therapy delivery elements. To maintain therapeutic efficacy, it may be desirable to adjust therapy parameters based on different postures and/or activities engaged by the patient to maintain effective stimulation therapy. Therapy parameters may be adjusted directly or by selecting different programs or groups of programs defining different sets of therapy parameters.

A change in efficacy due to changes in posture state may require the patient to continually manage therapy by manually adjusting certain therapy parameters, such as amplitude, pulse rate, or pulse width, or selecting different therapy programs to achieve more efficacious therapy throughout many different posture states. In some cases, a medical device may employ a posture state detector that detects the patient posture state. The medical device may adjust therapy parameters in response to different posture states as indicated by the posture state detector.

For posture state-responsive therapy, therapy adjustments in response to different posture states may be fully automatic or semi-automatic in the sense that a user may provide approval of proposed changes. The disclosure contemplates a variety of techniques for managing association of therapy parameter values with different posture states.

As will be described, such techniques may include permitting a patient to define one or more therapy parameter values associated with different posture states and/or permitting a patient to create new posture states and specify associated therapy parameter values for such posture states. In addition, such techniques may permit a user to link multiple posture states together such that one set of therapy parameter values is associated with the set of linked posture states, associate therapy parameter values with multiple posture states simultaneously, and/or associate therapy parameter values with a posture state without requiring the patient to actually occupy that posture state. As another example, posture state definitions may be automatically updated, e.g., based on recorded posture vector and therapy adjustment data. Hence, therapy parameter values may be flexibly, conveniently, and efficiently specified for various posture states, including predetermined posture states and patient-created posture states.

FIG. 1A is a schematic diagram illustrating an implantable stimulation system 10 including a pair of implantable electrode arrays in the form of stimulation leads 1 6A and 16B. Although the techniques described in this disclosure may be generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As shown in FIG. 1A, system 10 includes an IMD 14 and external programmer 20 shown in conjunction with a patient 12. In the example of FIG. 1A, IMD 14 is an implantable electrical stimulator configured for SCS, e.g., for relief of chronic pain or other symptoms. Again, although FIG. 1A shows an implantable medical device, other embodiments may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as SCS to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, or gastroparesis. In this manner, system 10 may be configured to provide therapy taking the form of deep brain stimulation (DBS), pelvic floor stimulation, gastric stimulation, or any other stimulation therapy. In addition, patient 12 is ordinarily a human patient.

Each of leads 16 may include electrodes (not shown in FIG. 1), and the parameters for a program that controls delivery of stimulation therapy by IMD 12 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 12 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that is used on a temporary basis to evaluate potential efficacy to aid in consideration of chronic implantation for a patient. In additional embodiments, IMD 14 may be a leadless stimulator with one or more arrays of electrodes arranged on a housing of the stimulator rather than leads that extend from the housing.

The stimulation may be delivered via selected combinations of electrodes carried by one or both of leads 16. The target tissue may be any tissue affected by electrical stimulation energy, such as electrical stimulation pulses or waveforms. Such tissue includes nerves, smooth muscle, and skeletal muscle. In the example illustrated by FIG. 1A, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry one or more arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In exemplary embodiments, IMD 14 delivers stimulation therapy according to one or more programs. A program defines one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs in a group. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. For example, stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may need to be decreased to avoid causing patient 12 additional pain or unusual sensations, which may be considered undesirable side effects that undermine overall efficacy.

Many other examples of reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically adjust stimulation according to the detected posture state. For example, a posture state module may include a posture state sensor such as an accelerometer that detects when patient 12 lies down, stands up, or otherwise changes posture.

In response to a posture state indication by the posture state module, IMD 14 may change program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. Additionally, in response to a posture state change, IMD 14 may communicate with external programmer 20 to provide a notification to a user, such a clinician, that patient 12 has potentially experienced a fall.

A user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

A user interface of external programmer 20 may indicate to the user the posture state in which the patient 12 currently resides. This patient posture state may be a static posture that does not take into account activity level, an activity level that does not take into account posture, or some combination of the posture and activity level that describes the physical position and movement of patient 12. As an example, posture may be characterized as one of the following postures: standing, sitting, lying down on back, lying down on front, lying down on left side, lying down on right side. Activity level may be characterized as one of high, medium and low, or be characterized in terms of a numeric scale, e.g., 1-10 or 1-12. In other embodiments, other gradations, e.g., high, medium high, medium, medium low, and low, or other numerical scales may be used to characterize activity level.

A posture state may indicate a combination of one of the above postures with one of the above activity levels. For some postures, such as lying down postures, the posture state may not need to consider activity level, as the patient may be less likely to undertake any significant activity in such postures. In other cases, all posture states may take into account posture and activity level, even if there is minimal activity in a particular posture. Posture state may be determined based on posture information and/or activity level information generated by a posture state module, which may include one or more accelerometers or other posture or activity level sensors.

A patient posture state may be represented by a posture state indication presented by the user interface of programmer 20 as a visible, audible, or tactile indication. When presented as a visible indication, the posture state indication may be, for example, a graphical representation, a symbolic icon, a textual representation, such as word or number, an arrow, or any other type of indication. The visible indication may be presented via a display, such as an a liquid crystal display (LCD), dot matrix display, organic light-emitting diode (OLED) display, touch screen, or the like. In other cases, the visible indication may be provided in a translucent area that is selectively backlit to indicate a posture. An audible indication may be produced by programmer 20 as spoken words stating a posture state, or different audible tones, different numbers of tones, or other audible information generated by the programmer to indicate posture state. A tactile indication of posture state may be produced by programmer 20, for example, in the form of different numbers of vibratory pulses delivered in sequence or vibratory pulses of different lengths, amplitudes, or frequencies.

Programmer 20 may present multiple indications representative of different patient posture states. IMD 14 may communicate a patient posture state according to a posture state parameter value sensed by a posture state module to external programmer 20, e.g., by wireless telemetry. For example, IMD 14 may transmit a posture state indication to programmer 20 on a periodic, intermittent or continuous basis or in response to a posture state change. Alternatively, programmer 20 may request a posture state indication from IMD 14 on a periodic, intermittent or continuous basis. External programmer 20 then may select and present the associated posture state indication.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by IMD 14, whereas a patient programmer may support adjustment and selection of such programs by a patient during ordinary use.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

At the distal tips of leads 16 are one or more electrodes (not shown) that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Figure 1B:
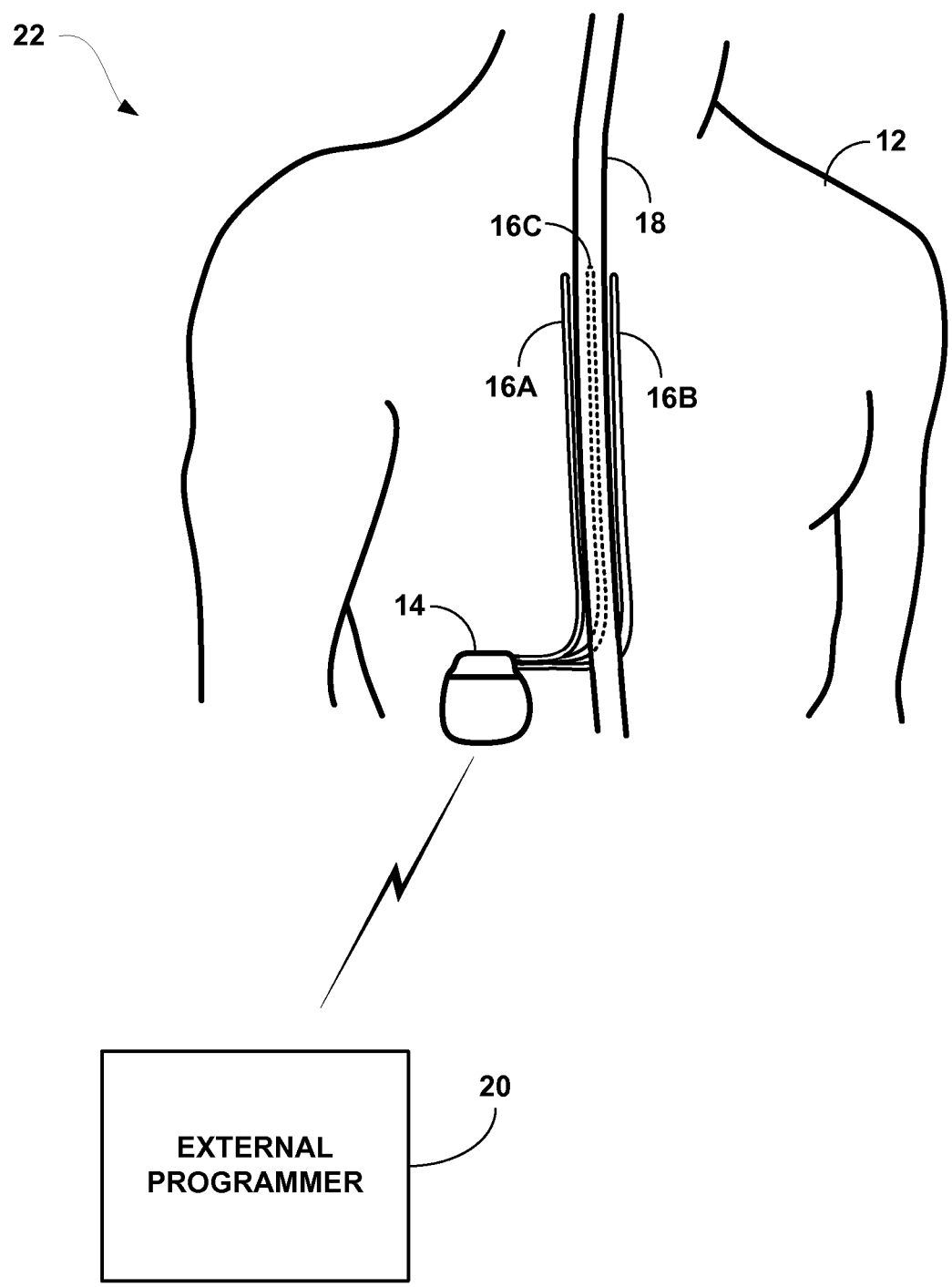
FIG. 1B is a conceptual diagram illustrating an implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. External programmer 20 may be initially told the number and configuration of leads 16 in order to appropriately program stimulation therapy.

For example, leads 16A and 16B could include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
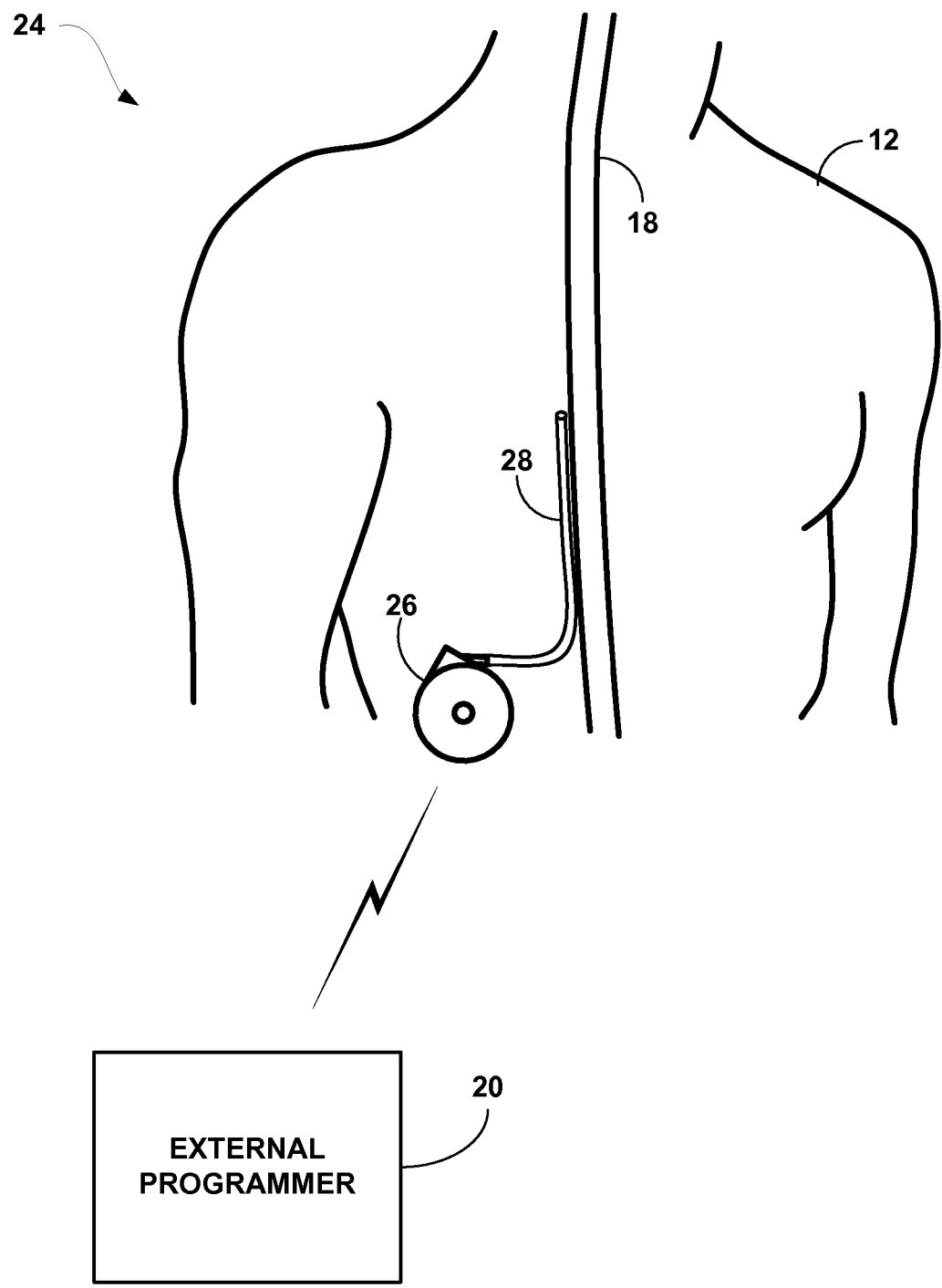
FIG. 1C is a conceptual diagram illustrating an implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of drug stimulation therapy instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some embodiments, IMD 26 may be an external device which includes a percutaneous catheter that forms catheter 28 or that is coupled to catheter 28, e.g., via a fluid coupler. In other embodiments, IMD 26 may include both electrical stimulation as described in IMD 14 and drug delivery therapy.

IMD 26 may also operate using parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

Similar to IMD 14, IMD 26 may include a posture state module that monitors the patient 12 posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Figure 2:
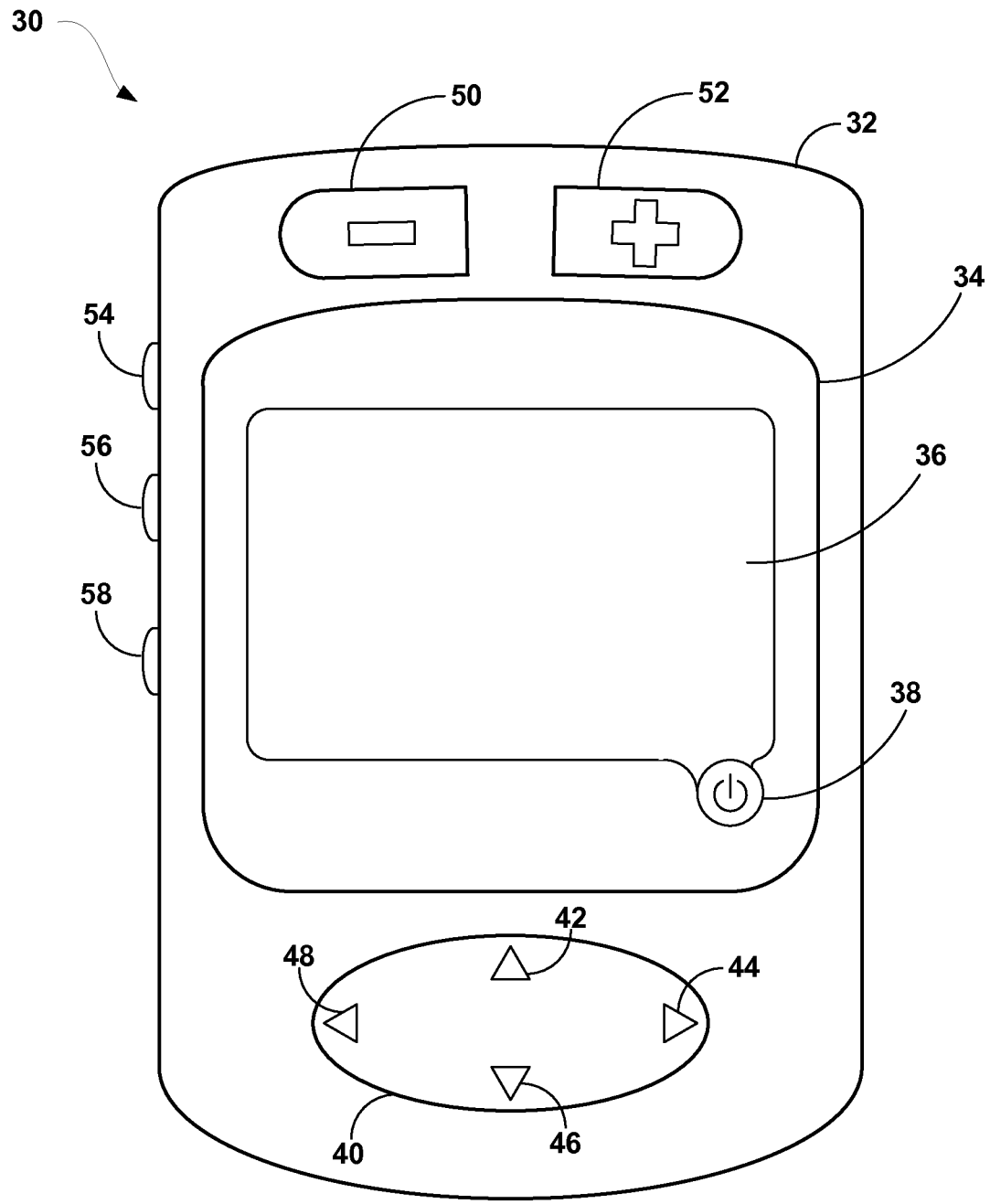
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an implantable medical device. Patient programmer 30 is an example embodiment of external programmer 20 illustrated in FIGS. 1A, 1B and 1C and may be used with either IMD 14 or IMD 26. In alternative embodiments, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate.

Patient programmer 30 also includes display 36, power button 38, increase button 52, decrease button 50, sync button 58, stimulation ON button 54, and stimulation OFF button 56. Cover 34 protects display 36 from being damaged during patient programmer 30 use. Patient programmer 30 also includes control pad 40 which allows a user to navigate through items displayed on display 36 in the direction of arrows 42, 44, 46, and 48. In some embodiments, the buttons and pad 40 may take the form of soft keys (e.g., with functions and contexts indicated on display 36), with functionality that may change, for example, based on current programming operation or user preference. In alternative embodiments, display 36 may be a touch screen in which patient 12 may interact directly with display 36 without the use of control pad 40 or even increase button 52 and decrease button 50.

In the illustrated embodiment, patient programmer 30 is a hand held device. Patient programmer 30 may accompany patient 12 throughout a daily routine. In some cases, patient programmer 30 may be used by a clinician when patient 12 visits the clinician in a hospital or clinic. In other embodiments, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12.

Patient 12 may control the illumination level, or backlight level, of display 36 by using control pad 40 to navigate through the user interface and increase or decrease the illumination level with decrease and increase buttons 50 and 52.

In some embodiments, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may be a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMD 14 or 26. For example, patient programmer 30 may provide a scrollable list of groups, and a scrollable list of programs within each group, via display 36.

Control pad 40 allows patient 12 to navigate through items displayed on display 36. Patient 12 may press control pad 40 on any of arrows 42, 44, 46, and 48 in order to move to another item on display 36 or move to another screen not currently shown on the display. In some embodiments, pressing the middle of control pad 40 may select any item highlighted in display 36. In other embodiments, scroll bars, a scroll wheel, individual buttons, or a joystick may perform the complete or partial functions of control pad 40. In alternative embodiments, control pad 40 may be a touch pad that allows patient 12 to move a cursor within the user interface displayed on display 36 to manage therapy.

Decrease button 50 and increase button 52 provide an input mechanism for patient 12. In general, decrease button 50 may decrease the value of a highlighted stimulation parameter every time the decrease button is pressed. In contrast, increase button 52 may increase the value of a highlighted stimulation parameter one step every time the increase button is pressed. While buttons 50 and 52 may be used to control the value of any stimulation parameter, buttons 50 and 52 may also control patient feedback input. When either of buttons 50 and 52 is selected, patient programmer 30 may initialize communication with IMD 14 or 26 to change therapy accordingly.

When depressed by patient 12, stimulation ON button 54 directs programmer 30 to generate a command for communication to IMD 14 that turns on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some embodiments, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display 36 brightness and contrast, or other similar options. In alternative embodiments, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative embodiments of patient programmer 30 may include other input mechanisms such as a keypad, microphone, camera lens, or any other media input that allows the user to interact with the user interface provided by patient programmer 30.

In alternative embodiments, the buttons of patient programmer 30 may perform different functions than the functions provided in FIG. 2 as an example. In addition, other embodiments of patient programmer 30 may include different button layouts or different numbers of buttons. For example, patient programmer 30 may even include a single touch screen that incorporates all user interface functionality with a limited set of buttons or no other buttons.

Figure 3:
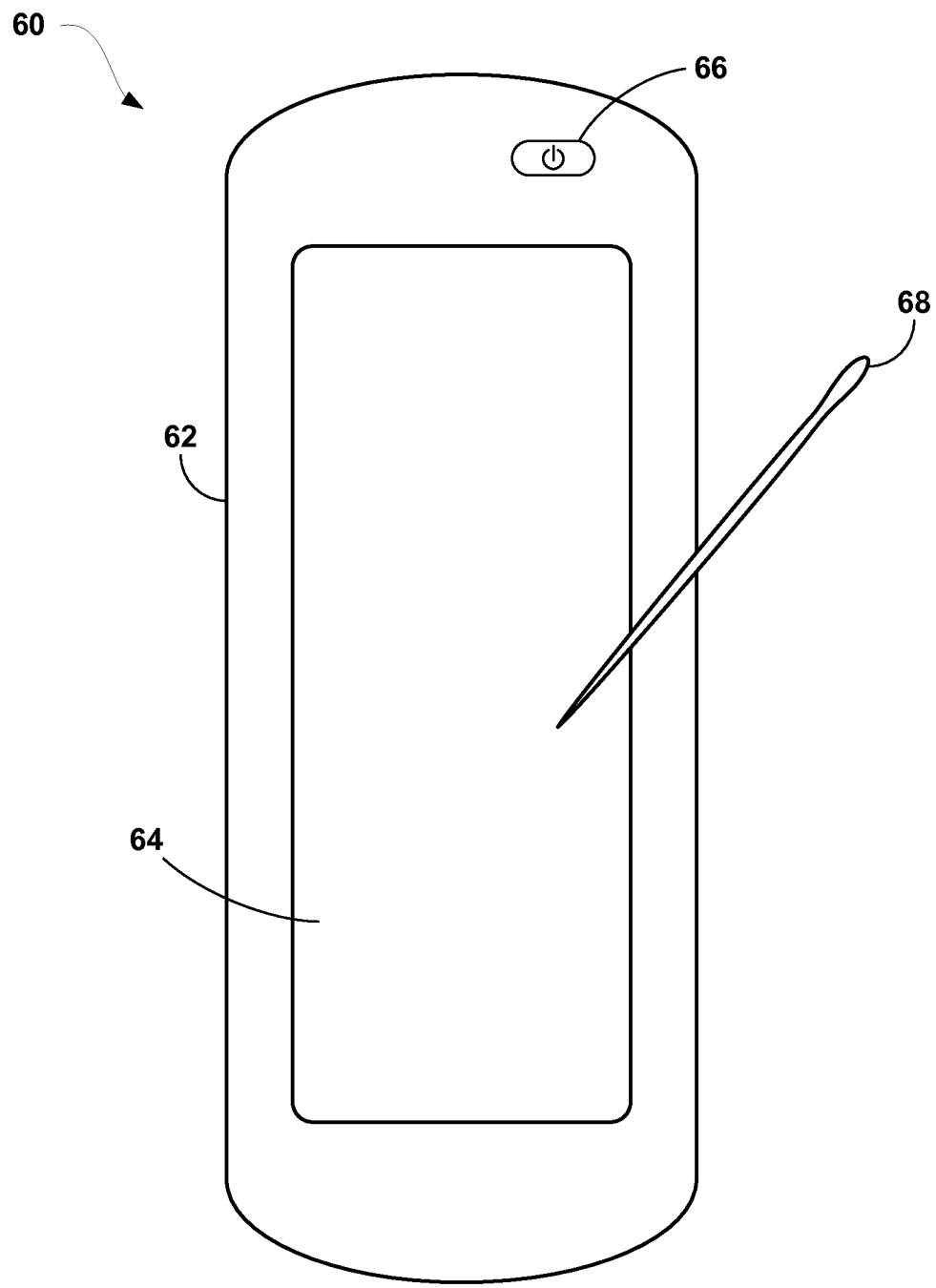
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an implantable medical device. Clinician programmer 60 is an example embodiment of external programmer 20 illustrated in FIGS. 1A, 1B and 1C and may be used with either IMD 14 or IMD 26. In alternative embodiments, clinician programmer 60 may be used with an external medical device. As shown in FIG. 3, clinician programmer 60 provides a user interface (not shown) for a user, such as a clinician, physician, technician, or nurse, to manage and program stimulation therapy. Clinician programmer 60 is protected by housing 62, which encloses circuitry necessary for clinician programmer 60 to operate.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some embodiments, the user may be able to touch display 64 with a finger, pen, or any other pointing device. In alternative embodiments, clinician programmer 60 may include one or more buttons, keypads, control pads, touch pads, or other devices that accept user input, similar to patient programmer 30.

In the illustrated embodiment, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some embodiments, clinician programmer 60 may be a larger device that may be less portable, such as a notebook computer, workstation, or even a remote computer that communicates with IMD 14 or 26 via a remote telemetry device.

Most, if not all, of clinician programmer 60 functions may be completed via the touch screen of display 64. The user may program stimulation therapy, modify programs or groups, retrieve stored therapy data, retrieve posture state information, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
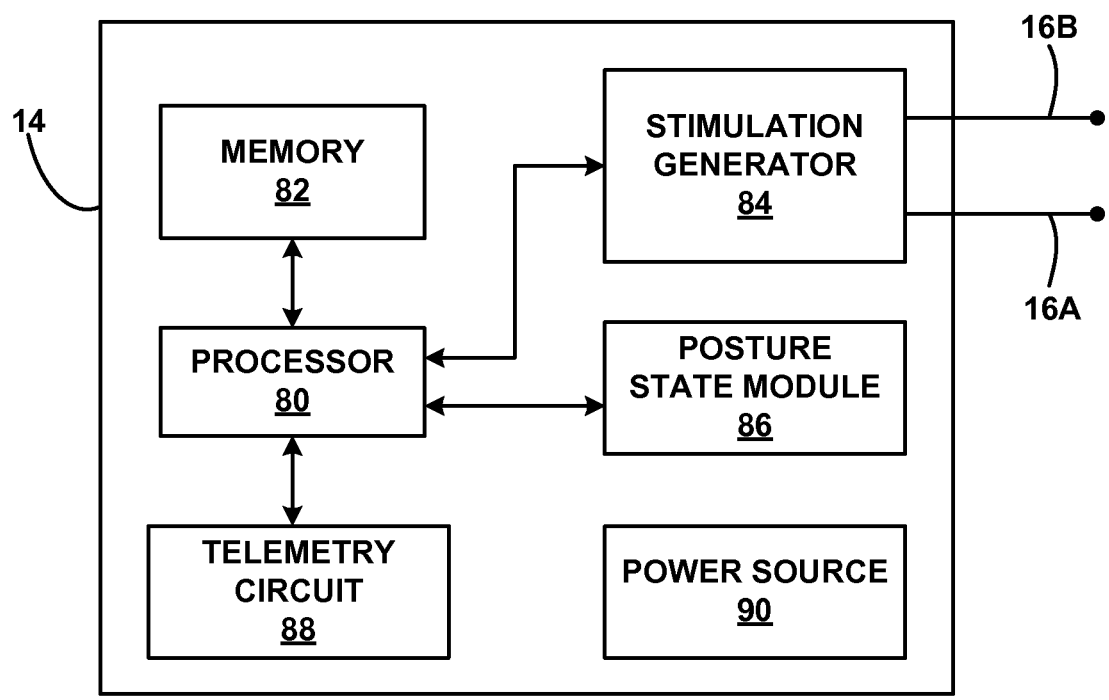
FIG. 4 is a functional block diagram illustrating various components of an implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, and power source 90. Memory 82 may store instructions for execution by processor 80, stimulation therapy data, posture state information, posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other embodiments, stimulation generator 84 may include multiple current or voltage sources to drive more than one electrode combination at one time. In this case, stimulation generator 84 may decrease a stimulation amplitude (e.g., a current or voltage amplitude) to the first electrode combination and simultaneously increase a stimulation amplitude to the second electrode combination to shift the stimulation therapy.

An electrode combination may be represented by a data stored in a memory location, e.g., in memory 82, of IMD 14. Processor 80 may access the memory location to determine the electrode combination and control stimulation generator 84 to deliver electrical stimulation via the indicated electrode combination. To change electrode combinations, amplitudes, pulse rates, or pulse widths, processor 80 may command stimulation generator 84 to make the appropriate changes to therapy according to instructions within memory 82 and rewrite the memory location to indicate the changed therapy. In other embodiments, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12. Processor 80 also may control telemetry circuit 88 to send and receive information to and from external programmer 20. For example, telemetry circuit 88 may send information to and receive information from patient programmer 30. An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and 1200 Hz, more preferably between approximately 5 Hz and 250 Hz, and still more preferably between approximately 30 Hz and 130 Hz.

2. Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between 0.1 milliamps (mA) and 50 mA.

3. Pulse Width: between about 10 microseconds and 5000 microseconds, more preferably between approximately 100 microseconds and 1000 microseconds, and still more preferably between approximately 180 microseconds and 450 microseconds.

In other applications, different ranges of parameter values may be used. For deep brain stimulation (DBS), as one example, alleviation or reduction of symptoms associated with Parkinson's disease, essential tremor, epilepsy or other disorders may make use of stimulation having a pulse rate in the range of approximately 0.5 to 1200 Hz, more preferably 5 to 250 Hz, and still more preferably 30 to 185 Hz, and a pulse width in the range of approximately 10 microseconds and 5000 microseconds, more preferably between approximately 60 microseconds and 1000 microseconds, still more preferably between approximately 60 microseconds and 450 microseconds, and even more preferably between approximately 60 microseconds and 150 microseconds. Amplitude ranges such as those described above with reference to SCS, or other amplitude ranges, may be used for different DBS applications.

Processor 80 stores stimulation parameters in memory 82, e.g., as programs and groups of programs. Upon selection of a particular program group, processor 80 may control stimulation generator 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads.

Posture state module 86 allows IMD 14 to sense the patient posture state, e.g., posture, activity or any other static position or motion of patient 12. In the example of FIG. 4, posture state module 86 may include one or more accelerometers, such as three-axis accelerometers, capable of detecting static orientation or vectors in three-dimensions. For example, posture state module 86 may include one or more micro-electro-mechanical accelerometers. In other examples, posture state module 86 may alternatively or additionally include one or more gyroscopes, pressure transducers or other sensors to sense the posture state of patient 12. Posture state information generated by posture state module 86 and processor 80 may correspond to an activity and/or posture undertaken by patient 12 or a gross level of physical activity, e.g., activity counts based on footfalls or the like.

In some embodiments, processor 80 processes the analog output of the posture state sensor in posture state module 86 to determine activity and/or posture data. For example, processor 80 or a processor of posture state module 86 may process the raw signals provided by the posture state sensor to determine activity counts. In some embodiments, processor 80 may process the signals provided by the posture state sensor to determine velocity of motion information along each axis.

In one example, each of the x, y, and z signals provided by the posture state sensor has both a DC component and an AC component. The DC components may describe the gravitational force exerted upon the sensor and may thereby be used to determine orientation of the sensor within the gravitational field of the earth. Assuming the orientation of the sensor is relatively fixed with respect to patient 12, the DC components of the x, y and z signals may be utilized to determine the patient's orientation within the gravitational field, and hence to determine the posture of the patient.

The AC component of the x, y and z signals may yield information about patient motion. In particular, the AC component of a signal may be used to derive a value for an activity describing the patient's motion. This activity may involve a level, direction of motion, or acceleration of patient 12.

One method for determining the activity is an activity count. An activity count may be used to indicate the activity or activity level of patient 12. For example, a signal processor may sum the magnitudes of the AC portion of an accelerometer signal for "N" consecutive samples. For instance, assuming sampling occurs as 25 Hz, "N" may be set to 25, so that count logic provides the sum of the samples that are obtained in one second. This sum may be referred to as an "activity count."

The number "N" of consecutive samples may be selected by processor 80 or a processor of posture state module 86 based on the current posture state, if desired. The activity count may be the activity portion of the posture state parameter value that may be added to the posture portion. The resulting posture state parameter value may then incorporate both activity and posture to generate an accurate indication of the motion of patient 12.

As another example, the activity portion of the posture state parameter value may describe a direction of motion. This activity parameter may be associated with a vector and an associated tolerance, which may be a distance from the vector. Another example of an activity parameter relates to acceleration. A value quantifying a level of change of motion over time in a particular direction may be associated with the activity portion of a posture state parameter value.

Posture state information from posture state module 86 may be stored in memory 82 for later review by a clinician, used to adjust therapy, present a posture state indication to patient 12, or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture.

IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

A posture state parameter value from posture state module 86 that indicates the posture state may constantly vary throughout the day of patient 12. However, a certain activity (e.g., walking, running, or biking) or a posture (e.g., standing, sitting, or lying down) may include multiple posture state parameter values from posture state module 86. Memory 82 may include definitions for each posture state of patient 12. In one example, the definitions of each posture state may be illustrated as a cone in three-dimensional space. Whenever the posture state parameter value, e.g., a vector, from the three-axis accelerometer of posture state module 86 resides within a predefined cone, processor 80 indicates that patient 12 is in the posture state of the cone. A cone is described for purposes of example. Other definitions of posture states may be illustrated as other shapes, e.g., donuts, in three-dimensional space. In other examples, posture state parameter value from the 3-axis accelerometer may be compared to a look-up table or equation to determine the posture state in which patient 12 currently resides.

Posture responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 12 to, for example, depress one or more keys of patient programmer 30 multiple times during the patient posture state to maintain adequate symptom control. In some embodiments, patient 12 may eventually be able to enjoy posture state responsive stimulation therapy without the need to continue making changes for different postures via patient programmer 30. Instead, patient 12 may transition immediately or over time to fully automatic adjustments based on posture state.

Although posture state module 86 is described as containing a 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple posture state sensors placed at various locations on or within the body of patient 12.

In other embodiments, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some embodiments, to confirm or reject changes in sensed posture state that may result from vibration, patient travel (e.g., in an aircraft, car or train), or some other false positive of posture state.

Wireless telemetry in IMD 14 with external programmer 20, e.g., patient programmer 30 or clinician programmer 60, or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. As one example, external programmer 20 may include the charger to recharge power source 90 of IMD 14. Hence, the programmer and charger may be integrated in the same device. Alternatively, in some cases, a charger unit may serve as an intermediate device that communicates with both the IMD and the programmer. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

Figure 5:
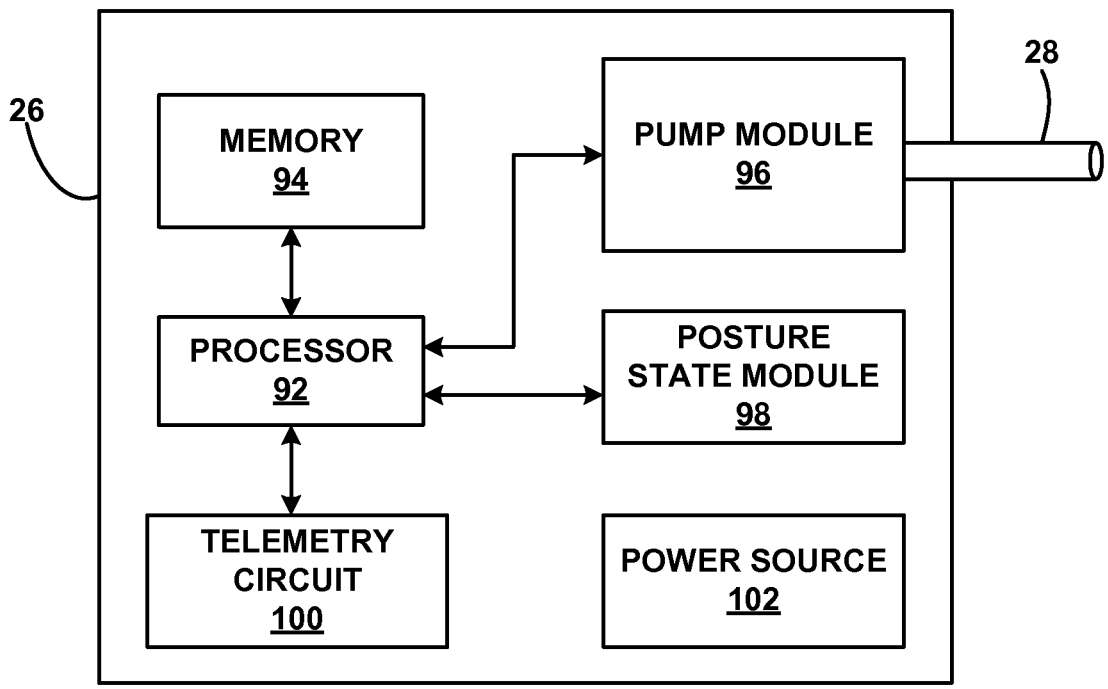
FIG. 5 is a functional block diagram illustrating various components of an implantable drug pump.

FIG. 5 is a functional block diagram illustrating various components of an IMD 26 that is a drug pump. IMD 26 is a drug pump that operates substantially similar to IMD 14 of FIG. 4. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 may control pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts his (or her) posture.

Figure 6:
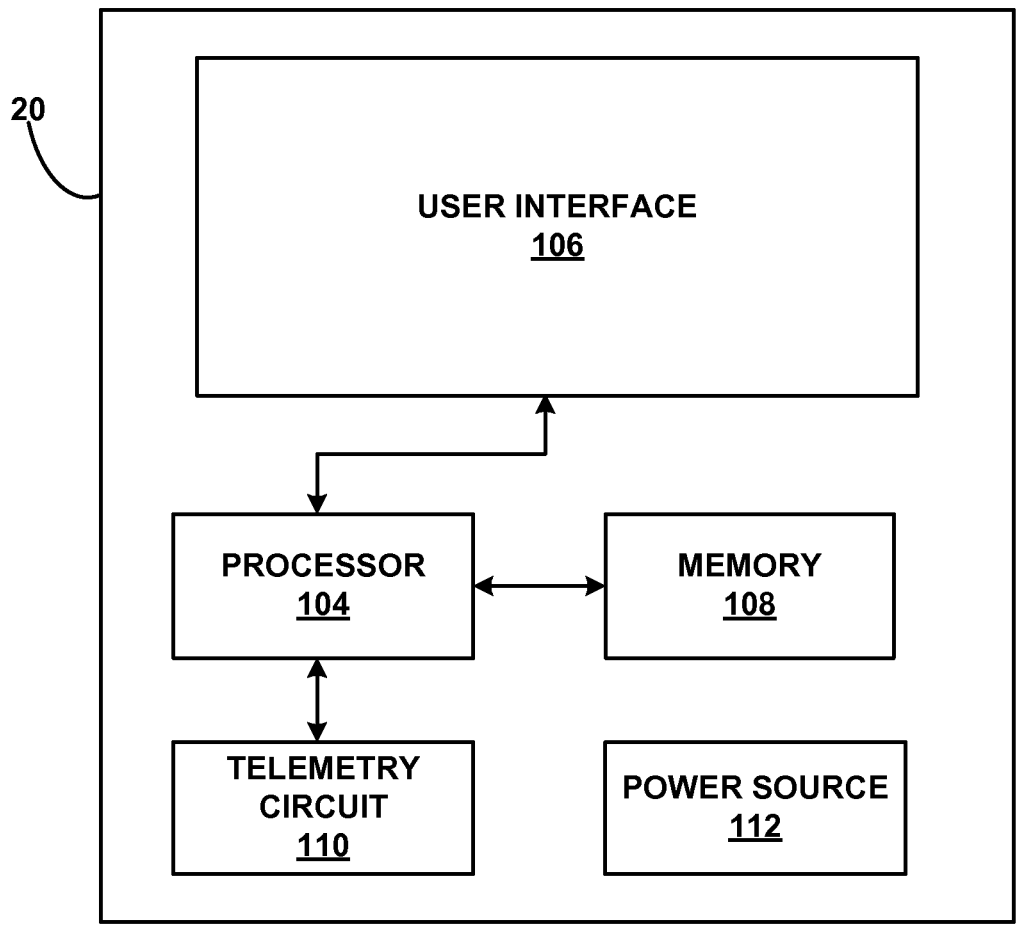
FIG. 6 is a functional block diagram illustrating various components of an external programmer for an implantable medical device.

FIG. 6 is a functional block diagram illustrating various components of an external programmer 20 for IMD 14 or 26. As shown in FIG. 6, external programmer 20 includes processor 104, memory 108, telemetry circuit 110, user interface 106, and power source 112. External programmer 20 may be embodied as patient programmer 30 or clinician programmer 60. A clinician or patient 12 interacts with user interface 106 in order to manually change the stimulation parameters of a program, change programs within a group, turn posture responsive therapy ON or OFF, view therapy information, view posture state information, or otherwise communicate with IMD 14 or 26.

User interface 106 may include a screen and one or more input buttons, as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input buttons for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMD 14 or 26. Memory 108 includes operation instructions for processor 104 and data related to patient 12 therapy.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Figure 7:
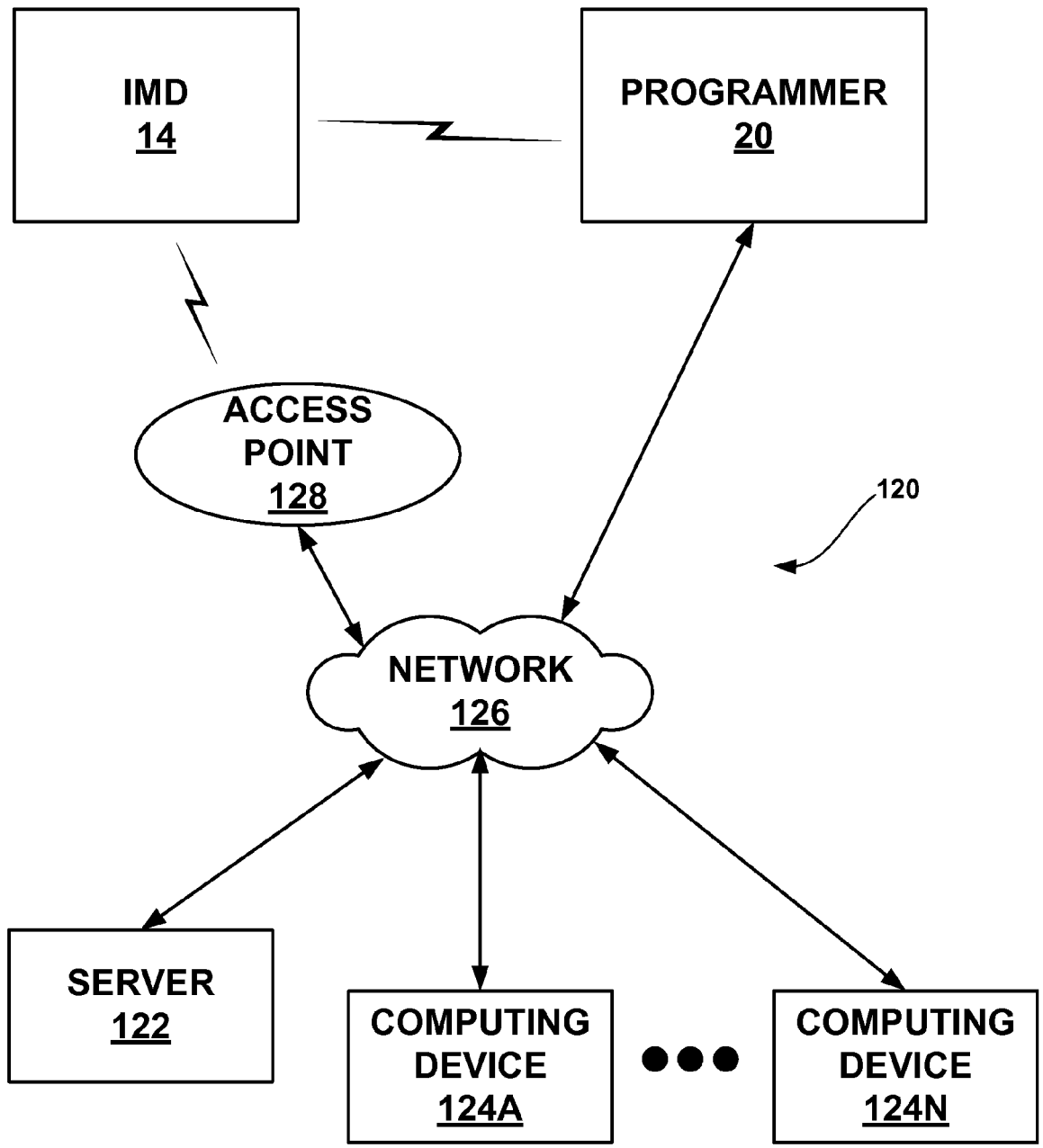
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communicate with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, digital signal processors (DSPs), application specific integrated circuits (ASICs), field programmable gate arrays (FPGAs), programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data. For example, IMD 14 may collect sensed posture state information during therapy delivery that indicate how patient 12 moves throughout each day. In some cases, IMD 14 may directly analyze the collected data to evaluate the patient 12 posture state, such as what percentage of time patient 12 was in each identified posture state. In other cases, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components.

Figure 8A:
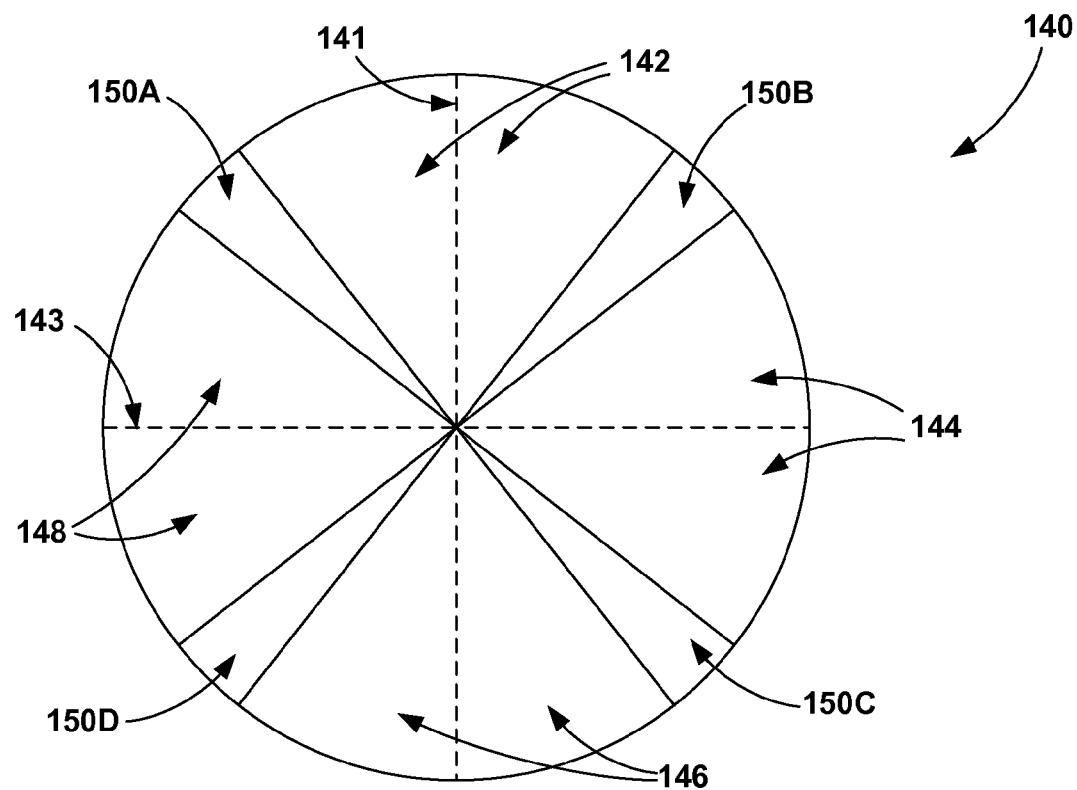
FIGS. 8A-8C are conceptual illustrations of example posture state spaces within which postures state reference data may define the posture state of a patient.
Figure 8B:
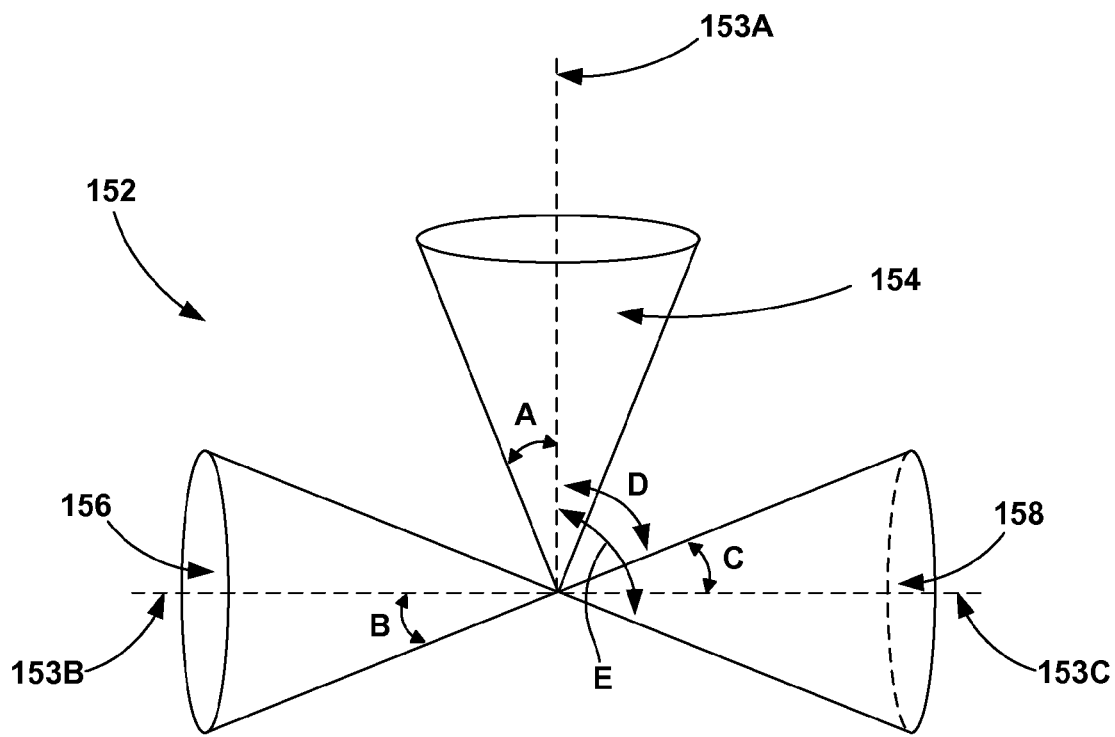
Figure 8C:
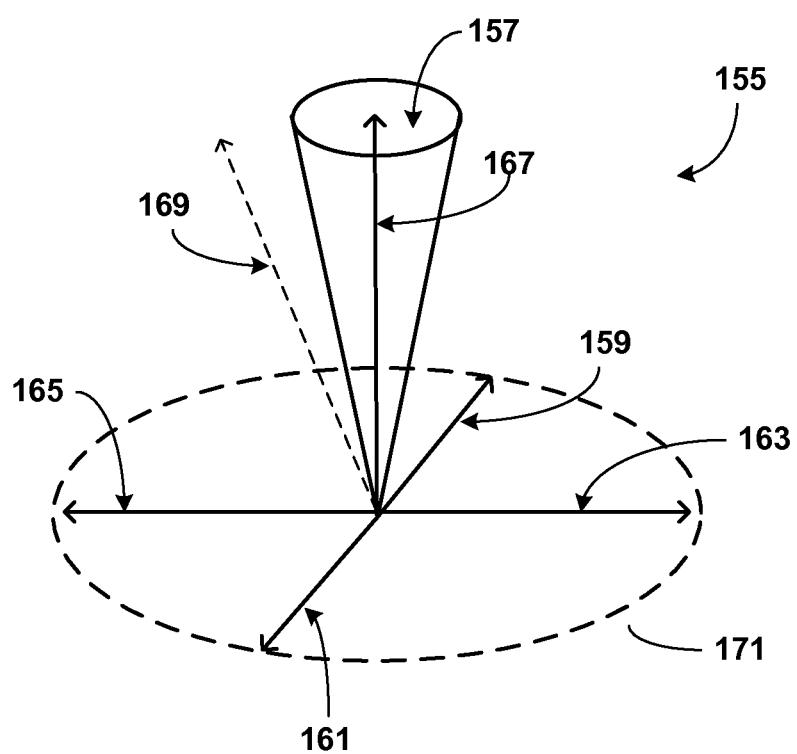

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively, or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A.

The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159 × lying back vector 165, lying back vector 165 × lying right vector 161, lying right vector 161 × lying front vector 163, and lying front vector 163 × lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

A clinician may orient one or more sensors of posture state module 86. For example, as prompted by clinician programmer 60, a clinician may instruct patient 12 to occupy a specified posture, e.g., standing, so that posture state module 86 may sense a reference coordinate vector for the respective posture. The clinician may provide an indication that patient 12 is in the specified posture, e.g., via clinician programmer 60. In response to the indication from the clinician, a vector measured by posture state module 86 may be stored, e.g., in memory 82 of IMD 14, as a reference coordinate vector. The clinician may repeat this process with various specified postures, e.g., lying back or lying front and lying left or lying right. The orientation process may yield a set of reference coordinate vectors. These posture state reference coordinate vectors may be associated with posture state definitions and used to classify the posture of patient 12 within a posture state.

As described with respect to FIGS. 8A-8C, a posture state may be defined by a posture state reference coordinate vector and a tolerance, e.g., angle, cosine, or distance value. Clinician programmer 60 may prompt the clinician to orientate one or more sensors of posture state module 86 to establish values for one or more posture state reference coordinate vectors associated with posture state definitions. Once values for the posture state reference coordinate vectors associated with the posture state definitions have been established, posture state module 86 is enabled to classify the posture state of patient 12 according to the set of posture state definitions. In this manner, the only user input required to enable the set of posture state definitions for posture responsive therapy may be the indications received during the orientation procedure. The values for the posture state reference coordinate vectors established during the orientation process are input into the pre-established posture state definitions.

FIGS. 9-13 describe techniques for associating a therapy adjustment with a posture state based on user input. Since patient 12 may adjust therapy after he (or she) moves to a new posture state or in anticipation of moving to a new posture state, observing the patient's posture states after the adjustment is made may help ensure that the adjusted therapy is associated with the intended posture state. For example, IMD 14 may determine that a therapy adjustment made by patient 12 to increase the amplitude of the current program is associated with the next posture state assumed by patient 12, instead of the posture occupied before a transition to the next posture state. In some examples, IMD 14 may then automatically associate the therapy adjustment with the associated posture state, e.g., if the adjusted therapy parameter was previously undefined for the posture state. In this case, the next time patient 12 engages in the same posture state as the association, IMD 14 will deliver stimulation therapy according to the increased amplitude specified by patient 12 due to the association. Therefore, IMD 14 may use posture search timers and posture stability timers as described with respect to FIGS. 9-13, to learn or update program therapy parameters such that IMD 14 remembers the therapy parameters for therapy delivery for subsequent delivery according to the engaged posture state. In other examples, IMD 14 may store therapy adjustments and corresponding therapy adjustments for purposes of evaluating therapy efficacy.

Figure 9:
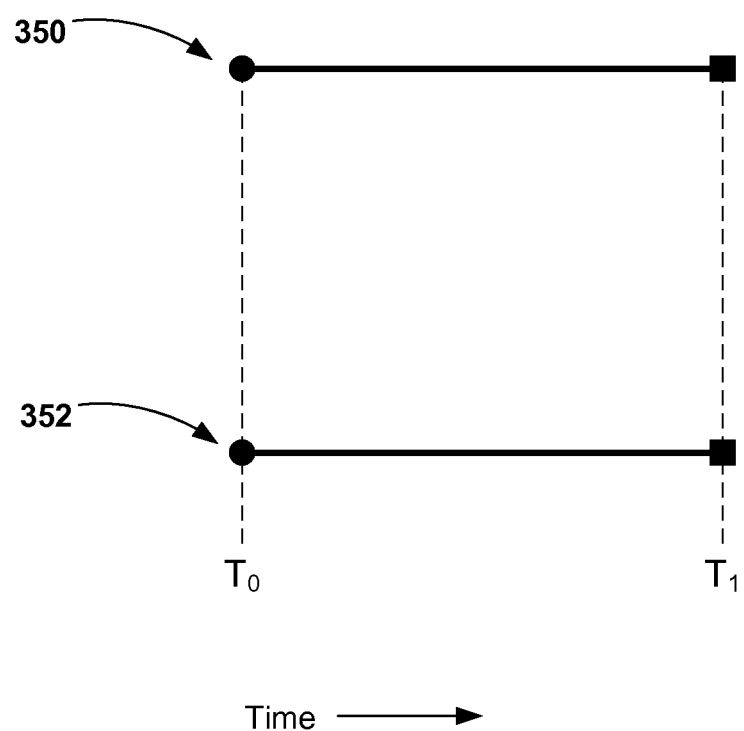
FIG. 9 is a conceptual diagram illustrating example posture search and posture stability timers with one posture state.

FIG. 9 is a conceptual diagram illustrating example posture search timer 350 and posture stability timer 352 when patient 12 remains in one posture state. IMD 14 must be able to correctly associate each therapy adjustment to a therapy parameter with the intended posture state of patient 12 when the therapy adjustment was made. For example, patient 12 may make therapy adjustments to customize the therapy either after patient 12 moves to a different posture state or in anticipation of the next posture state. IMD 14 may employ posture search timer 350 and posture stability timer 352 to track therapy adjustments and the current posture state of patient 12.

Posture search timer 350 has a search period that is a set amount of time from the time the therapy adjustment is made, when posture search timer 350 starts, to when the final posture state must have begun, prior to the expiration of the search period. In addition, posture stability timer 352 has a stability period that is a set amount of time that patient 12 must remain within the final posture state for the therapy adjustment made to be associated with the final posture state. Posture stability timer 352 restarts at any time that patient 12 changes posture states. Therefore, the search period and stability period must overlap for the therapy adjustment to be associated with a posture state not currently engaged by patient 12 when the therapy adjustment was made.

In the example of FIG. 9, patient 12 made a therapy adjustment to one of the therapy parameters, such as voltage or current amplitude, at time $T_0$. Therefore, posture search timer 350 starts at $T_0$ and runs for a predetermined search period until time $T_1$. When the therapy adjustment is made, posture stability timer 352 also starts at time $T_0$ in the current posture state of patient 12 and runs for the stability period that happens to be the same as the search period in this example. Since patient 12 has not changed to any different posture states between times $T_0$ and $T_1$, the stability period also ends at $T_1$. The therapy adjustment made by patient 12 at time $T_0$ is associated with the posture state sensed between times $T_0$ and $T_1$ because both the search period and stability period overlap. In the example of FIG. 9, posture search timer 350 and posture stability timer 352 may not be needed, but their purpose may become clearer in the following examples.

The search period of posture search timer 350 may be of any time duration desired by a device manufacturer, and the clinician may or may not be permitted to set the search period. Generally, the search period may be between approximately 30 seconds and 30 minutes, but it may be set to any time desired, including a time that is outside of that range. More specifically, the search period may be between approximately 30 seconds and 5 minutes in order to provide a reasonable amount of time for patient 12 to be situated in the final desired posture state. More preferably, the search period may be between approximately 2 minutes and 3 minutes. In some examples, and as described in the examples of FIGS. 9-13, the search period is approximately 3 minutes.

In addition, the stability period of posture stability timer 352 may be of any time duration desired by the manufacturer or clinician, where the clinician may or may not be permitted to set the stability period. Generally, the stability period is between 30 seconds and 30 minutes, but it may be set to any time desired, including times outside of that range. More specifically, the stability period may be between approximately 30 seconds and 5 minutes in order to ensure that patient 12 engaged in the final desired posture state for a reasonable amount of time and that the final posture state is not just some transitional or interim posture state. More preferably, the stability period may be between approximately 2 minutes and 3 minutes. In some examples, and as described in the examples of FIGS. 9-13, the stability period is approximately 3 minutes. Although the search period and stability period may have the same duration, they may be different in other examples.

Figure 10:
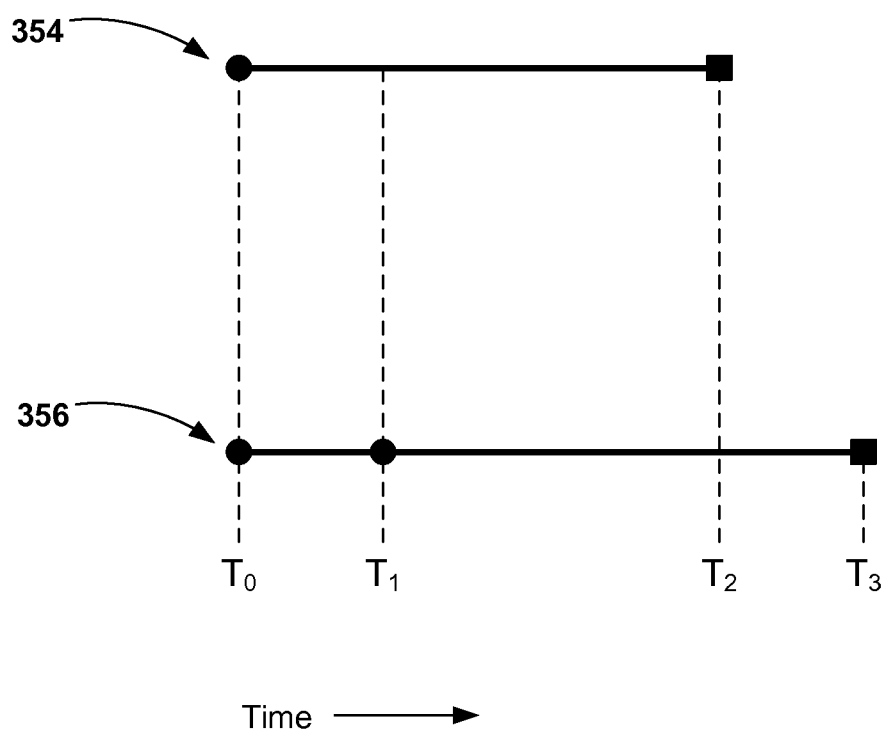
FIG. 10 is a conceptual diagram illustrating example posture search and posture stability timers with one change in posture states.

FIG. 10 is a conceptual diagram illustrating example posture search timer 354 and posture stability timer 356 with one change in posture state. As shown in FIG. 10, patient 12 makes an anticipatory therapy adjustment for the next posture state that patient 12 does not currently occupy. In other words, patient 12 makes a therapy adjustment that the patient may believe is desirable for a given posture, in anticipation of movement to that posture on an imminent or near-term basis. Posture search timer 354 and posture stability timer 356 start at time $T_0$ when patient 12 makes a therapy adjustment in a current posture state occupied at time $T_0$. At time $T_1$, patient 12 changes to a second posture state that is different than the initial posture state occupied at time $T_0$. Therefore, posture stability timer 356 restarts at time $T_1$, with the change to the new posture state, still within the search duration of posture search timer 354.

Time $T_2$ indicates the end of posture search timer 354. Consequently, the only posture state that processor 80 of IMD 14 will associate with the therapy adjustment is the second posture state as long as the second posture state satisfies the stability period of posture stability timer 356, i.e., the patient occupies the second posture state for the stability period. At time $T_3$, patient 12 is still in the second posture when the stability period ends, and the therapy adjustment is associated then to the second posture state because the stability period overlapped with the search period.

It should be noted that patient 12 may make additional therapy adjustments within the search period. If this occurs, any previous therapy adjustments made before the search period or stability period is completed are not associated with any posture state. Therefore, both the search period and stability period must lapse, i.e., expire, in order for a therapy adjustment to be associated with a posture state. However, in some examples, IMD 14 may allow therapy adjustments to be associated with posture states as long as the search period has lapsed or no different posture state was sensed during the search period.

Figure 11:
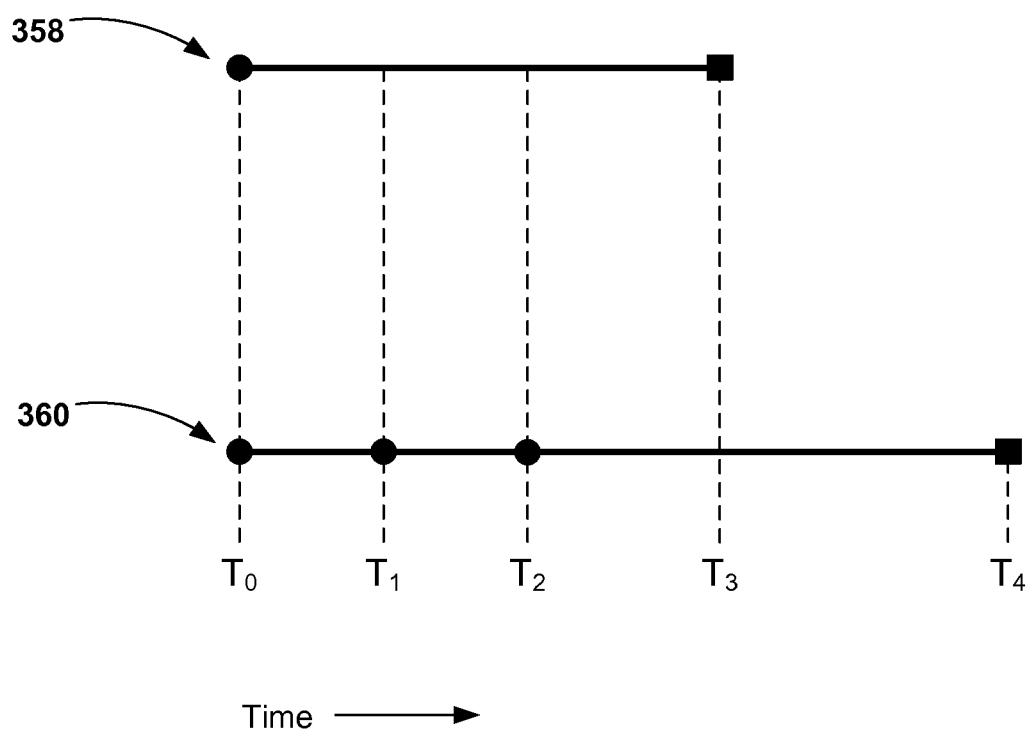
FIG. 11 is a conceptual diagram illustrating example posture search and posture stability timers with two changes in posture states.

FIG. 11 is a conceptual diagram illustrating example posture search timer 358 and posture stability timer 360 with two changes in posture states. As shown in FIG. 11, patient 12 makes an anticipatory therapy adjustment but is engaged in an interim posture state before settling into the final posture state. Posture search timer 358 and posture stability timer 360 both start at time $T_0$ when patient 12 makes a therapy adjustment in a current posture state engaged at time $T_0$. The therapy adjustment value may be an adjustment, a parameter value, or a selection of a program or program group.

At time $T_1$, patient 12 changes to a second posture state, or an interim posture state, that is different than the initial posture state engaged at time $T_0$. Therefore, posture stability timer 360 restarts at time $T_1$, still within the search duration of posture search timer 358. At time $T_2$, patient 12 changes to a third posture state, and again posture stability timer 360 restarts. Time $T_3$ indicates the end of posture search timer 358, so the only posture state that processor 80 of IMD 14 will associate with the therapy adjustment is the third posture state begun at time $T_2$ as long as the third posture state satisfies the stability period of posture stability timer 360. At time $T_4$, patient 12 is still in the third posture when the stability period ends, and the therapy adjustment is associated then to the third and final posture state because the stability period of the third posture state overlapped with the search period.

Figure 12:
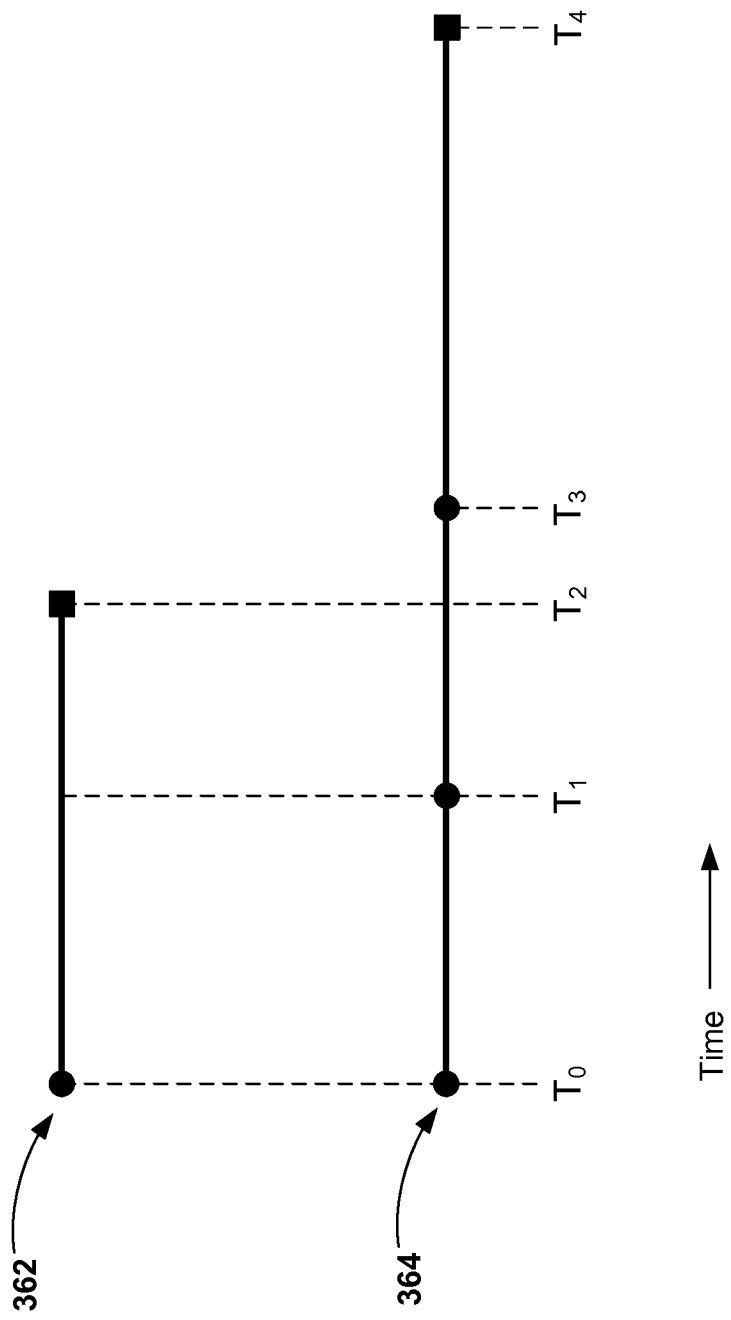
FIG. 12 is a conceptual diagram illustrating example posture search and posture stability timers with the last posture state change occurring outside of the posture search timer.

FIG. 12 is a conceptual diagram illustrating example search timer 362 and posture stability timer 360 with the last posture state change occurring outside of the posture search timer. As shown in FIG. 12, patient 12 makes an anticipatory therapy adjustment but is engaged in an interim posture state too long before settling into the final posture state for the therapy adjustment to be associated with any posture state. Posture search timer 362 and posture stability timer 364 both start at time $T_0$ when patient 12 makes a therapy adjustment in a current posture state engaged at time $T_0$. At time $T_1$, patient 12 changes to a second posture state, or an interim posture state, that is different than the initial posture state engaged at time $T_0$. Therefore, posture stability timer 364 restarts at time $T_1$, still within the search duration of posture search timer 362.

However, the search timer expires at time $T_2$, before patient 12 changes to a third posture state at time $T_3$, when posture stability timer 364 again restarts. The stability period for the third posture state then expires at time $T_4$. Since the third posture state did not start before the search period expired at time $T_2$, the search period and stability period do not overlap and the therapy adjustment from time $T_0$ is not associated with any posture state. In other examples, therapy adjustments may still be associated with the posture state occupied at time $T_0$ when the search period and last stability period do not overlap.

The following is a further illustration of the example described in FIG. 12 to put the example in context of an example patient scenario. Patient 12 may be engaged in the upright posture state when patient 12 makes the therapy adjustment at time $T_0$. In this example, the search duration is three minutes and the stability duration is also three minutes. After two minutes, or at time $T_1$, patient 12 transitions to the lying left posture, which causes processor 80 of IMD 14 to restart posture stability timer 360.

If patient 12 were to remain within the lying left posture for the full three minutes of the stability duration, then the therapy adjustment would be associated with the lying left posture. However, patient 12 leaves the lying left posture after only two minutes, or at time $T_3$, outside of the search duration. At this point, the therapy amplitude made at time $T_0$ will not be associated with the next posture state of patient 12.

The next posture state may be the lying back posture state. Once IMD 14 senses the lying back posture state, IMD 14 may change therapy according to the therapy parameters associated with the lying back posture, because IMD 14 is operating in the automatic posture response mode. No new associations with the therapy adjustment would be made in the example of FIG. 12.

Figure 13:
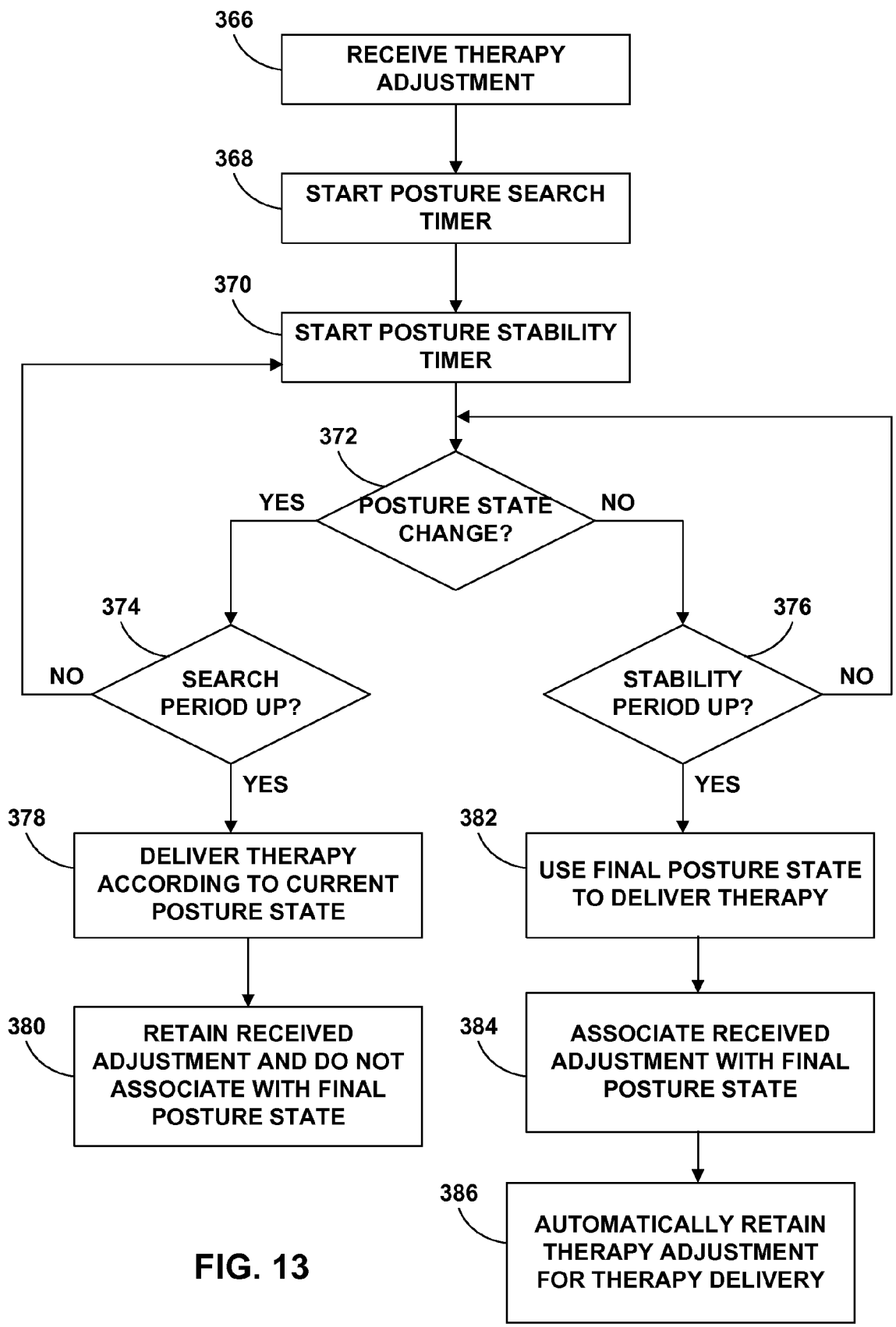
FIG. 13 is a flow diagram illustrating an example method for associating a received therapy adjustment with a posture state.

FIG. 13 is a flow diagram illustrating an example method for associating a received therapy adjustment with a posture state. Although the example of FIG. 13 will be described with respect to patient programmer 30 and IMD 14, the technique may be employed in any external programmer 20 and IMD or other computing device. As shown in FIG. 13, user interface 106 receives the therapy adjustment from patient 12 (366) and processor 80 of IMD 14 immediately starts the posture search timer (368) and the posture stability timer (370).

If the posture state of patient 12 does not change (372), processor 80 checks to determine if the stability period has expired (376). If the stability period has not expired (376), processor 80 continues to sense for a posture state change (372). If the stability period has expired (376), the processor 80 uses the final posture state, i.e., the currently sensed posture state, to select therapy parameters to deliver therapy (382). Processor 80 associates the therapy adjustment with the final posture state (384). For example, processor 80 may associate the therapy adjustment with the final posture state for purposes of analyzing therapy efficacy. Processor 80 may also automatically retain, i.e., associate, the therapy adjustment with the final posture state for posture-responsive therapy delivery (386). In this manner, by automatically associating the therapy adjustment for posture-responsive therapy delivery, during the next time the patient occupies that final posture state, the IMD 14 will apply the newly associated therapy adjustment value, thereby automatically defining the therapy to be delivered for that posture state, at least in part on the basis of the associated therapy adjustment. If the therapy adjustment value was 5.0 volts, then IMD 14 will apply an amplitude value of 5.0 volts the next time the patient occupies the posture. Again, the therapy adjustment value may be an adjustment, a parameter value, or a selection of a program or program group. In each case, the therapy adjustment value entered by the patient is used to define a previously undefined therapy parameter value for the respective posture state based on the patient input.

The search timer and stability timer ensure that the patient is in the posture state or transitioning to the posture state when the patient therapy adjustment is received. If the search and stability timers are satisfied, the patient therapy adjustment is associated with the posture state (384). Hence, in a case in which a plurality of posture states are defined, and therapy parameter values for at least some of the posture states are defined, patient input indicating a therapy parameter value can be used to define a previously undefined therapy parameter value for a posture state while the patient is in the respective posture state or transitioning to the respective posture state. The previously undefined therapy parameter value then can be defined by the programmer based on the patient input.

If processor 80 senses a posture state change (372), processor 80 determines if the search period has expired (374). If the search period has not expired (374), then processor 80 restarts the posture stability timer (370). If the search period has expired (374), then processor 80 delivers therapy to patient 12 according to the current posture state (378). Processor 80 retains the therapy adjustment and does not associate the therapy adjustment with the final posture state because the search period did not overlap with the stability period (380). Because the search or stability timer was not satisifed, the therapy adjustment cannot be reliably associated with the posture state. Consequently, the pertinent therapy parameter value remains undefined.

In some embodiments, a posture stability timer may be employed without the use of a posture search timer. As described with respect to posture stability timer 350, the posture stability timer may be started after a therapy adjustment and reset each time patient 12 changes posture states prior to expiration of the posture stability timer. When the posture stability timer expires, the therapy adjustment may be associated with the posture state that patient 12 is occupying at that time. In this manner, the therapy adjustment may be associated with the first stable posture state, i.e., the first posture state that remains stable for the duration of the posture stability timer, after the therapy adjustment regardless of the amount of time that has past since the therapy adjustment.

Any patient therapy adjustments may be applied immediately following receipt of the adjustments. However, processor 80 may not change posture state-responsive therapy to patient 12 at any time until the stability period expires. In other words, the posture stability timer may run independently of the posture search timer to always track posture states independently of therapy adjustments. Therefore, IMD 14 may not perform any automatic posture responsive stimulation until the posture state of patient 12 is stable and the stability period has expired. In this manner, patient 12 may not be subjected to rapidly changing therapy when transitioning between multiple posture states. Alternatively, IMD 14 may employ a separate posture stability timer for changing therapy during automatic posture response from the therapy adjustment related posture stability timer described herein.

Figure 14:
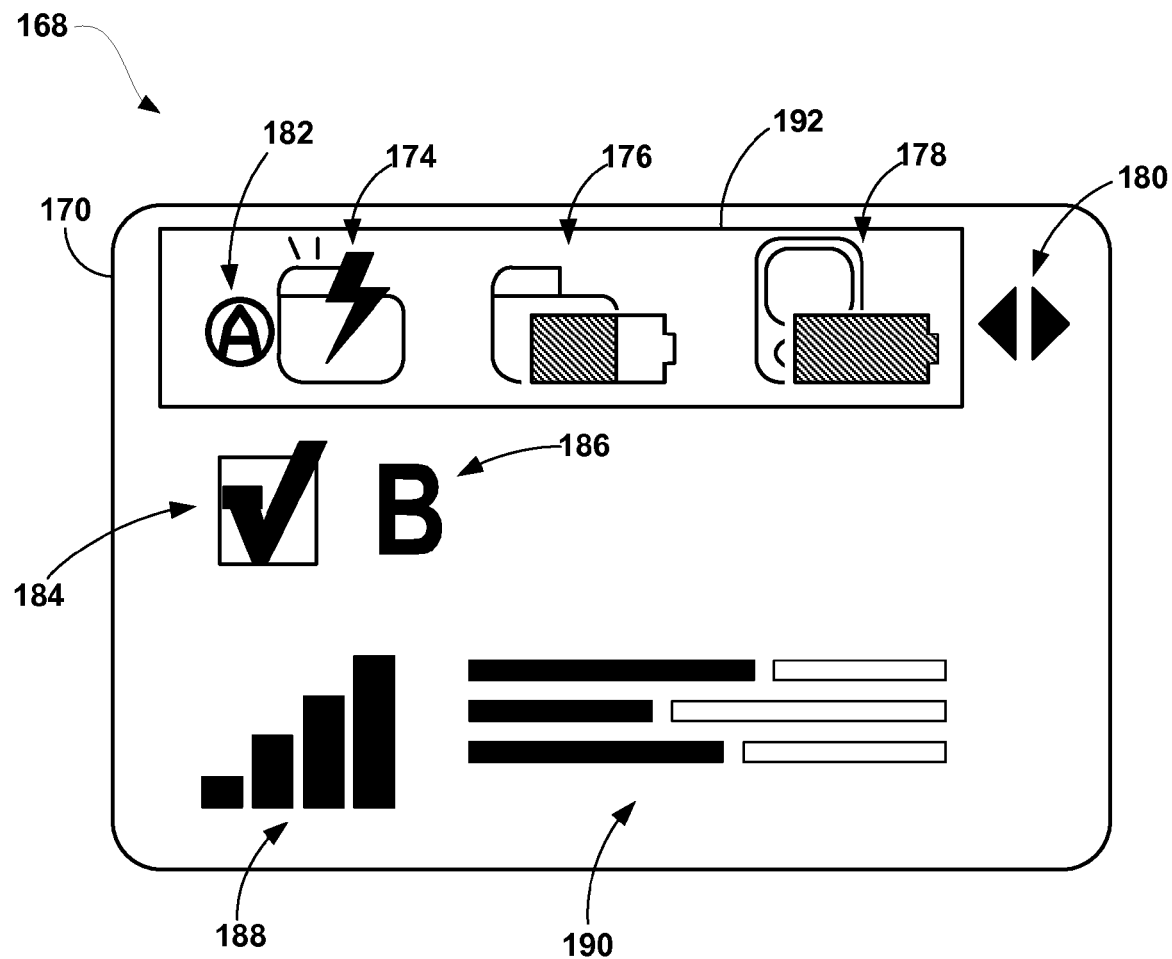
FIG. 14 is a conceptual diagram illustrating an example user interface of a patient programmer for delivering therapy information to the patient.

FIG. 14 is a conceptual diagram illustrating an example user interface 168 of a patient programmer 30 for delivering therapy information to patient 12. In other examples, a user interface similar to user interface 168 may also be shown on clinician programmer 60. In the example of FIG. 14, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example of screen 170, selection box 192 is positioned so that patient 12 may use navigation buttons 44 and 48 to move to the automatic posture response screen, the volume screen, the contrast or illumination screen, the time screen, and the measurement unit screen of patient programmer 30. In these screens, patient 12 may be able to control the use of the automatic posture response feature and adjust the patient programmer 30 features. Patient 12 may only adjust the features surrounded by selection box 192.

Group identifier 186 indicates one of possibly several groups of programs that can be selected for delivery to patient 12. Group selection icon 184 indicates whether the displayed group, e.g., group B in FIG. 14, is actually selected for delivery to patient 12. If a presently displayed group is selected, group selection icon 184 includes a box with a checkmark. If a presently displayed group is not selected, group selection icon 184 includes a box without a checkmark. To navigate through the program groups, a user may use control pad 40 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 14, no program number is indicated in program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available for each program. In some embodiments, numerical values of each program's amplitude may be shown in addition to or in place of amplitude graph 190. In other embodiments of user interface 168 specific to drug delivery using IMD 26, amplitude graph 190 may show the flow rate of drugs or frequency of bolus delivery to patient 12. This information may be shown in numerical format as well.

Automatic posture response icon 182 indicates that IMD 14 is generally activated to automatically change therapy to patient 12 based upon the posture state detected by posture state module 86. However, automatic posture response icon 182 is not present next to group identifier 186. Therefore, group "B" does not have automatic posture response activated for any of the programs within group "B." Some groups or individual programs in groups may have automatic posture response, i.e., automatic adjustment of one or more therapy parameters in response to posture state indication, selectively activated or deactivated based on settings entered by a clinician, or possibly patient 12. In some cases, if posture responsive therapy supported by the automatic posture response feature is desired, patient 12 may need to switch therapy to a different group that has automatic posture response activated for IMD 14 to adjust therapy according to the patient 12 posture state.

Figure 15:
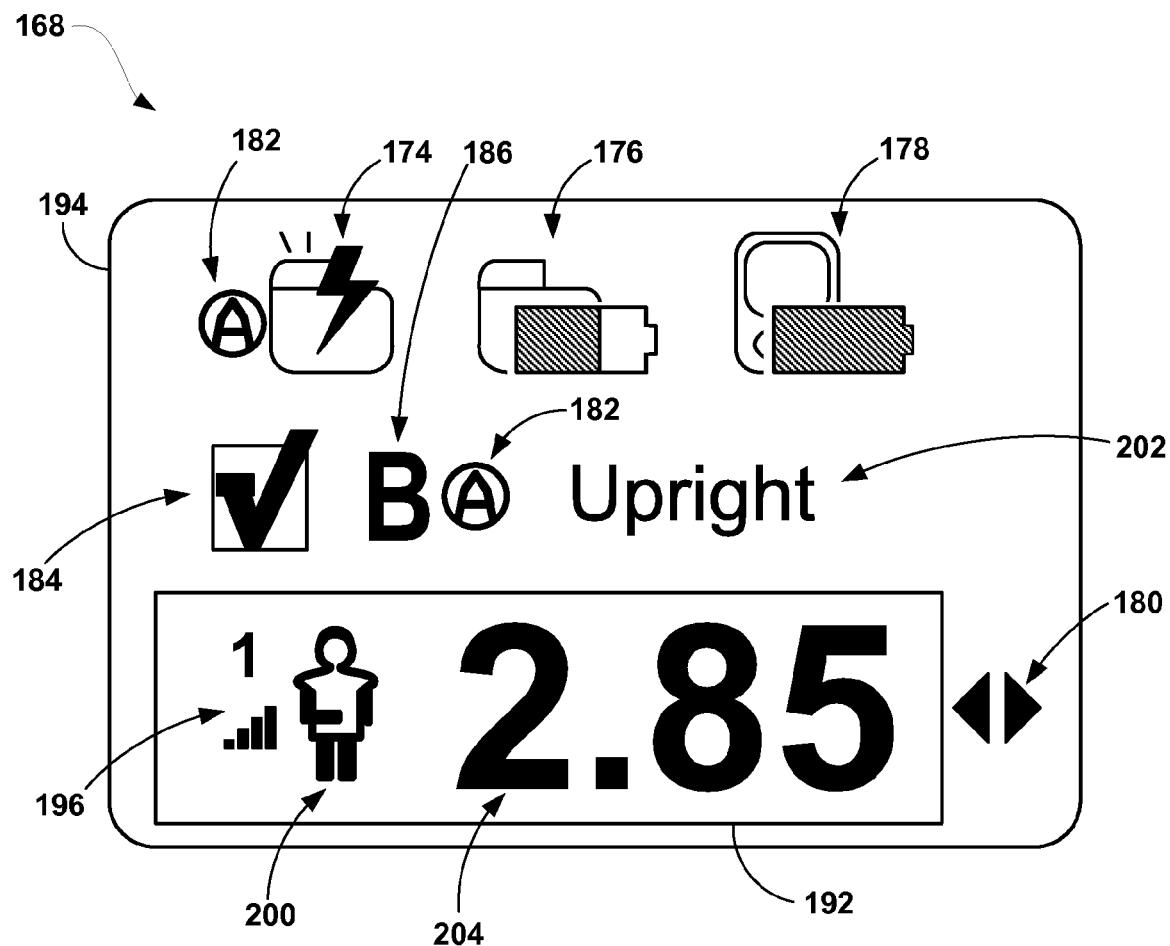
FIG. 15 is a conceptual diagram illustrating an example user interface of a patient programmer for delivering therapy information that includes posture information to the patient.

FIG. 15 is a conceptual diagram illustrating an example user interface 168 of a patient programmer 30 for delivering therapy information that includes posture information to the patient. In other examples, user interface 168 may also be shown on clinician programmer 60. In the example of FIG. 15, display 36 of patient programmer 30 provides user interface 168 to the user, such as patient 12, via screen 194. Screen 194 includes stimulation icon 174, IMD battery icon 176, programmer battery icon 178, and automatic posture response icon 182, similar to screen 170 of FIG. 14. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding group, program, amplitude, automatic posture response status, and posture state information. More or less information may be provided to patient 12, as desired by the clinician or the patient. For example, in some embodiments, user interface 168 may provide information regarding additional therapy parameters, such as rate, pulse width, and electrode configuration (e.g., electrode combination and polarities).

Group identifier 186 indicates that group "B" is active, and automatic posture response icon 182 indicates group "B" (containing one or more programs) is activated to allow IMD 14 to automatically adjust therapy according to the patient 12 posture state. Specifically, the patient 12 posture state is the patient's certain posture in the example of FIG. 15. Program identifier 196 illustrates that information regarding program "1" of group "B" is displayed on screen 194, such as amplitude value 204 illustrating the current voltage amplitude of program "1" is 2.85 Volts. Patient 12 may scroll through different programs of the group by using navigation arrows 180 via navigation buttons 44 and 48 of control pad 40.

In addition, posture state icon 200 shows that IMD 14 is detecting that patient 12 is in the upright or standing posture. Posture state text 202 supplements posture state icon 200 by explaining in words to patient 12 what posture is being detected by posture state module 86 of IMD 14. Posture state icon 200 and posture state text 202 changes according to the detected posture state detected by IMD 14. Selection box 192 indicates that patient 12 may view other programs within group "B" using selection arrows 180. Selection box 192 may be moved to select other screen levels with control pad 40 in order to navigate through other stimulation groups or adjustable elements of the therapy. When patient 12 selects a different program with control pad 40, program identifier 196 will change number to correctly identify the current program viewed on screen 194

The posture state may be communicated to the external programmer immediately when IMD 14 detects a posture change, or communicated periodically or non-periodically by IMD 14 unilaterally or upon receiving a request from the programmer. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

As mentioned above, in addition to graphical, textual or other visible indications of posture state, the external programmer may present audible and/or tactile indications of posture state via any of a variety of audible or tactile output media. Again, an audible indication may be spoken words stating a posture state, or different audible tones, different numbers of tones, or other audible information generated by the programmer to indicate posture state. A tactile indication may be different numbers of vibratory pulses delivered in sequence or vibratory pulses of different lengths, amplitudes, or frequencies.

Figure 16:
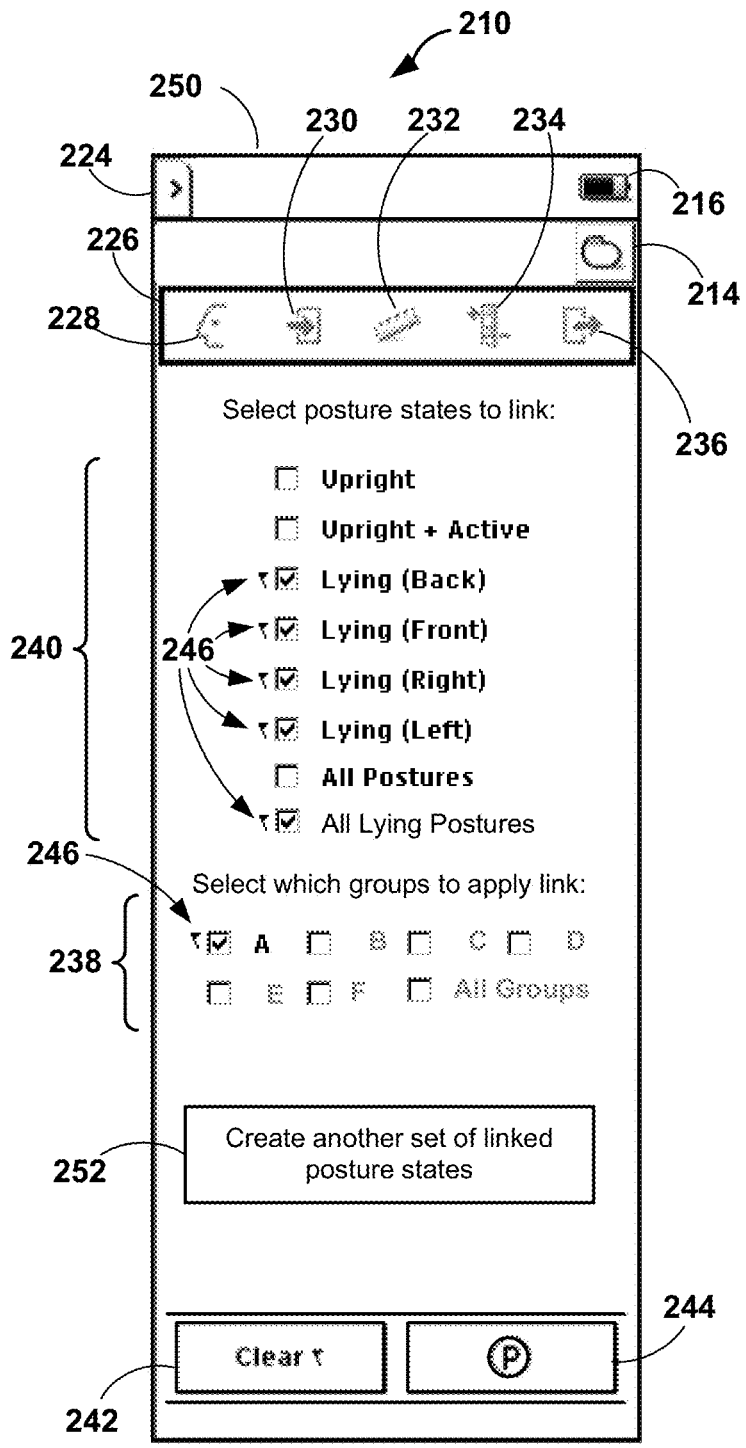
FIG. 16 is a conceptual diagram illustrating an example screen that may be displayed by a user interface of a clinician programmer to permit a user to link posture states together for posture state-responsive therapy.

FIG. 16 is a conceptual diagram illustrating an example screen 250 that may be displayed by user interface 210 of a clinician programmer 60 to present posture information to a user, such as a clinician. Example screen 250 also or alternatively could be provided on a user interface of patient programmer 30, in some embodiments. In the example of FIG. 16, display 64 of clinician programmer 60 provides screen 250 to the user via user interface 210. Screen 250 includes stimulation icon 214, programmer battery icon 216, operational menu 224, selection box 226, group selection list 238, posture state selection list 240, clear button 242, and program button 244. Selection of operational menu 224 may allow a user to adjust the volume, contrast, illumination, default printer, clock, or other similar options of clinician programmer 60. As described in further detail below, screen 250 permits a user to link posture states together for posture-responsive therapy. Other examples of screen 250 may provide more or less information to the user.

Selection box 226 includes patient data icon 228, data recording icon 230, device status icon 232, programming icon 234, and data reporting icon 236. Selection box 226 may allow the user to navigate to other screens to manage therapy delivery. For example, each of icons 228-236 may be selected to display other therapy information. Additionally, each of icons 228-236 may serve as a drop-down menu that allows selection of various subcategories. As one example, programming icon 234 may display a list of programming subcategories available for user selection, such as create new program, program stimulation, orient device, restore initial settings, and the like.

Screen 250 may allow a user to link various posture states for purposes of posture-responsive therapy. When a set of linked posture states are selected for posture-responsive therapy, one set of therapy parameter values may be associated with all of the linked posture states. For example, when a set of therapy parameter values is associated with one posture state of a set of linked posture states, the set of therapy parameter values may be automatically associated with the additional posture states of the set of linked posture states. In this manner, a set of therapy parameter values may be conveniently and efficiently propagated across several posture states so that there is no need to enter multiple sets of identical therapy parameter values. Also, in some embodiments, linking a plurality of posture states may enable or disable therapy delivery features. For example, linking a plurality of posture states may disable cycling (e.g., cycling between an "on" period of therapy delivery and an "off" period without therapy delivery), pulse rate adjustment, and/or pulse width adjustments.

Often, different posture states may be associated with different therapy parameter values. When the same therapy parameter values can be used for multiple posture states, either as an initial starting point or chronically, this linking feature provides an expeditious mode for programming. Additionally, when a user adjusts a set of therapy parameter values for one posture state of the set of linked posture states, the adjustment may be automatically made for the additional posture states of the set of linked posture states. In other words, changes to a therapy parameter value set may be automatically propagated among any other posture states identified as being linked to one another, permitting global or semi-global changes to be quickly made.

Hence, using screen 250, a user can link linking a plurality of posture states of a patient, and select a program group to apply to the linked posture states. In this manner, by selecting a program group, the user selects a set of therapy parameter values for delivery of therapy to the patient 12 by IMD 14 for each of the linked posture states. Based on this user selection, programmer 60 defines the therapy to be delivered to the patient by IMD 14 for each of the linked posture states. The defined therapy can be downloaded to IMD 14 as program instructions. If IMD 14 is configured to recognize the linking concept, programmer 60 may simply download the linking information and the group or groups to be applied to the link. If IMD 14 does not recognize the linking concept, programmer 60 may download an explicit indication of the program group to be used for each of the linked posture states.

The user may select which posture states to link using posture state selection list 240. In the example of FIG. 16, in addition to the individual posture states, posture state selection list 240 includes listings for "All Posture States" and "All Lying States." These listings may allow a user to select all of the posture states or all of the lying posture states, e.g., "Lying (Back)," "Lying (Front)," "Lying (Right)," and "Lying (Left)," simultaneously. If the user would like to link several posture states, selecting all of the postures states simultaneously and then deselecting individual posture states may be more efficient than selecting all of the desired posture states individually. Allowing a user such as a clinician or patient to select the same therapy parameter values for all of the lying posture states simultaneously may be beneficial, especially when the same therapy parameter values may be used for all of the lying posture states.

Additionally, the user may select which groups to apply to the set of linked posture states group selection list 238, which displays a listing of groups that are available for selection for therapy delivery to patient 12. In the example of FIG. 16, group selection list 238 includes a listing for "All Groups," which may allow a user to select all of the groups simultaneously. Then, the user may deselect some of the groups to leave only desired groups selected. Selecting all groups provides a shortcut in the event numerous groups are to be selected. Each group may define a group of programs, and each program may define a set of therapy parameter values. The programs in a given group may be used to control therapy parameter values for delivery of different or related therapies on a simultaneous or time-interleaved basis.

For example, group "A" may specify that programs 1, 2 and 4 are to be delivered together (simultaneously or time-interleaved). The individual programs specify the therapy parameter values for each program, e.g., amplitude, pulse width, pulse rate, electrode configuration, or the like. Accordingly, specification or adjustment of therapy parameter values for different posture states or linked posture states may refer to specification or adjustment of individual therapy parameter values, specification or selection of different programs in a group, or specification or selection of different groups.

Linked posture states may be selected on a group-by-group basis. Alternatively, in some embodiments, posture states may automatically be linked for all groups rather than allowing the user to select which particular program groups will use a set of linked posture states. The user may also create more than one set of linked posture states using link button 252. In response to activation of link button 252, screen 250 may display an additional posture state selection list 240 and group selection list 238 to allow the user to define a second set of linked posture states. In this case, the user may specify multiple sets of different linked posture states and associate the individual sets of linked posture states with particular groups, on a selective basis.

In the example of FIG. 16, a user has selected to link the four different lying posture states, e.g., "Lying (Back)," "Lying (Front)," "Lying (Right)," and "Lying (Left)," together. This means that all of the linked posture states will share the same set of therapy parameter values, e.g., in terms of values associated with a program or group of programs. The user may have selected to link the four lying states by selecting the "All Lying States" listing. The selection of a posture state is indicated by displaying a check mark in the box next to the name of the posture state within posture state selection list 240. Upon selection of "All Lying States," check marks may automatically be displayed next to the name of the lying posture states. Boxes without check marks are displayed next to unselected posture states.

When the set of linked posture states is selected for posture-responsive therapy, a single set of therapy parameter values may be associated with each of the four linked lying posture states. When the patient enters any of the four lying posture states, e.g., any of the posture states associated with the four lying states, he will receive the same therapy. Additionally, if the set of therapy parameter values is adjusted for one lying posture state, the adjustment will be automatically made for all of the lying posture states in the set of linked posture states. For example, when a patient or clinician adjusts a therapy parameter value for one posture state, programmer 60 may apply the same therapy parameter adjustment for all linked posture states.

Additionally, in the example of FIG. 16, the user has selected to link the lying group posture states for program group "A." Similar to posture state selection list 240, a check mark next to a group name may represent that the program group is selected. Boxes without check marks are displayed next to unselected groups. As previously stated, in other embodiments, posture states may automatically be linked for all groups rather than allowing the user to select which program groups will use the set of linked posture states.

By selecting posture states to be linked, the user may specify posture states that will share the same therapy parameter values, e.g., in terms of specific values, programs, or groups. The example of FIG. 16 contemplates sharing of the same groups among linked posture states such that changes to therapy parameter values for programs in a given group, when the patient is in one posture state of the set of linked posture states, are applicable to all other posture states in the set of linked posture states. In this manner, assuming the "Lying (Back)" and "Lying (Right)" posture states are linked, if the patient changes an amplitude associated with a program in a given group while occupying the "Lying (Right)" posture state, then the same change will be effective for the "Lying (Back)" posture state, because the two posture states are linked. The changes may be entered by a patient during the course of therapy, for example, or entered by a clinician in the clinic or remotely.

By selecting groups to which linking will be applied, the user may specify the groups for which linking is active. If the user selects checked Group A, in the example of FIG. 16, any changes to the therapy parameter values associated with Group A will be active across the set of linked posture states with regard to the particular posture state (among the linked posture states) that was occupied by the patient when the change was made. This is because Group A is considered to be linking-active. However, if the user selects unchecked Group B and makes a change to a therapy parameter value in Group B while residing in a given posture state, that change will not be effective for the other posture states in the set of linked postures states, because linking is not activated for Group B. i.e., Group B is linking-inactive. In this case, Group B may be selected for different posture states within the set of linked posture states, but changes will only apply for the given posture state occupied by the patient when the change is made. Hence, selection of groups to link specify those groups for which linking will be given effect among the linked posture states. Again, if a particular group is selected for one posture state, and the selected group is not link-active, then any therapy parameter changes made to that group for the one posture state will not be applied for the other posture states.

FIG. 16 illustrates linking of posture states on a selective basis and selection of program groups for which linking will be active, i.e., program groups for which linked posture states will share the same therapy parameter values and changes. Patient programmer 30 and/or clinician programmer 60 may allow linking of posture states and selection of program groups for which linking will be active. In general, selection of linked posture states and link-active program groups may be significant for purposes of initially programming therapies for different posture states, adjusting such therapies dynamically during trial or chronic usage by the patient, and then transitioning among different therapies during operation of posture-responsive therapy control.

In particular, the IMD is configured to select groups, programs within groups, or therapy parameter values for the programs when a patient transitions from one posture state to another posture state. The selection is based on the particular groups, programs and therapy parameter values specified for each posture state. The particular groups, programs and therapy parameter values specified for each posture state can be selected individually or, as described with reference to FIG. 16, by linking posture states. Hence, the linking and link-active group selection determines the changes (or lack of changes) made by the IMD for each posture state when a posture state change is detected.

Once a user such as a clinician or patient has specified linking and link-active groups for an IMD, the IMD may thereafter function according to those specifications. For example, when the IMD detects a transition from a first linked posture state to a second linked posture state, and determines that the current Group is linking-active, the IMD does not change therapy because the posture states are linked and should receive the same therapy, assuming selection of a linking-active group. If the IMD detects a transition between previous and current posture states that are not linked with one another, however, the IMD may adjust therapy according to the therapy parameter values specified for the current posture state.

Linking posture states may enhance the efficiency and ease of programming the IMD by a clinician either in-clinic or remotely. The clinician may quickly propagate changes among linked posture states with a single change rather than multiple, individual changes. In this manner, the disclosure contemplates, in some embodiments, a system that may permit the granularity to assign individual therapy parameter values, programs and/or groups to individual posture states, but also permit more global or semi-global adjustments when a clinician does not necessarily require fine grain adjustment, but instead may be satisfied with the same therapy for different groups of linked postures states (e.g., all of the lying posture states).

In addition to facilitating programming for multiple posture states, the disclosure contemplates the ability, in some embodiments, to propagate patient therapy parameter value changes among multiple linked posture states. For example, the IMD may be configured to change parameter values based on parameter value adjustments entered manually by a patient during the course of therapy, e.g., amplitude adjustments. In this case, when the patient makes a manual adjustment while occupying a current posture state, that adjustment may be used for all of the posture states linked to the current posture state, provided that the current therapy program group that is being applied has been specified as link-active. As further options, linking and link-active status may be specified by the clinician and statically fixed for use by the IMD, or the patient may be given the opportunity to modify linking and link-active status, e.g., via a patient programmer.

With further reference to FIG. 16, screen 250 also may display programming flags 246 to indicate that recent selections have not been saved. The user may use clear button 242 to clear the selections flagged with programming flags 246 or program button 244 to save the selections flagged with programming flags 246. In order for program button 244 to be enabled, screen 250 may require that at least two posture states from posture state selection list 240 and at least one group from group selection list 238 be selected.

Figure 17A:
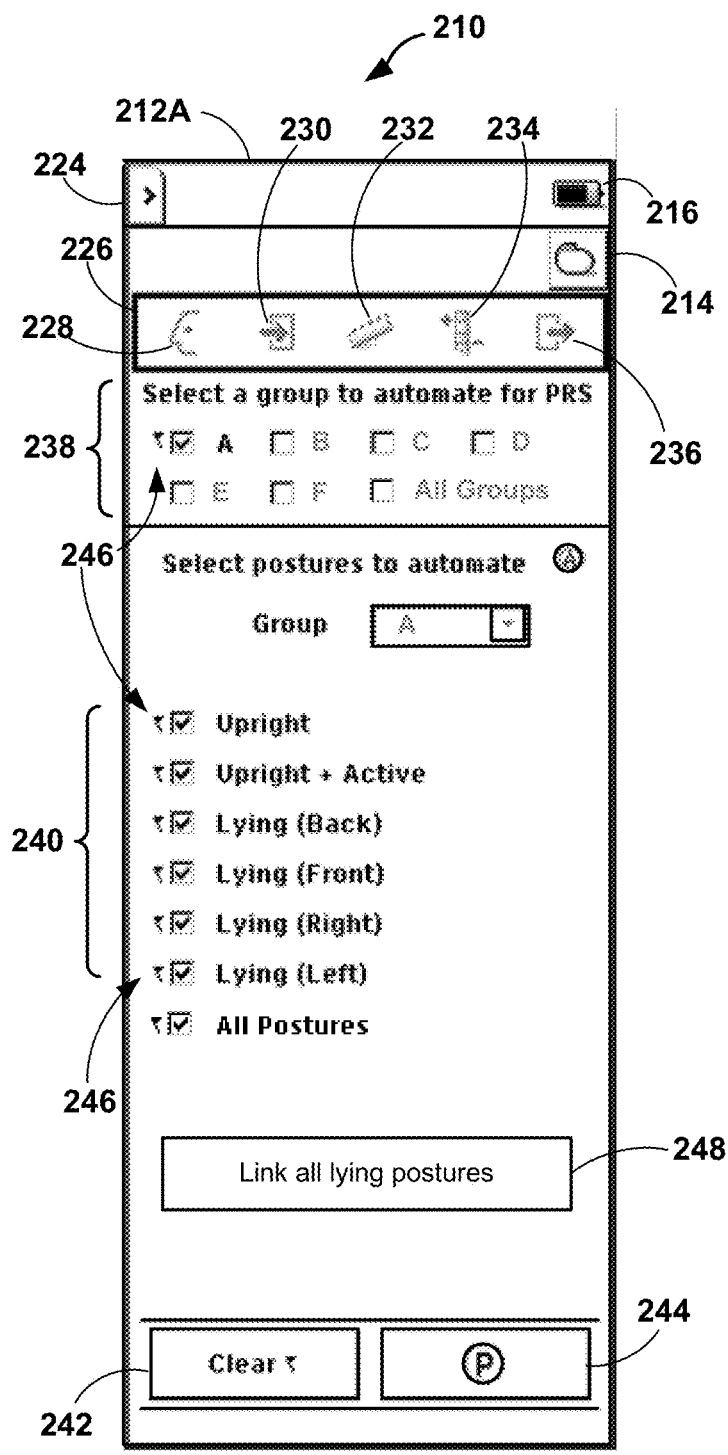
FIGS. 17A-17C are conceptual diagrams illustrating example screens that may be displayed by a user interface of a clinician programmer to allow a user to select which program groups to apply for posture-responsive therapy.
Figure 17B:
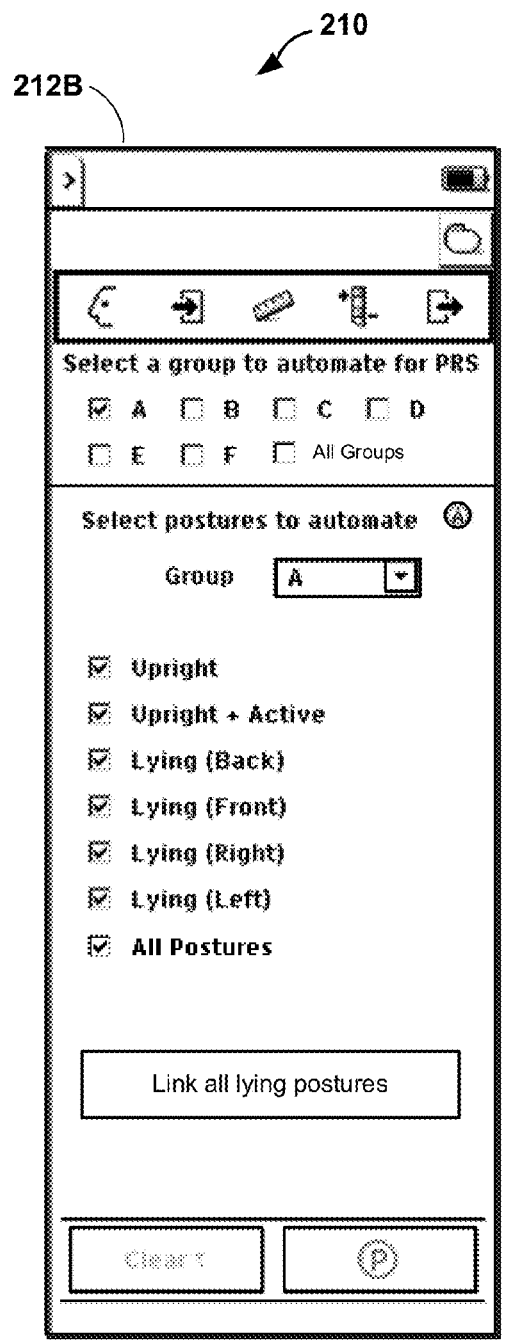
Figure 17C:
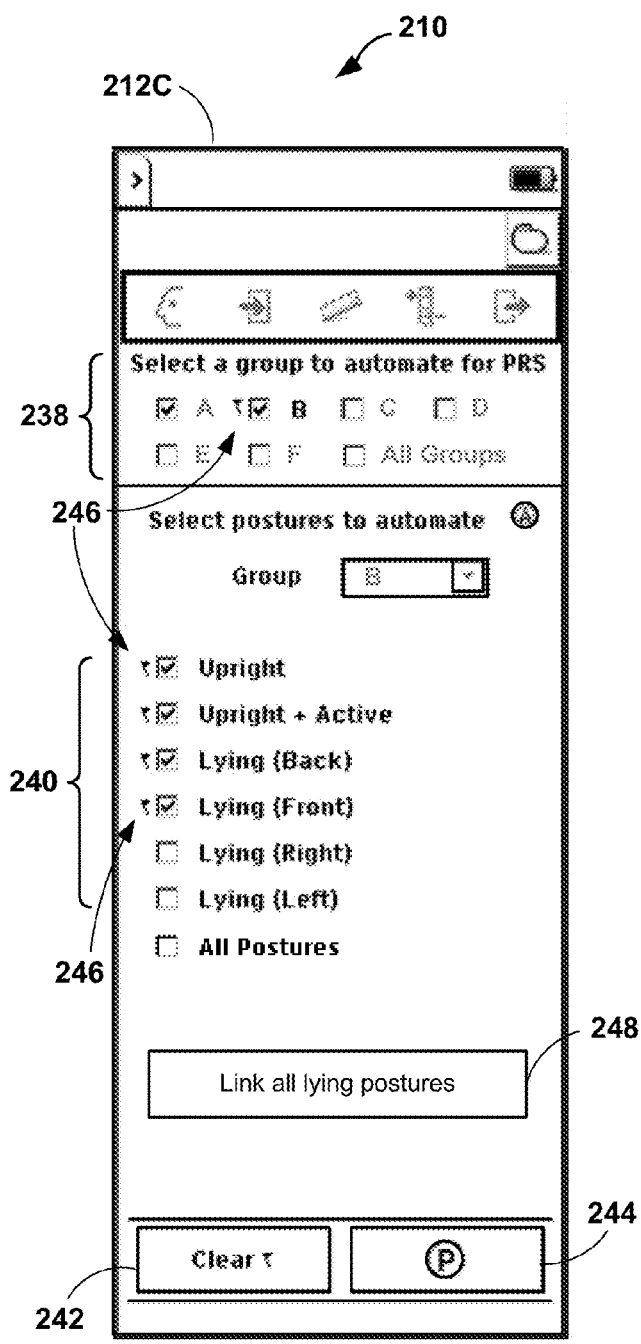

FIGS. 17A-17C are conceptual diagrams illustrating an example user interface 210 of clinician programmer 60 for displaying therapy information that includes posture information to a user, such as a clinician. In the example of FIGS. 17A-17C, display 64 of clinician programmer 60 provides screens 212A-212C, respectively, (collectively "screens 212") to the user via user interface 210. Screens 212 permit a user to select which program groups to apply posture-responsive therapy. Other examples of screens 212 may provide more or less information to the user.

As illustrated in FIG. 17A, a user such as a clinician or patient may select one or more groups for posture-responsive therapy via group selection list 238. Group selection list 238 may include an "All Groups" listing that permits a user to simultaneously select all of the program groups. The "All Groups" listing may be selected if a user would like to select all of the program groups for posture-responsive therapy and apply posture-responsive therapy to the same posture states for each of the program groups.

In the example of FIG. 17A, a user has selected group "A" for posture-responsive therapy. As previously described, the selection of a group may be indicated by displaying a check mark in the box next to the group name. Boxes without check marks are displayed next to unselected groups. If a group is selected for posture-responsive therapy, the IMD automates selection of different therapy parameter values for the group when the patient transitions between different posture states. If a group is not selected for posture-responsive therapy, then the IMD does not automatically select different therapy parameter values based on changes in the detected posture state.

Upon selection of a group for posture-responsive therapy via group selection list 238, a user may select which posture states to apply posture-responsive therapy to for the selected group (e.g., "A" in the example of FIG. 17A) via posture state selection list 240. When a user selects a group for posture-responsive therapy, all posture states for which the group is applied may be selected for posture-responsive therapy by default. If the entire list of posture states is selected by default, the user may unselect any posture states for which he would not like to implement posture-responsive therapy via posture state selection list 240. Alternatively, the user may be required to actively select each of the desired posture states to which posture-responsive therapy will be applied using posture state selection list 240. In the example of FIG. 17A, posture state selection list includes an "All Postures" listing that may allow a user to select all of the posture states simultaneously.

If one or more posture states are linked together for the selected group, unselecting or selecting one posture state of the set of linked posture states may automatically unselect or select the additional posture states of the set. For example, if "Lying (Back)" and "Lying (Front)" are linked and the selected group (e.g., "A" in FIG. 17A) is link-active, then selecting or deselecting the "Lying (Front)" posture state results in selection or deselection of the "Lying (Back)" posture state. In this manner, all the posture states of a set of linked posture states may either be selected or unselected for posture-responsive therapy together rather than individually.

In the example of FIG. 17A, screen 212A includes "Link all lying postures" button 248. "Link all lying postures" button 248 may allow a user to link the lying posture states (e.g., "Lying (Back)", "Lying (Front)", "Lying (Right)", and "Lying (Left)") for the selected group (e.g., "A" in FIG. 17A) without navigating to a separate screen (e.g., screen 250 of FIG. 16). In this manner, the lying posture states may be conveniently and efficiently linked together so that there is no need to enter separate therapy parameter values and/or adjustments for each lying posture state. This may be particularly beneficial when one set of therapy parameter values may provide efficacious therapy to patient 12 when patient 12 is positioned in any of the four lying posture states.

Screen 212A may display programming flags 246 to indicate that recent selections have not been saved. The user may use clear button 242 to clear the selections flagged with programming flags 246 or program button 244 to save the selections flagged with programming flags 246. In order for program button 244 to be enabled, screen 212A may require that at least one posture state from posture state selection list 240 be selected for the selected program group. FIG. 17B illustrates screen 212B, which is displayed after the user has saved the selections illustrated in FIG. 17A using program button 244. As illustrated in FIG. 17B, screen 212B no longer displays programming flags 246.

In the example of FIG. 17C, a user has selected to apply posture-responsive therapy for group "B" via group selection list 238 of screen 212C. Additionally, the user has specified a subset of the posture states displayed via posture state selection list 240 for posture-responsive therapy. As described previously, if all posture states within a group are selected for posture-responsive therapy by default, when a user selects a group for posture-responsive therapy, the user may unselect any posture states for which he would not like to implement posture-responsive therapy for the selected group via posture state selection list 240. Alternatively, the user may be required to select the desired posture states for posture-responsive therapy using posture state selection list 240. As another alternative, as illustrated in FIGS. 17A-17C, posture state selection list 240 may include an "All Postures" listing. A user may use the "All Postures" listing to select all of the posture states and, if applicable, unselect any undesired posture states. If one or more posture states are linked together for the selected group, unselecting or selecting one posture state of the set of linked posture states may automatically unselect or select the additional posture states of the set of linked posture states.

As shown in FIGS. 17A-17C, a user such as a clinician or patient may selectively define the program groups for which posture responsive therapy is to be performed by the IMD ("Select a group to automate") and, for each group, selectively define the posture states to which posture responsive therapy will be applied ("Select postures to automate"). Again, a program group may refer to a set of one or more programs that are delivered simultaneously or on a time-interleaved or ordered basis by the IMD, and each program defines a set of therapy parameter values, where the therapy parameter values for each program may include voltage or current amplitude, pulse width, pulse rate, and electrode configuration (e.g., electrode combination and polarities).

Also, posture responsive therapy generally refers to a mode in which the IMD automatically or semi-automatically adjusts therapy parameter values according to the posture states occupied by a patient, such that different therapy parameter values may be applied for different posture states, and where the adjustment of therapy parameter values may be specified by selection or modification of individual therapy parameter values, programs and/or groups. FIGS. 17A-17C and the description above generally describe techniques for effective management of different groups and posture states to which patient responsive therapy may be applied, in order to facilitate programming by a clinician or patient.

FIGS. 18A-18D are conceptual diagrams illustrating example screens that may be displayed by user interface 210 of clinician programmer 60 to present posture information to a user, such as a clinician. In the example of FIGS. 18A-18D, display 64 of clinician programmer 60 provides screens 260A-260D, respectively, (collectively "screens 260") to the user via user interface 210. Screens 260 include group tab 262, program tabs 264, group selection menu 266, posture state selection menu 268, delete group button 270, save current settings to button 272, and activate therapy button 274. Additionally, for each program of the selected group, screens 260 include a program on/off icon 276, program on/off check box 278, program name text 280, pulse width text 282, pulse rate text 284, electrode configuration icon 286, decrease amplitude button 288, amplitude text 289, and increase amplitude button 290. Other examples of screens 260 may provide more or less information to the user.

In some embodiments, an auto-repeat feature may be implemented for decrease amplitude button 288 and increase amplitude button 290 such that the amplitude is decreased or increased accordingly as long as decrease button 288 or increase button 290 is held down. Additionally or alternatively, a scroll wheel may be provided to adjust amplitude. For example, upon clicking on amplitude text 289, a scroll wheel may then be used to perform amplitude adjustment.

Figure 18A:
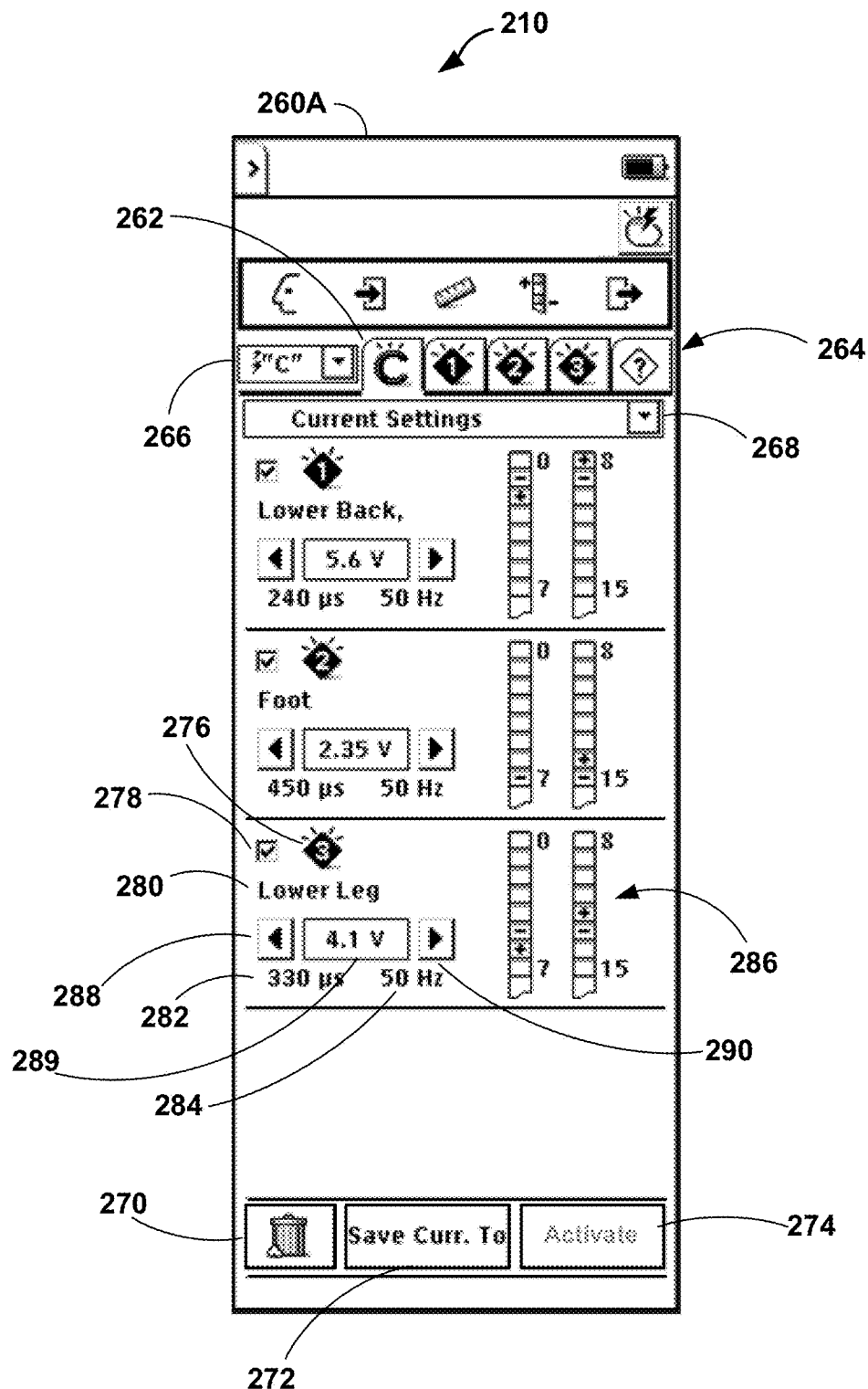
FIGS. 18A-18D are conceptual diagrams illustrating example screens that may be displayed by a user interface of a clinician programmer to present therapy information for various posture states to a user, such as a clinician.

In the example of FIG. 18A, group "C" is activated and the current therapy settings delivered by the IMD (or to be delivered by the IMD) are displayed. Group selection menu 266 indicates that group "C" is displayed. Additionally, the quotation marks around group "C" on group selection menu 266 indicate that group "C" is activated, i.e., is actively being delivered by the IMD. If group "C" were not activated, the quotation marks would not be displayed. Also, program on/off icons 276 indicate that the displayed programs (1, 2, 3) forming part of group "C" and their respective therapy parameters, e.g., displayed via pulse width text 282, pulse rate text 284, electrode configuration icon 286, and amplitude text 289, are activated. The individual programs 1, 2, 3 of group "C", in this example, address pain symptoms associated with the lower back, foot and lower leg.

When the displayed therapy parameters are active, program on/off icons 276 are bolded. In contrast, when the displayed therapy parameters are not activated, program on/off icons 276 are not bolded. Additionally, program on/off check boxes 278 may only be displayed when the displayed program group is activated. Program on/off check boxes 278 may be used to turn an individual program within a group on and off when the program group is activated. As an additional indicator, activate therapy button 274 is disabled when the displayed group is already activated for therapy delivery.

When the therapy parameters displayed for a program are activated, a user such as a clinician or patient may decrease or increase the amplitude of stimulation for that program, e.g., using buttons 288 and 290, respectively. Additionally, the user may navigate to individual program screens for each program via program tabs 264 to adjust other therapy parameter values. A user may also turn individual programs within the selected group on and off using program on/off check boxes 278. Disabling one or more programs using program on/off check boxes 278 may allow a user to program posture-responsive therapy at the program level rather than the group level. As will be described in further detail below, the current stimulation settings may be saved to any of the posture states selected for posture-responsive stimulation via save current settings to button 272.

Figures 18B, 18C:
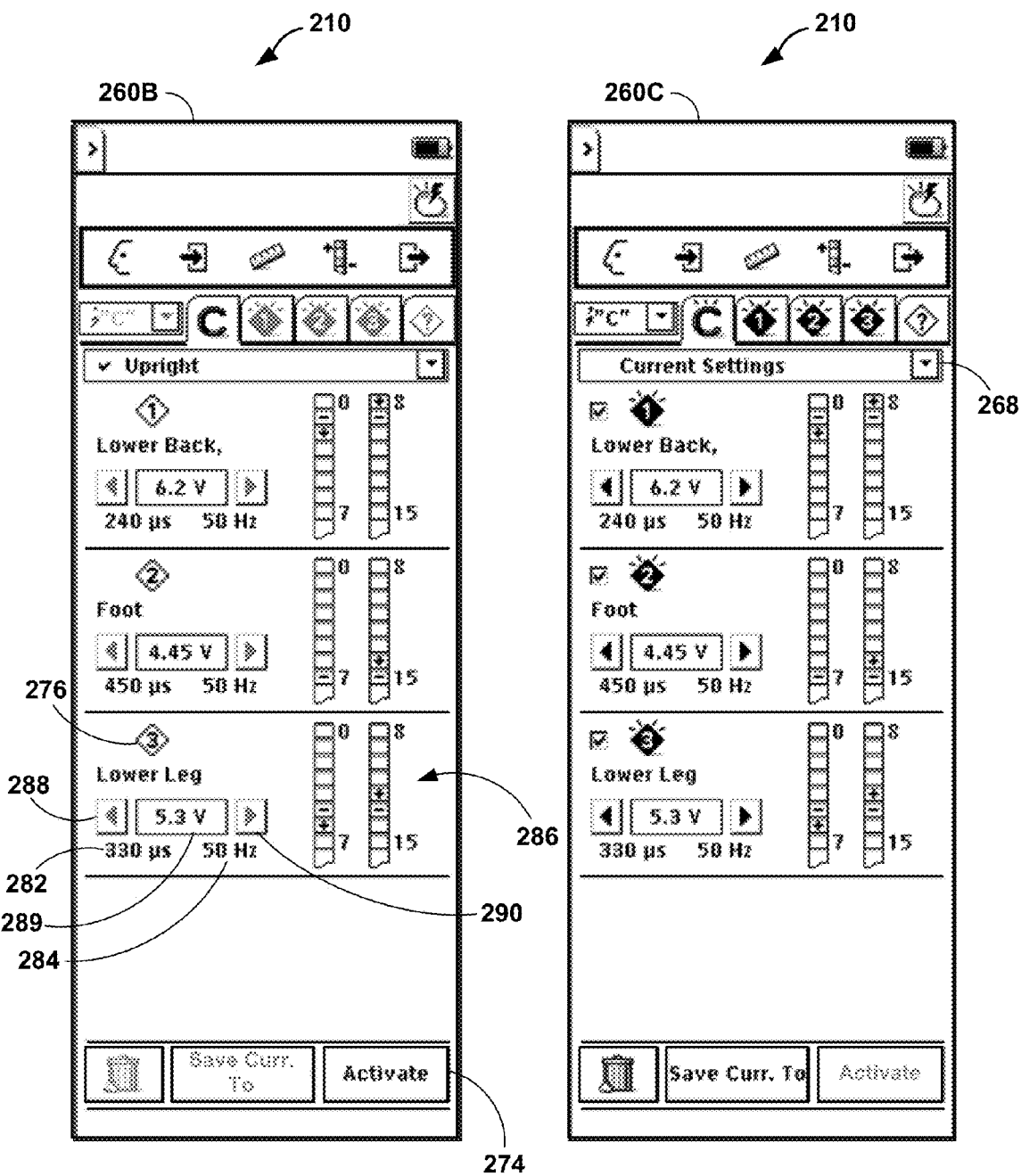

A user may navigate from screen 260A of FIG. 18A to screen 260B of FIG. 18B by selecting the upright posture state from posture state selection menu 268. Posture state selection menu 268 may only allow selection of posture states that have been selected for posture-responsive therapy. Screen 260B illustrates the therapy settings associated with the upright posture state, including the amplitude values. In the example of FIG. 18B, the upright settings are not active. Therefore, the user may not be permitted to decrease or increase the stimulation amplitude, e.g., via buttons 288 and 290. The user may only be allowed to change the therapy settings of programs that are activated, i.e., are actively being delivered by the IMD.

As described previously, program on/off icons 276 indicate whether the programs and their displayed therapy parameters, e.g., displayed via pulse width text 282, pulse width text 284, electrode configuration icon 286, and amplitude text 289, are activated. In the example of FIG. 18B, program on/off icons 276 are not bolded. Therefore, the displayed therapy parameters are not activated. As another indicator, activate therapy button 274 is enabled, suggesting that the displayed program group is not in use to deliver therapy. A user may transition from screen 260B of FIG. 18B to screen 260C of FIG. 18C by activating the program group associated with the upright posture state using activate therapy button 274.

Figure 18D:
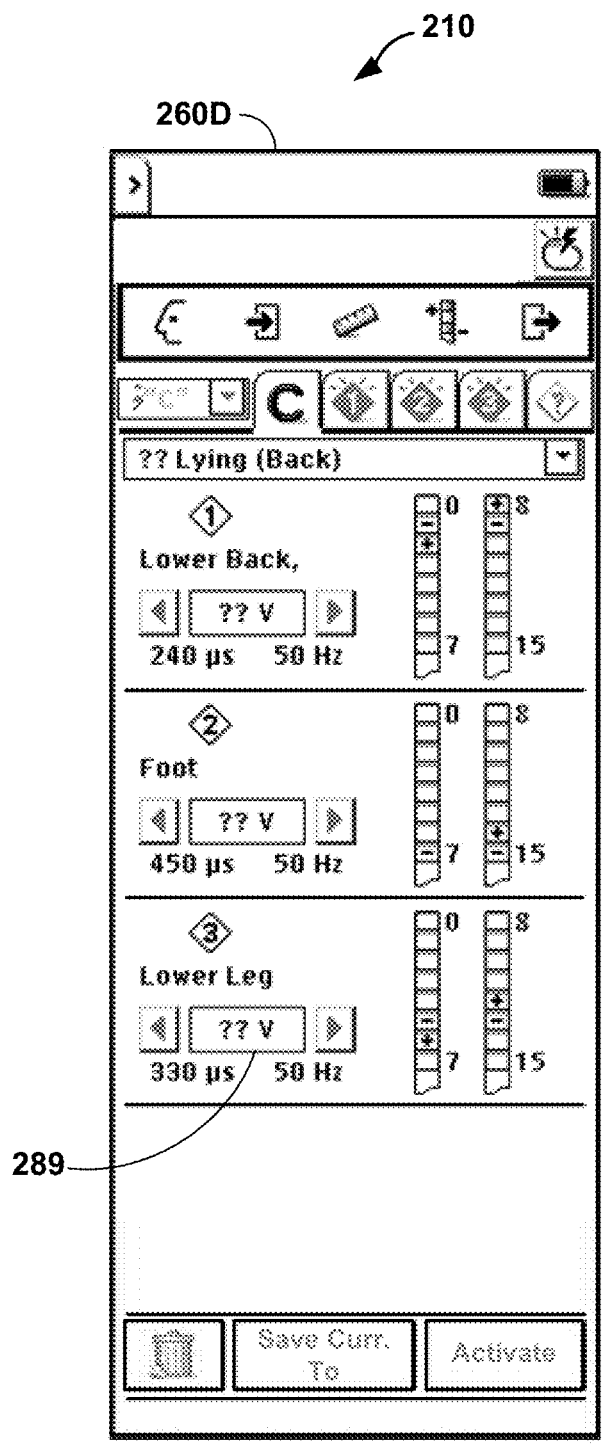

Additionally, a user may navigate from screen 260C of FIG. 18C to screen 260D of FIG. 18D by selecting the lying back posture state from posture state selection menu 268. As previously stated, posture state selection menu 268 may only permit selection of posture states that have been selected for posture-responsive therapy. In the example of FIG. 18D, screen 260D displays question marks (?) for the amplitude values in amplitude text 289, because the amplitudes have not been defined for this particular posture state. In some cases, the clinician or other user of clinician programmer 60 may leave one or more therapy parameter values for the patient to define. In this manner, the posture state may be selected for posture-responsive therapy but not have a complete set of therapy parameter values associated with it. In some cases, the clinician or other user of clinician programmer 60 may leave all of the therapy parameter values for the patient to define. In other cases, the clinician or other user of clinician programmer 60 may define a complete set of therapy parameter values such that all of the therapy parameter values are at least initially clinician-defined.

In the example of FIG. 18D, the amplitude value is undefined for the lying back posture state. When patient 12 first enters the lying back posture state, he may continue to receive the set of therapy parameter values that he was previously receiving, such as the set of therapy parameter values associated with the posture state in which he previously resided. For example, if patient 12 enters the lying back posture state from the upright posture state, and the upright posture state has an associated set of therapy parameter values, patient 12 may receive the therapy parameter values associated with the upright posture. When patient 12 makes an adjustment to the amplitude value for the lying back posture state, e.g., when patient 12 is in the lying back posture state or is transitioning to the lying back posture state, the adjusted amplitude value may be associated with the lying back posture state. As described previously with respect to FIGS. 9-13, the association may be subject to search and stability periods to ensure that the adjustment is associated with the intended posture state. For example, when patient 12 adjusts a value of a therapy parameter that is undefined for the posture state in which he is positioned or to which he is transitioning, the adjusted value of the therapy parameter value may be automatically associated with the appropriate posture state using the techniques described with respect to FIGS. 9-13, e.g., for purposes of posture responsive therapy. Upon subsequent detection of the lying back posture state, patient 12 will receive therapy according to the amplitude and other therapy parameter values associated with the lying back posture state. By allowing patient 12 to define one or more therapy parameter values, the amount of programming time required by the clinician may be decreased.

When one or more therapy parameters for a posture state are undefined and patient 12 first enters the posture state, patient 12 may continue to receive therapy according to the set of therapy parameter values that he was receiving prior to entering the posture state. As another example, if some therapy parameter values are defined and others are undefined for the posture state, patient 12 may receive therapy using a combination of the defined therapy parameter values associated with the posture state and therapy parameter values that he was receiving prior to entering the posture state for the therapy parameters that are undefined. In the example of FIG. 18D where only the amplitude value is undefined, patient 12 may receive therapy using the therapy parameter values associated with the lying back posture state and an amplitude value that was used to deliver therapy before patient 12 entered the posture state. An amplitude or other therapy parameter value may be undefined when a clinician or patient has not previously specified a value for the parameter. In some cases, one or more therapy parameter values may be left undefined, at least initially when patient 12 begins to receive posture state-responsive therapy.

When patient 12 adjusts a value of a therapy parameter that is undefined for the posture state that he is positioned in or transitioning to, the adjusted value of the therapy parameter value may be automatically associated with the posture state, e.g., for purposes of posture responsive therapy. For example, if patient 12 specifies a voltage amplitude of 5.0 volts for a voltage parameter that was previously undefined for the posture state, the voltage amplitude specified by patient 12 will then be used as the voltage amplitude for the posture state. In this case, when the patient 12 occupies the posture state again in the future, the IMD may select therapy parameter values including the adjusted therapy parameter value that was specified by the user when the value was undefined. In effect, the therapy parameter value is no longer undefined. Rather, the value of the therapy parameter adjustment specified by the patient 12 is used to define the previously undefined therapy parameter value. Alternatively, in response to receiving the adjustment from patient 12, patient programmer 30 may request that patient 12 indicate whether to associate the adjusted value with the posture state, i.e., obtain patient approval or confirmation prior to giving effect to the adjustment by associating it with the posture state to define the previously undefined therapy parameter value for the posture state.

As yet another alternative, once patient 12 adjusts one or more of the therapy parameter values as desired for the posture state, patient 12 may be permitted to associate the therapy parameter values for the posture state with one or more other posture states using patient programmer 30. In some embodiments, patient 12 may be permitted to associate a current therapy parameter value or set of a therapy parameter values with a posture state regardless of whether the patient is actually positioned in that posture state. In particular, patient 12 may be permitted to associate a current therapy parameter value for a currently occupied posture state with another posture state that is different from the currently occupied posture state.

In this manner, patient 12 may define one or more therapy parameter values for another posture state without actually occupying that other posture state. The therapy parameter values may replace previously defined therapy parameter values for the other posture state or previously undefined therapy parameter values for the other posture state. The patient 12 may, in some implementations, associate one or more selected therapy parameter values, currently being applied to the current posture state, to the other posture state or multiple posture states, or associate all of the selected therapy parameter values for the current posture state. For example, a user may wish to associate only a voltage amplitude value from the current posture state to a different posture state or states.

Figure 19:
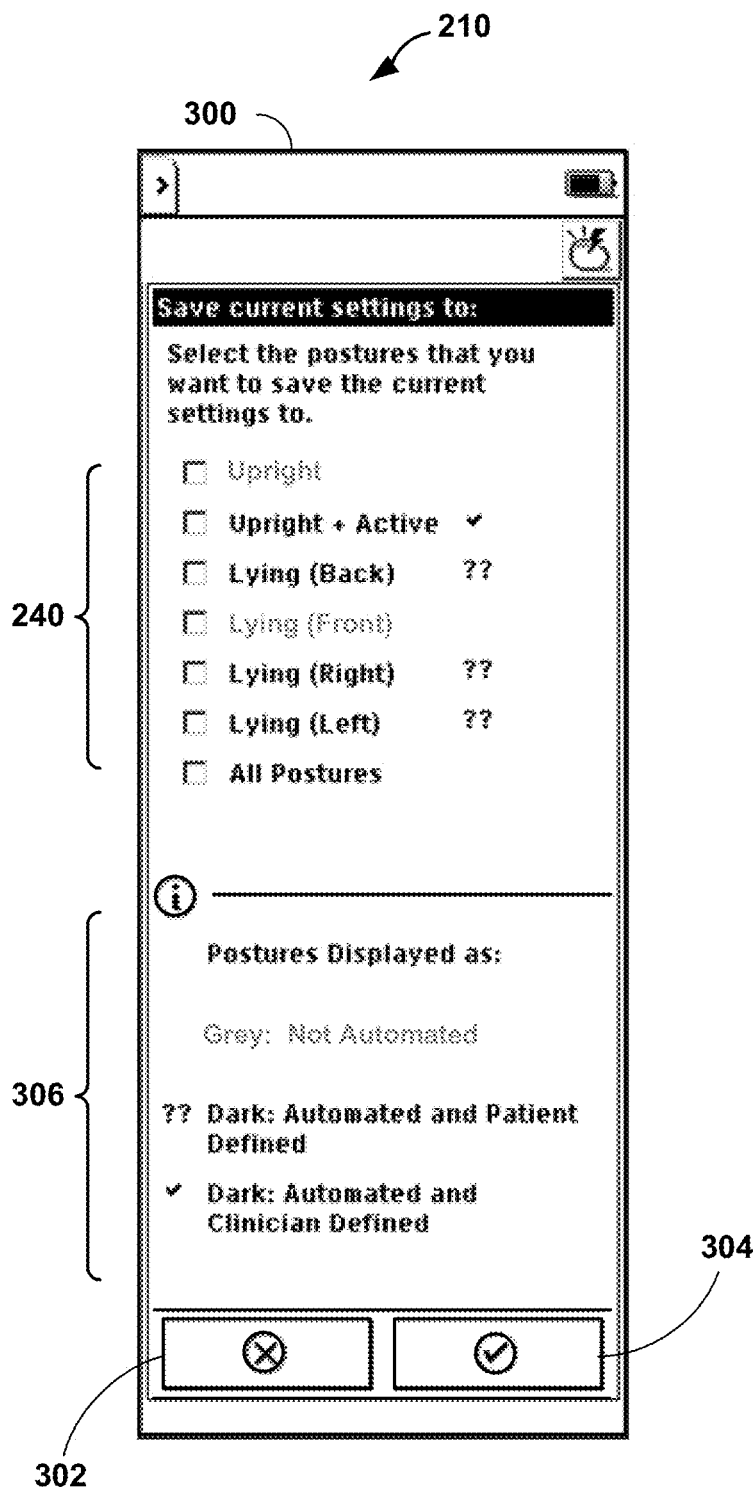
FIG. 19 is a conceptual diagram illustrating an example screen that may be displayed by a user interface of a clinician programmer to allow a user to save the current therapy settings to one or more posture states.

FIG. 19 is a conceptual diagram illustrating an example screen 300 that may be displayed by user interface 210 of clinician programmer 60 to present posture information to a user, such as a clinician. In the example of FIG. 19, display 64 of clinician programmer 60 provides screen 300 to the user via user interface 210. Other examples of screen 300 may provide more or less information to the user.

Screen 300 of FIG. 19 may be displayed when the user selects to save the current therapy settings to a different posture state via save current settings to button 272 of FIGS. 18A-18D. The current therapy settings may include the therapy parameter values presently selected or presently being applied to the patient for the current posture state. For example, when a program group is activated to deliver therapy for a current posture state, the user may select to save the current therapy settings from the group to one or more other posture states in which the patient 12 is not presently residing. The patient 12 may associate or save the current therapy settings to one or more other posture states via save current settings to button 272 (FIG. 18A). In response to actuation of save current settings to button 272, screen 300 may display posture state selection list 240. A user may select which posture states to save the current therapy settings to using posture state selection list 240. Posture state selection list 240 may include an "All Postures" listing, which may permit a user to select all of the postures states automated for posture-responsive therapy to be selected simultaneously.

Saving the current therapy settings to multiple posture states selected for posture-responsive stimulation may provide an initial starting point for therapy delivery for each of the posture states and decrease initial programming time. Once therapy settings are specified for a current posture state, the patient 12 may feel comfortable using the same therapy settings as a starting point for further refinement for other posture states, and possibly all posture states. Some therapy parameter values may be known by the clinician to be safe for any posture state, and therefore can be associated with one or more posture states regardless of whether these parameters are currently being, or ever were previously, used to deliver therapy. Therapy settings may be further refined during chronic use for each of the posture states to obtain acceptable or optimal therapy parameter values for each posture state.

For example, as a patient makes therapy adjustments during chronic use, different therapy settings may be associated with posture states that were initially associated with common therapy settings. Initially, however, associating therapy settings with multiple posture states may provide significant efficiency, possibly decreasing upfront programming time by the clinician while allowing further refinement by the patient 12 as needed. Instead of remaining in the clinic for an extended period of time in order to receive settings for all posture states, the patient 12 may leave with a baseline set of therapy parameter settings that were established for one posture state and then associated with the other posture states. The patient 12 then can experiment with adjustments to the baseline set of therapy parameters. Although therapy parameters can be saved from one posture state to another to define therapy parameters that were previously undefined, the same can be performed to redefine therapy parameters that were previously defined. In some cases, if there are already existing, i.e., previously defined, therapy parameters for a particular posture state, programmer 60 may present a message asking the patient 12 whether they would like to proceed to overwrite the existing therapy parameters for the posture state.

As one example, screen 300 of FIG. 19 may be displayed on clinician programmer 60 to allow the clinician to apply a current therapy parameter value or a set of therapy parameter values to multiple posture states, e.g., as an initial baseline state of therapy parameter values. The current therapy parameter value or set of current therapy parameters may be currently displayed and/or currently delivered to patient 12. For example, the clinician may associate one or more therapy parameter values known to be safe for any posture state with one or more posture states regardless of whether these parameters are currently being, or ever were previously, used to deliver therapy. The associated therapy parameter values then may define the therapy delivered via the multiple posture states. The clinician may associate the parameter values with the multiple posture states during a programming session, e.g., in-clinic or remotely. The patient 12 then can leave the programming session with a baseline set of therapy parameters for some or all of the previously defined posture states. Saving the current therapy settings to multiple posture states selected for posture-responsive stimulation may provide an initial starting point for therapy delivery for each of the posture states and decrease initial clinician programming time. Allowing a clinician to set a baseline therapy, e.g., for multiple posture states, may decrease upfront programming time by the clinician while allowing further refinement by the patient 12 as needed.

Patient 12 may later refine therapy parameter values associated with one or more posture states using patient programmer 30, e.g., in the course of a therapy session. In the therapy session, the IMD 14 or programmer 30 may apply parameter values specified in a previous programming session to deliver therapy to the patient 12 for different posture states. Although posture states are defined, some parameter values may be undefined for some posture states. A patient 12 may set unique therapy parameter values for a given posture state currently occupied by the patient, e.g., by entering therapy parameter values or making therapy parameter value adjustments. The current posture state may have been initially defined with a baseline therapy or left with at least some parameter values undefined. In some embodiments, patient 12 may be permitted to associate a current therapy parameter value or set of a therapy parameter values applied for the current posture state with a posture state regardless of whether the patient is actually positioned in that posture states. In some cases, patient 12 may associate the current therapy parameter value, used to define delivery of therapy to the patient for the current posture state, with multiple posture states that are different from the posture state presently occupied by the patient. Hence, patient 12 may be permitted to associate a current therapy parameter value for a currently occupied posture state with another posture state that is not currently occupied by the patient and is different from the currently occupied posture state.

For example, patient 12 may adjust one or more therapy parameter values while sitting upright. The therapy adjustments may be associated with the upright posture state, e.g., using association logic or techniques such as the search timer and stability timer. Patient 12 may feel comfortable with the therapy parameter value or values for the current upright posture state, and wish to use or try the same therapy parameter value or values for other posture states. As another example, patient 12 may recognize that he desires a lower amplitude when lying down, e.g., in a sleeping position, than when sitting upright. Patient 12 may decrease the amplitude associated with the upright posture state to a lower amplitude that he would prefer to receive when sleeping and associate that amplitude with one or more lying down posture states, e.g., lying back, lying front, lying left, and lying right. In either case, a patient may associate the current therapy parameter value for the current posture with a different posture state via patient programmer 30. Patient programmer 30 or IMD 14 may then define therapy to be delivered for the different posture state based on the newly associated therapy parameter value or values.

Screen 300 or a modified version of screen 300 may be displayed on patient programmer 30 to permit patient 12 to associate the patient adjustment with a posture state other than the posture state patient 12 currently occupies. This may allow patient 12 to define therapy parameter values for a posture state, e.g., posture or combination of posture and activity, without having to occupy to the posture state. Upon association with a different posture state, the therapy parameter value or values may be used to automatically define therapy to be delivered when the patient later resides in the different posture state. Delivering therapy according to the set of therapy parameters values may provide an indication that the set of therapy parameter values are safe for patient 12. In general, patient 12 may be permitted to freely assign therapy parameter values for a current posture state currently occupied by the patient with other posture states. In some cases, however, such associations may be subject to conditions specified by a clinician, such as therapy parameter value safety margins which may limit the level of the therapy parameter value, e.g., voltage or current amplitude, for some posture states.

With further reference to FIG. 19, when a user selects a posture state, screen 300 displays a check mark in the box next to the name of the posture state within posture state selection list 240. Boxes without check marks are displayed next to unselected posture states. If a set of posture states are linked together, when one posture state of the set of linked posture states is selected, the remaining posture states of the set of linked posture states may be automatically selected. Additionally, screen 300 may only permit selection of posture states that have been selected for posture-responsive therapy. A user may also use cancel button 302 or confirm button 304 to cancel or confirm the selections made via posture state selection list 240 of screen 300.

Screen 300 may also indicate, for the selected group, which posture states have been selected for posture-responsive therapy and/or which posture states are associated with clinician-defined therapy parameter values. In the example of FIG. 19, screen 300 includes a legend 306 that explains symbols and other notations used with posture state selection list 240. A posture state selected for posture-responsive therapy may be designated as automated. In some cases, the programmer may be configured to prohibit overwriting of previously defined therapy parameters using the save feature. For example, a posture state associated with a set of therapy parameter values such that each of the therapy parameters is defined may be designated as clinician-defined. A posture state with one or more therapy parameters that are not associated with a specific value may be designated as patient-defined. Hence, in some implementations, the ability to associate therapy parameter settings from current posture state with other posture states may be limited to therapy parameter values that are previously undefined, or extend to all therapy parameter values.

As described above, screen 300 allows a user to associate therapy parameter values with a posture state without the patient being in that posture state. A user may associate the therapy parameter values currently being used to deliver therapy, e.g., for one posture state, with any one or more of the posture states selected for posture-responsive therapy. Delivering therapy according to the set of therapy parameters values may provide an indication that the set of therapy parameter values are safe for patient 12. Even though patient 12 may not actually be in the posture state that the user associates with the set of therapy parameter values when therapy is delivered, patient 12 has felt the intensity of the therapy parameter values and may feel comfortable applying the same stimulation for other posture states.

In the example illustrated in FIG. 19, a user may save a complete set of therapy parameter values to a posture state such that a value is saved for each therapy parameter, e.g., voltage or current amplitude, pulse width, pulse rate, electrode combination, electrode polarity or the like. In some embodiments, a user may be permitted to save a subset of the therapy parameter values to a posture state. In this manner, some of the therapy parameter values may be defined and others undefined for a posture state. As another example, the clinician or other user of clinician programmer 60 may not save any therapy parameters to a posture state and, instead, allow patient 12 to define all of the therapy parameter values.

Figure 20:
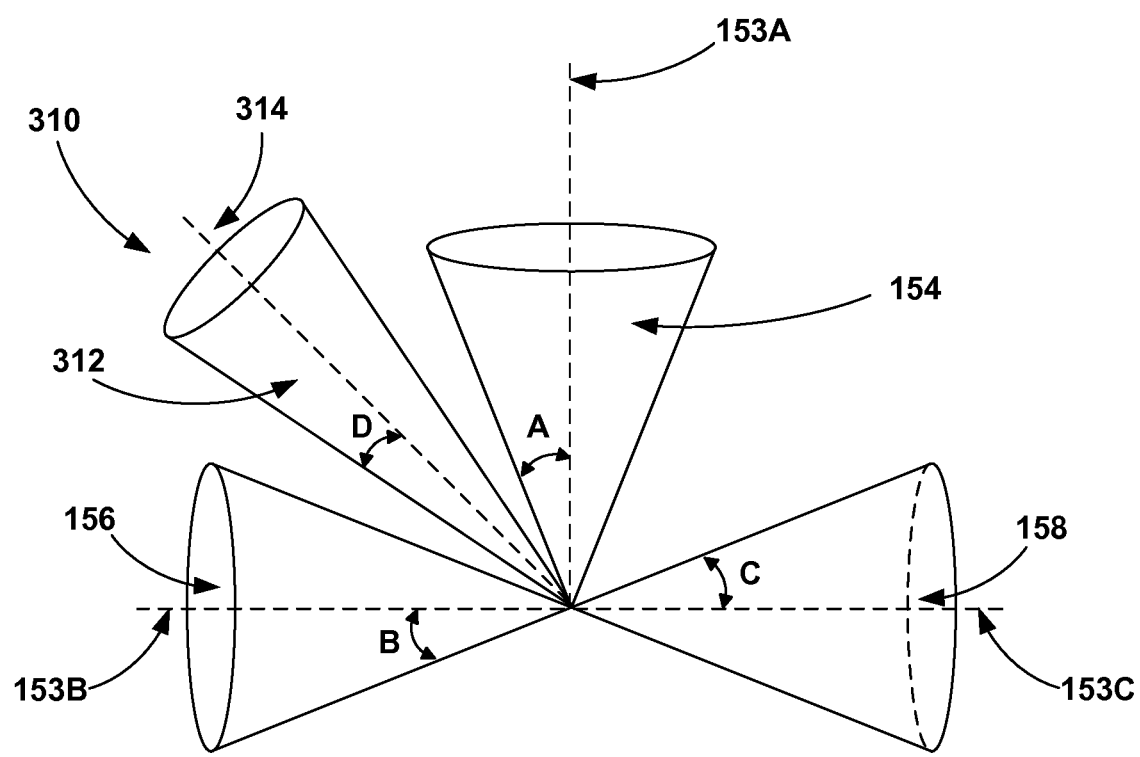
FIG. 20 is a conceptual illustration of posture cones used to define a posture state of a patient via a posture state sensor of a posture state module.

FIG. 20 is a conceptual illustration of posture cones used to define posture states of patient 12 from a posture state sensor of a posture state module, e.g., posture state module 86 of IMD 14 (FIG. 4) or posture state module 98 of IMD 26 (FIG. 5). FIG. 20 illustrates an example posture state space 310 that is a three-dimensional space in which the posture state parameter value from the posture state sensor is placed in relation to posture cones. Posture state space 310 is substantially similar to posture state area 152 of FIG. 8B. However, posture space 310 includes an additional patient-defined posture state. In the example of FIG. 20, the additional patient-defined posture state is a posture cone 312. Similarly to posture state area 152 of FIG. 8B, posture state space 300 includes upright cone 154, lying back cone 156, and lying front cone 158. Posture state space 300 also includes hysteresis zones where no posture cones are defined. In the example of FIG. 20, the hysteresis zones are the spaces not occupied by a posture cone, e.g., upright cones 154, lying back cone 156, lying front cone 158, and patient-defined cone 312.

In the example of FIG. 20, patient-defined cone 312 may be referred to as reclining cone 312, because it is located between upright cone 154 and lying back cone 156 to indicate when patient 12 is reclining back. However, a variety of different posture states may be defined by patient 12. If patient 12 occupies a posture state not contained within the defined posture cones, e.g., upright cone 154, lying back cone 156, and lying front cone 158, patient 12 may create a new cone, such as reclining cone 312. In this manner, patient 12 may supplement a set of pre-established posture states such as a set of pre-established posture state definitions. In this case, the pre-established posture state definitions stored in memory of the programmer are posture state cones, e.g., upright cone 154, lying back cone 156, and lying front cone 158.

User interface 168 of patient programmer 30 may allow patient 12 or another user to submit a request to update the set of pre-established posture state definition, e.g., by adding a new posture state. In response to the request, the programmer updates the set of pre-established posture state definitions. Based on the input from patient 12, a new posture state definition is created, such as reclining cone 312. The patient input may specify the desired location of the new posture cone, e.g., by identifying the location on a graphical representation of posture state space 310 or any other suitable graphical means displayed on patient programmer 30 or providing an indication to patient programmer 30 when patient 12 is in the desired posture state. For example, if patient 12 provides an indication to patient programmer 30 when patient 12 is in the desired posture state, the processor 80 of IMD 14 or a processor of posture state module 86 may determine the output of the posture state module 86 when the indication is received, and capture that information to define the posture state definition. For example, the new posture cone may be created based on that output, which may comprise a sensed coordinate vector.

The cone angle D of reclining cone 312 may be predefined, determined based on an algorithm, or specified by patient 12. As one example, patient programmer 30 may require patient 12 to be positioned in the new posture state, e.g., reclining, when the request for a new posture state is made. Patient programmer 30 may generate reclining cone 312 to extend a predetermined angle from both sides of the patient's position. The patient's position may correspond to center line 314 of reclining cone 312, which may be determined by vector coordinates obtained from a posture state sensor such as an accelerometer.

As another example, patient programmer 30 may compare the requested location of the new cone to the locations of adjacent cones. Patient programmer 30 may calculate cone angle D based on the angle between the adjacent cones 154 and 156 and the desired size of the hysteresis zones between reclining cone 312 and adjacent cones 154 and 156. As yet another example, patient 12 may indicate the boundaries of reclining cone 312. Patient 12 may assume a first position, indicate the first position as the starting point of reclining cone 312 via patient programmer 30, assume a second position, and indicate the second position as the ending point of reclining cone 312 via patient programmer 30.

Alternatively, patient 12 may graphically indicate the boundaries of reclining cone 312 directly on user interface 168 of patient programmer 30. For example, patient 12 could draw a cone or indicate a region of the cone with a stylus or other pointing or drawing tool in conjunction with a touch screen on patient programmer 30. Patient 12 could draw the cone or simply draw a ray to represent a central reference vector of the cone. In this case, programmer 30 could automatically apply a tolerance angle to the reference vector to define the cone. In some cases, patient 12 could identify the tolerance angle. Upon defining the posture state definition, patient 12 could view the result, either as a final result or a preliminary result that requires patient confirmation for execution. In particular, patient programmer 30 may be configured to present an illustration of the cone to the user.

In some examples, using programmer 30, a patient 12 may be permitted to copy and paste an existing cone to create a new cone in a particular region, or drag and drop an existing cone into a particular region. Also, patient programmer 30 may be configured to permit patient to resize existing cones by redefining cone angles or by manipulating one or more handles or other control points on an existing cone or a new cone to expand or shrink the cone or its tolerance angle. As an example, a cone may have control points associated with rays defining the outer surface of the cone, as a function of cone angle.

By dragging the control points with a stylus or other pointing device in a given direction, the patient 12 may increase or reduce the cone tolerance angle. In some cases, a patient 12 may manipulate a control point on one side of the cone to expand or shrink the cone angle in a symmetrical manner about the reference vector. Dragging and dropping, copying and pasting, expanding and shrinking, rotating, tilting, and other graphical utility operations may be used to create new cones, or resize new or existing cones. As an illustration, a patient 12 could click on an upright cone and specify a copy operation, and drag a copy of the cone to a desired location, possibly rotating the cone to a desired position.

As another example, patient programmer 30 may provide a drop down menu that provides numerous graphical operations that can be chosen by a patient 12, such as cone shrinking, cone enlarging, or other operations. In some cases, a drop-down menu may permit a patient to select different cone or cone angle sizes, such as small, medium or large. A variety of graphical utilities may be provided to the patient 12 via patient programmer 30 to permit the patient to flexibly and conveniently customize posture state definitions by modifying existing cones or adding new cones of desired size and position. Although cones are described for purposes of illustration, other types of posture states may be suitable for graphical manipulation and definition by patient 12.

Allowing patient 12 to define posture states may be particularly useful when patient 12 frequently occupies a posture state not contained within a set of clinician-defined cones. Patient 12 may create posture states corresponding to his typical activities, such as sitting, reading, and driving. One or more of the therapy parameter values used to deliver therapy when the new postures state is defined may optionally be associated with the new posture state for posture-responsive therapy, e.g., to provide one or more initial therapy parameter values for the new posture state. The new posture state may be selected for posture-responsive therapy, e.g., automatically in response to creation of the new posture state or manually in response to patient input. In this manner, a set of therapy parameter values may be associated with the new posture state. Upon subsequent detection of the new posture state, therapy may be delivered according to the set of therapy parameter values. Additionally, therapy adjustments made when patient 12 is in or transitioning to the new posture state may be associated with the new posture state.

Patient 12 is not limited to defining posture states outside of the clinician-defined posture states. In some embodiments, patient 12 may be allowed to modify existing posture states. For example, if the therapy parameter values associated with upright cones 154 are being delivered when patient 12 is reclining, patient 12 may modify cone angle A, and/or the location of center line 153A. By allowing patient 12 to modify existing posture state definitions such as existing, pre-established cones, patient 12 may adapt therapy delivery to the changing needs of patient 12. As one example, if the upright posture of patient 12 changes from slouching to more upright over time, allowing patient 12 to adjust existing upright cones 154 may improve therapy delivery to patient 12.

FIG. 20 and its corresponding description refer primarily to posture state cones for purposes of example. However the concept of updating posture state definitions, e.g., by creating new posture states and/or modifying existing posture states, may be applicable to other types of posture state definitions. In this manner, although a center line and cone angle are used to describe posture state cones for purposes of illustration, a posture state may be more generally defined by a posture coordinate vector and a tolerance, which may define the boundaries of a posture state.

In other examples, posture state definitions may be updated automatically by programmer 30, programmer 60 or IMD 14. For example, IMD 14 may record and analyze patient postures and, optionally, therapy adjustment data. The patient postures may be indicated by sensed coordinate vectors received from an accelerometer or other posture sensor of posture state module 86. Based on this data, IMD 14 may automatically update posture state definitions, e.g. by merging, splitting, expanding, shrinking, or creating posture states. Although the techniques for automatically updating posture state definitions described with respect to FIGS. 21-23 primarily refer to IMD 14, such techniques may more generally be performed by IMD 14, IMD 28, or external programmer 20, e.g., patient programmer 30 or clinician programmer 60.

IMD 14 may record and store, e.g., within memory 82, posture vectors or other data indicative of the orientation of patient 12, as an indication of patient postures. IMD 14 may continuously or periodically record the postures of patient 12. As one example, IMD 14 may record the posture vector of patient 12 substantially continuously, e.g., continuously or via periodic sampling, to determine which posture vectors patient 12 frequently occupies. IMD 14 may analyze this information to determine whether any posture state definitions should be updated.

Figure 21:
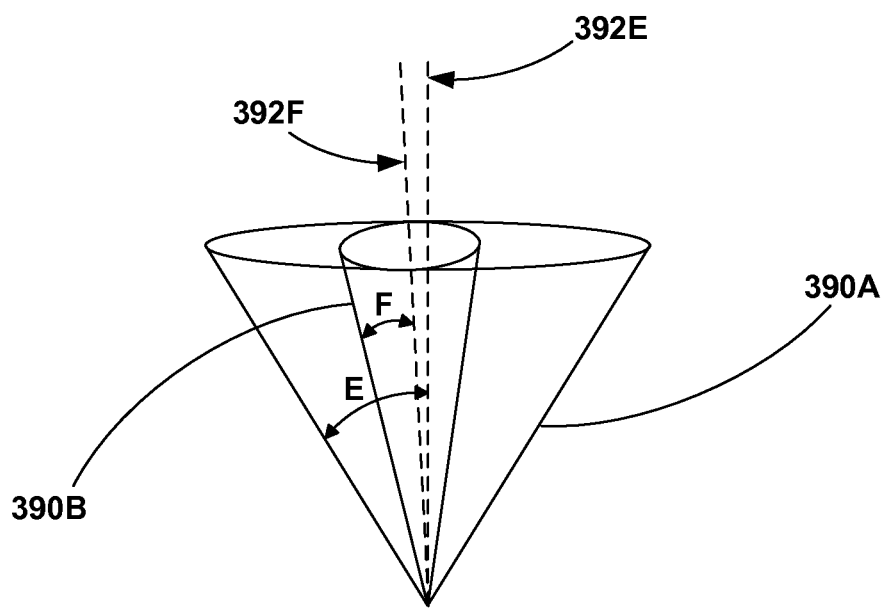
FIG. 21 is a conceptual illustration of a posture cone that is automatically redefined based on recorded posture vectors.

For example, IMD 14 may identify a set of the recorded posture vectors that fall within a defined posture state. If the identified set of the recorded posture vectors predominantly fall within a portion of the defined posture state, as automatically determined by IMD 14, IMD 14 may shrink the posture state definition such that its boundaries more closely match the portion where the posture vectors predominantly fall, e.g., automatically or upon confirmation for a user. As illustrated in the example of FIG. 21, posture state cone 390A may initially be defined by center line 392E, as referred to as posture state reference vector 392E, and cone angle E. However, based on recorded posture vectors over a period of time, IMD 14 may redefine the posture state definition to generate a modified posture state cone 390B defined by center line 392F, also referred to as posture state reference vector 392F, and cone angle F.

Posture state cone 390B may represent the portion of posture state cone 390A where the recorded posture vectors predominantly fall. For example, IMD 14 may automatically define the boundaries of modified posture state cone 390B such that at least a specified percentage, e.g., 80-100%, of the recorded posture vectors for the posture state cone 390A fall within the smaller posture state cone 390B. IMD 14 may be configured to automatically evaluate redefinition of posture state cone 390A on a periodic basis or after a specified number of posture vectors have been received for posture state cone 390A. By shrinking a posture state definition, IMD 14 may make greater use of hysteresis zones between posture state definitions. Although posture state cones are illustrated in the example of FIG. 21, other types of posture state definitions may also be used. In this manner, redefining a boundary of a posture state may more generally comprise redefining a posture state reference vector and/or a tolerance, e.g., a distance, angle, or cosine value.

As another example, IMD 14 may record the orientation of patient 12 each time IMD 14 receives a patient therapy adjustment, e.g., from external programmer 20. For example, IMD 14 may record the posture vector that patient 12 occupies when a therapy adjustment is received and associated with the posture state, e.g., according to association techniques described in this disclosure. The posture vector may be a posture vector that patient 12 occupies when the therapy adjustment is received or a posture vector to which patient 12 transitions following the therapy adjustment. In some examples, more than one posture vector may be recorded for each therapy adjustment. IMD 14 may also record therapy adjustment data. For example, IMD 14 may store, e.g., within memory 82, associations between recorded posture vectors and therapy adjustment data. IMD 14 may analyze the vectors and therapy parameter values associated with therapy adjustments to determine whether to update posture state definitions.

Figure 22:
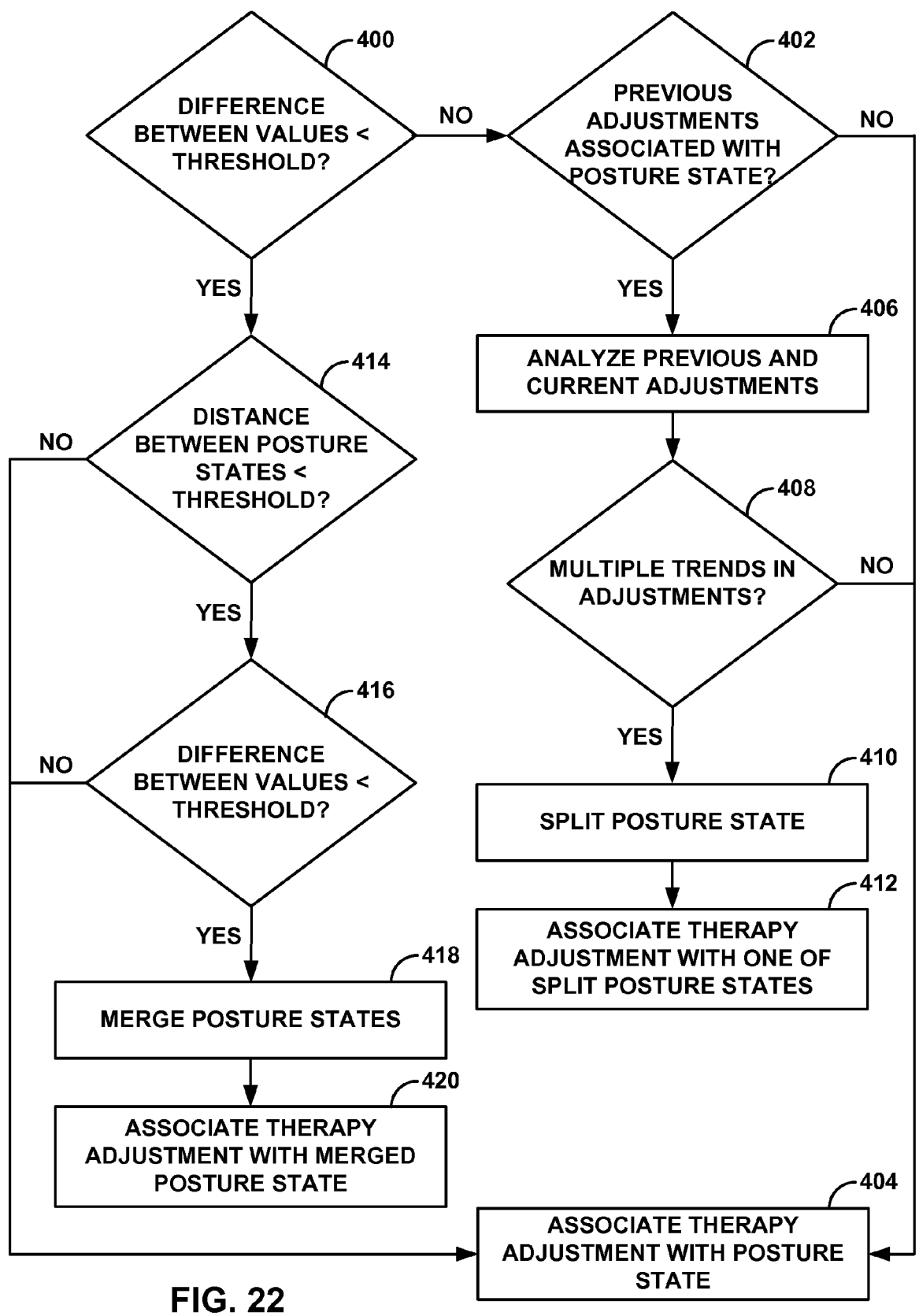
FIG. 22 is a flow diagram illustrating an example method for updating posture state definitions when a recorded posture vector associated with therapy adjustment falls within a defined posture state.
Figure 23:
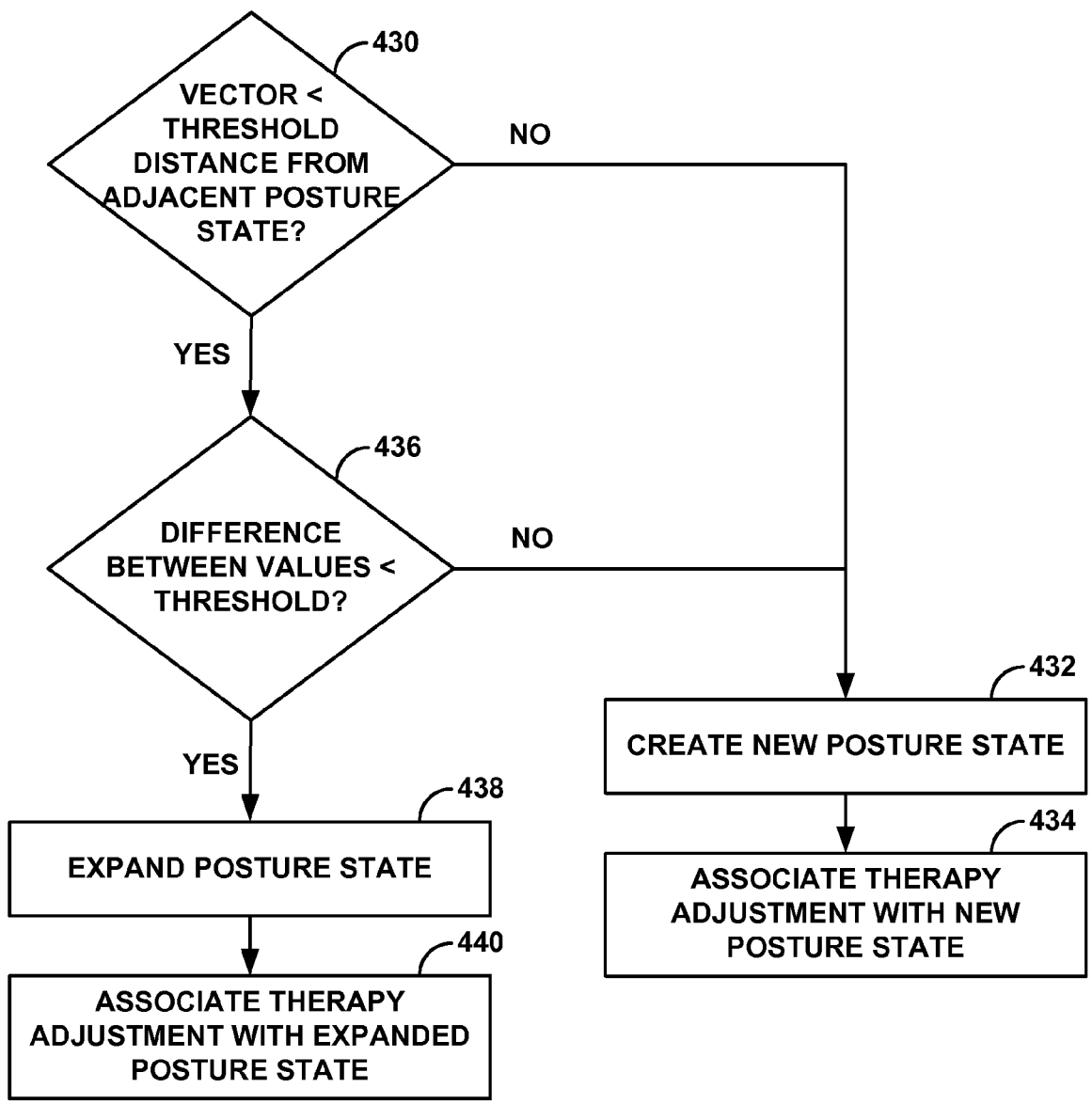
FIG. 23 is a flow diagram illustrating an example method for updating posture state definitions when a recorded posture vector associated with a therapy adjustment falls outside of the defined posture states

FIG. 22 is a flow diagram illustrating an example method for updating posture state definitions when a recorded posture vector associated with a therapy adjustment falls within a defined posture state. Similarly, FIG. 23 is a flow diagram illustrating an example method for updating posture state definitions when a recorded posture vector associated with a therapy adjustment falls outside of the defined posture states. IMD 14 may determine whether a posture vector associated with a therapy adjustment falls within any of the defined posture states.

If IMD 14 determines that a posture vector associated with a therapy adjustment falls within a defined posture state, IMD 14 may determine whether the difference between an adjusted therapy parameter value entered by patient 12 and associated with the posture vector and a therapy parameter value associated with the posture state is less than a threshold difference (400), as illustrated in FIG. 22. By determining whether the difference between an adjusted therapy parameter value associated with the posture vector and a therapy parameter value associated with the posture state is less than a threshold difference, IMD 14 may determine how closely the adjusted therapy parameter value compares to the therapy parameter value associated with the posture state.

In some examples, IMD 14 may compare the difference in the values of one specified therapy parameter, such as amplitude, to a threshold value. In other examples, IMD 14 may compare the difference in the values of each of a plurality of therapy parameters to one or more threshold values. For example, IMD 14 may compare the difference in each therapy parameter value to a respective threshold value and determine that the difference exceeds a threshold difference if the difference in one or more of the individual therapy parameter values exceeds its respective threshold value. As another example, IMD 14 may combine the individual differences of each of the plurality of therapy parameter values, e.g., using a weighted summation, to determine an overall difference in the therapy parameters values. IMD 14 may compare the overall difference to an overall threshold value.

A difference between the therapy parameter values that exceeds the threshold value may signify that the therapy adjustment is substantially different from the therapy parameter values stored in association with the posture state. If the difference exceeds the threshold value, IMD 14 may further examine therapy adjustments associated with posture vectors that fall within the posture state. More specifically, IMD 14 may determine whether any previously received therapy adjustments were associated with posture vectors that fall within the posture state (402).

If there are not any previously received therapy adjustments associated with posture vectors that fall within the posture state, IMD 14 may associate the therapy adjustment with the posture state (404). In this manner, the previously undefined therapy parameter value for the posture state is defined according to the patient therapy adjustment. The therapy parameter values previously associated with the posture state, if available, may have been initial values set during the initial programming of IMD 14. IMD 14 may store the adjusted therapy parameter values and the associated posture vector in association with the posture state.

If there are one or more previously received therapy adjustments associated with posture vectors that fall within the posture state, IMD 14 may analyze the previously and currently received therapy adjustments (406). For example, IMD 14 may analyze where the posture vectors are positioned and the therapy parameter values associated with the posture vectors. For example, IMD 14 may identify two posture vectors separated by a substantial distance with substantially different therapy parameter values.

As another example, IMD 14 may identify a first set of posture vectors associated with similar therapy parameter values concentrated in a first region of the posture state and a second set of posture vectors associated with similar therapy parameter values concentrated in a second region of the posture state. The therapy parameter values associated with the first set of posture vectors may be substantially different from the therapy values associated with the second set of posture vectors.

Based on the analysis, IMD 14 may determine whether the therapy adjustments and corresponding posture state vectors indicate multiple trends in the therapy adjustments (408). For example, IMD 14 may identify different regions of the posture state that exhibit different trends in therapy adjustments. If IMD 14 does not identify different trends in the therapy adjustments, IMD 14 may associate the therapy adjustment with the posture state (404). If IMD 14 identifies different trends in the therapy adjustments, IMD 14 may split the posture state into two or more new posture states according to the identified trends (410). For example, postures initially assigned to a common posture state may be reassigned by splitting such that some of the postures are assigned to one posture state and other postures are assigned to a different posture state. IMD 14 may also associate the current therapy adjustment with the appropriate one of the new posture states (412).

Returning back to determining whether the difference between an adjusted therapy parameter value associated with the posture vector and a therapy parameter value associated with the posture state is less than a threshold difference (400), if IMD 14 determines that the difference is less than a threshold difference, IMD 14 may further examine whether the posture state in which the posture vector falls is similar to any posture states positioned close by. For example, IMD 14 may determine if the distance between the posture state and any of its adjacent posture states is below a threshold distance (414). If none of the adjacent posture states are within a threshold distance of the posture state in which the posture vector lies, IMD 14 may associate the therapy adjustment with the posture state (404).

If one or more of the adjacent posture states are within a threshold distance of the posture state in which the posture vector lies, IMD 14 may determine whether the therapy parameter values associated with the closely located posture states are substantially similar to the adjusted therapy parameter values. More specifically, IMD 14 may determine whether the difference between one or more of the adjusted therapy parameter values and one or more therapy parameter values associated with an adjacent posture state is below a threshold difference (416). If more than one adjacent posture state is within a threshold distance of the posture state in which the posture vector lies, IMD 14 may make a separate determination for each of the adjacent posture states that fall within the threshold distance.

The method of determining whether the difference between one or more of the adjusted therapy parameter values and one or more therapy parameter values associated with an adjacent posture state is below a threshold difference (416) may be substantially similar to the method described with respect to determining whether the difference between an adjusted therapy parameter value associated with the posture vector and a therapy parameter value associated with the posture state is less than a threshold difference (400). For example, IMD 14 may compare values for one or multiple therapy parameters and the threshold value may be specific to a therapy parameter or an overall threshold value.

If none of adjacent posture states within the threshold distance are associated with therapy parameter values substantially similar to the adjusted therapy parameter values, IMD 14 may associate the therapy adjustment with the posture state in which the posture vector lies (404). If one or more of the adjacent posture states within the threshold distance are associated with therapy parameter values substantially similar to the adjusted therapy parameter values, IMD 14 may merge the one or more adjacent postures states that are within the threshold distance and are associated with the substantially similar therapy parameter values with the posture state in which the posture vector lies (418). For example, IMD 14 may merge the one or more adjacent postures by associating them with common, merged posture state. IMD 14 may also associate the adjusted therapy parameter values with the merged posture state (420).

FIG. 23 is a flow diagram illustrating an example method for updating posture state definitions when a recorded posture vector associated with a therapy adjustment falls outside of the defined posture states. IMD 14 may determine whether the posture vector is within a threshold distance of any of the posture states adjacent to the posture vector (430). If none of the existing posture states adjacent to the posture vector are within a threshold distance of the posture vector, IMD 14 may create a new posture state that includes the posture vector (432). For example, IMD 14 may generate the posture state to extend a predetermined amount, e.g., a predetermined angle or distance, from both sides of the posture vector. As another example, IMD 14 may compare the location of the posture vector to the locations of adjacent posture states. IMD 14 may determine the boundaries of the new posture state based on the distance between the posture vector and surrounding posture states and the desired size of the hysteresis zones between posture states. IMD 14 may also associate the therapy adjustment with the new posture state (434).

If the posture vector is within a threshold distance of one or more posture states adjacent to the posture vector, IMD 14 may examine whether any of the posture states within the threshold distance are associated with therapy parameter values similar to the adjusted therapy parameter values. More specifically, IMD 14 may determine whether the difference between an adjusted therapy parameter value associated with the posture vector and a therapy parameter value associated with the posture state that falls within a threshold distance of the posture vector is less than a threshold difference (436). As described with respect to determining whether the difference between an adjusted therapy parameter value associated with the posture vector and a therapy parameter value associated with the posture state is less than a threshold difference (400), IMD 14 may compare values for one or multiple therapy parameters and the threshold value may be specific to a therapy parameter or an overall threshold value.

If none of the posture states within the threshold distance of the posture vector are associated with therapy parameter values substantially similar to the adjusted therapy parameter values, IMD 14 may create a new posture state that includes the posture vector (432) and may also associate the therapy adjustment with the new posture state (434). If a posture state within the threshold distance of the posture vector is associated with therapy parameter values substantially similar to the adjusted therapy parameter values, IMD 14 may expand the boundaries of the posture state to include the posture vector (438). If multiple posture states within the threshold distance of the posture vector are associated with therapy parameter values substantially similar to the adjusted therapy parameter values, IMD 14 may merge the multiple posture states in addition to expanding the boundaries of the posture state to include the posture vector. IMD 14 may also associate the therapy adjustment with the expanded posture state (440).

In summary, as described in this disclosure, various posture state management techniques may be implemented in a clinician programmer, patient programmer and/or IMD to facilitate definition of posture states and associated therapy parameter values for use in posture responsive therapy, i.e., therapy in which therapy parameter values are selected or adjusted according to a detected posture state of a patient.

For example, when there is no defined posture responsive therapy for a given posture state, and a patient makes a therapy adjustment while occupying that posture state, a programmer or IMD may associate the adjustment with the posture state to define the therapy for that posture state such that a therapy parameter value indicated by the adjustment is delivered that next time the patient occupies that posture state. In particular, upon subsequently detecting the posture state, posture responsive therapy is auto-enabled to apply the defined therapy with the associated therapy parameter value. If the patient initially leaves the clinic with posture-responsive therapy non-enabled for some posture states, once the patient makes an adjustment within a posture state, a programmer or IMD may auto-enable that posture state for posture-responsive therapy and return the amplitude to the patient defined value on subsequent returns to that posture state.

In some embodiments, posture states may be linked to tie multiple posture states to common set of posture reference data and a common set of therapy parameter values. This may, in effect, merge multiple posture cones for purposes of posture state-based selection of therapy parameter values. For example, all lying posture state cones (back, front, left, and right) could be treated as one cone or donut/toroid. One program group or common set of therapy parameter values may apply to all posture states in the same merged cone, according to the linking status of the posture states, as directed via a programmer.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the donut or toroid may be divided into sectional segments that correspond to different posture states, such as "Lying (Back)", "Lying (Front)", "Lying (Right)", and "Lying (Left)". In this case, different posture reference data and therapy parameter values may be assigned to the different sectional segments of the donut/toroid.

As an additional feature, a clinician or patient may be permitted, via a clinician and/or patient programmer, to define new posture states that may not be included in an initial set of posture states. If a patient frequently (or not so frequently) occupies an undefined posture state, e.g., reclining, sitting, reading, driving, for example, the clinician or patient may be permitted to assign a specific posture state and associate clinician- or patient-selected therapy parameter values with the newly defined posture state. In effect, a new posture state cone may be dynamically generated based on patient selection of the newly defined posture state.

Additionally or alternatively, an external programmer, e.g., patient or clinician programmer, or an IMD may automatically update posture state definitions. For example, a programmer or IMD may record and analyze patient posture and, optionally, therapy adjustment data. Based on this data, IMD 14 may update posture state definitions, e.g. by merging, splitting, expanding, shrinking, or creating posture states. In this manner, posture state definitions may be dynamic and customizable As a further feature, various therapy parameter values may be initialized or adjusted for different posture states without the patient actually residing in the posture states. For example, a clinician or patient may be permitted to set initial therapy parameter values or override/adjust existing parameter values for some or all posture states without requiring the patient to actually occupy the posture state. A clinician or patient may also be permitted to save therapy settings to multiple posture states at once. In this manner, the clinician or patient may quickly set therapy parameter values to desired values.

Figure 24:
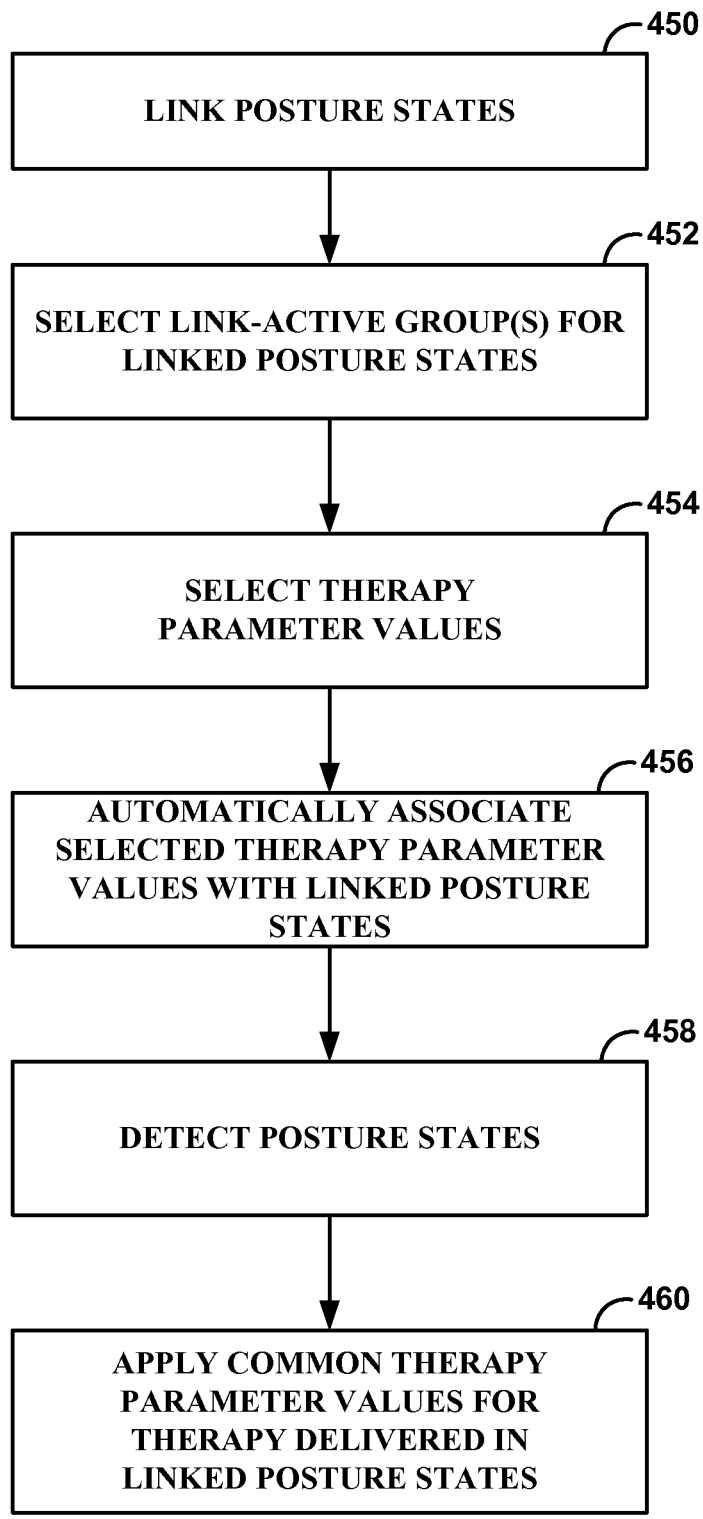
FIGS. 24-26 are flow charts illustrating some of the techniques described in this disclosure.
Figure 25:
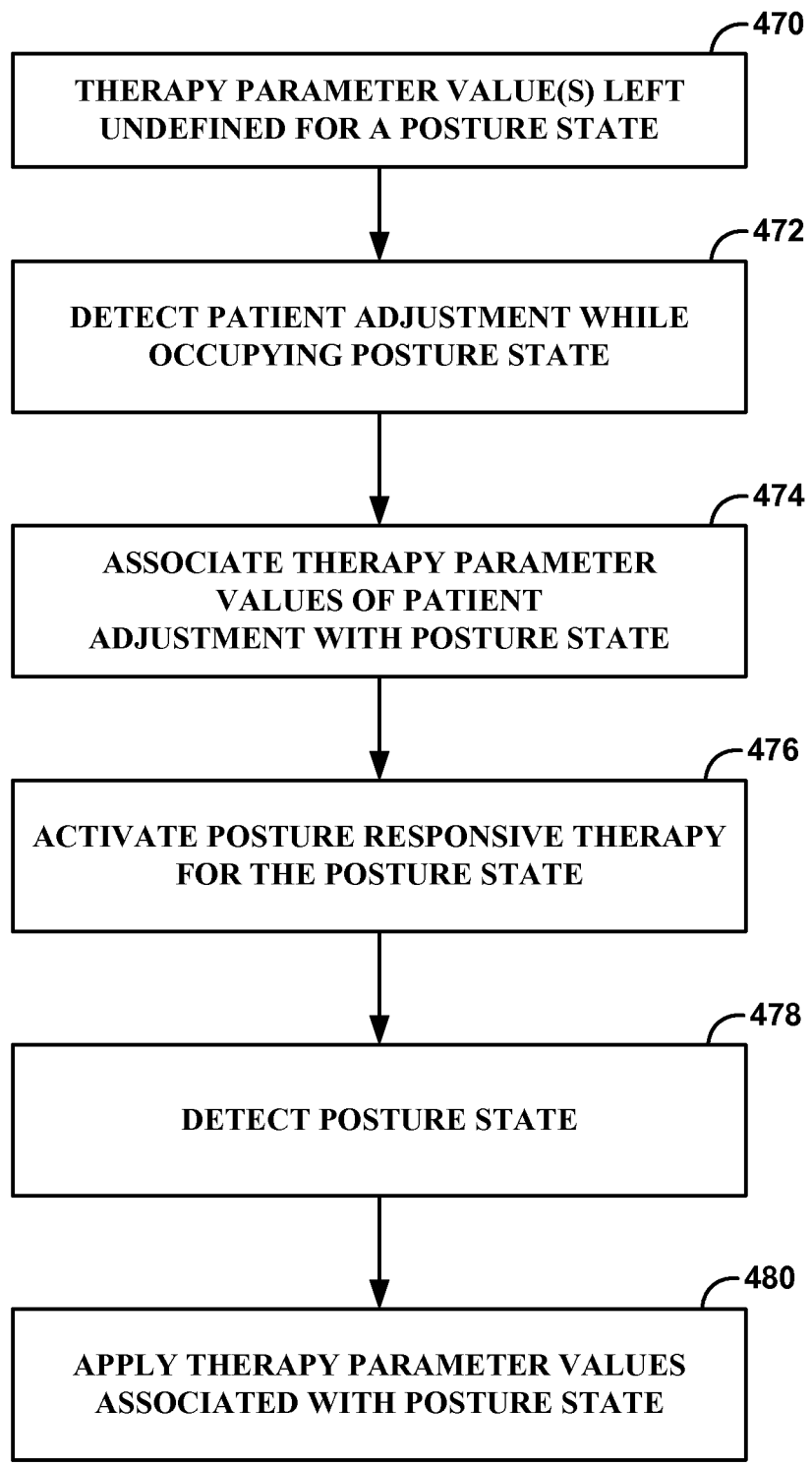
Figure 26:
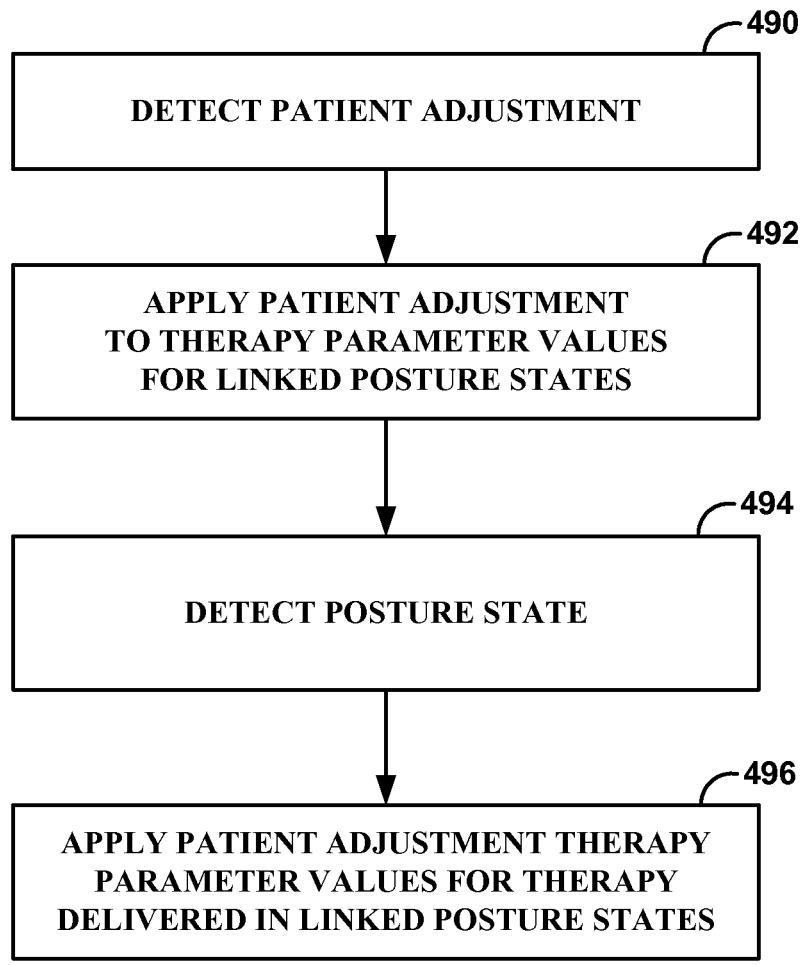

FIGS. 24-26 are flow charts illustrating some of the techniques described in this disclosure. In the example of FIG. 24, a programmer is used to link posture states (450), select link-active group(s) for the linked posture states (452), select therapy parameter values, e.g., for one of the linked posture states (454), and automatically associate the therapy parameter values with each of the linked posture states (456). The IMD may be programmed to apply this linking information. Then, in the course of posture responsive therapy, the IMD may detect posture states (458) and apply common therapy parameter values associated with linked posture states for therapy (such as electrical neurostimulation) delivered to the linked posture states (460).

FIG. 25 illustrates a programmer being configured to specify programming of an IMD such as posture-responsive therapy, i.e., delivery of different therapy with different therapy parameter values based on posture state. One or more therapy parameter values are left undefined for at least some posture states (470). Thereafter, if a programmer or the IMD detects a patient adjustment to therapy parameter values while the patient occupies a posture state for which posture responsive therapy for which therapy parameter values are undefined (472), the IMD or programmer may automatically associate the patient adjusted therapy parameter values with the posture state (474) such that posture responsive therapy according to the patient adjusted therapy parameters values is active for that posture state in the future (476). Then, upon detecting that posture state in the future (478), the IMD may apply therapy according to the therapy parameter values associated with the posture state based on the patient adjustment received when the one or more therapy parameter values were undefined for that posture state (480). Hence, a posture state may be changed from having one or more therapy parameter values undefined to having a complete set of therapy parameter values defined for posture state-responsive therapy.

FIG. 26 illustrates detection of a patient adjustment, while occupying a posture state, to one or more therapy parameter values, such as amplitude, e.g., by a programmer or IMD (490), application of the patient adjustment to adjust therapy parameter values for other posture states that are linked with the posture state (492). When posture states are detected during the course of posture-responsive therapy (494), a programmer or IMD may cause the IMD to deliver therapy that applies the patient adjustment-based therapy parameter values for therapy delivered when the patient is in the linked posture states (496).

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that may benefit from the subject matter of this disclosure.

Many embodiments of the disclosure have been described. Various modifications may be made without departing from the scope of the claims. These and other embodiments are within the scope of the following claims.

The invention claimed is:

1. A system comprising:
a posture state module configured to record a current posture of a patient;
a user interface configured to receive a therapy adjustment to a therapy parameter;
a processor configured to associate a posture that the posture state module recorded when the user interface received the therapy adjustment with the therapy adjustment, determine whether the posture falls within a defined posture state, compare the therapy adjustment to therapy parameter information associated with the defined posture state, and update at least one posture state definition based on the determination and the comparison.

2. The system of claim 1, further comprising a memory configured to store the at least one posture state definition and associated therapy information.

3. The system of claim 2, further comprising an external programmer that comprises at least one of the memory, posture state module, user interface, or processor.

4. The system of claim 3, wherein the external programmer comprises at least one of a patient programmer or a clinician programmer.

5. The system of claim 2, further comprising a medical device that comprises at least one of the memory, posture state module, or processor.

6. The system of claim 5, wherein the medical device comprises an implantable medical device.

7. The system of claim 1, wherein the processor is configured to determine that the posture falls within the posture state and determine whether to at least one of merge the posture state with an adjacent posture state and split the posture state into multiple posture states.

8. The system of claim 7, wherein the processor is configured to determine whether a difference between an adjusted therapy parameter value corresponding to the therapy adjustment and an associated therapy parameter value associated with the posture state is less than a threshold difference.

9. The system of claim 8, wherein, if the difference is greater than the threshold difference, the processor is configured to analyze one or more previous therapy adjustments associated with postures that fall within the posture state and split the posture state into two or more new posture states based on the analysis.

10. The system of claim 8, wherein, if the difference is less than the threshold difference, the processor is configured to determine whether a distance between the posture state and an adjacent posture states is below a threshold distance, determine whether a difference between the adjusted therapy parameter value corresponding to the therapy adjustment and an adjacent therapy parameter value associated with the adjacent posture state is less than the threshold difference, and merge the posture state and adjacent postures state based on the determinations.

11. The system of claim 1, wherein the processor is configured to determine that the posture falls outside of the posture state and determine whether to at least one of expand the posture state to include the posture or create a new posture state that includes the posture.

12. The system of claim 1, further comprising an external programmer that comprises the posture state module, the user interface, and the processor.

13. The system of claim 1, further comprising:
telemetry circuitry configured to receive the therapy adjustment; and
an implantable medical device that comprises the posture state module, the processor, and the telemetry circuitry.

14. The system of claim 1, wherein:
the user interface is configured to receive, as the therapy adjustment, an adjustment from a first value of the therapy parameter to a second value of the therapy parameter; and
the processor is configured to compare the second value of the therapy parameter to a third value of the therapy parameter, the therapy parameter information comprising the third value of the therapy parameter.

15. The system of claim 1, wherein the therapy parameter information has been previously associated with the defined posture state.

16. A system comprising:
means for recording a therapy adjustment to a therapy parameter and a posture of a patient corresponding to the therapy adjustment;
means for determining whether the posture falls within a defined posture state;
means for comparing the therapy adjustment to therapy parameter information associated with the defined posture state; and
means for updating at least one posture state definition based on the determination and the comparison.

17. The system of claim 16, wherein the means for updating the at least one posture state definition comprises means for at least one of merging the posture state with an adjacent posture state or splitting the posture state into multiple posture states if the posture falls within the posture state.

18. The system of claim 17, wherein the means for comparing the therapy adjustment to therapy information associated with the defined posture state comprises means for determining whether a difference between an adjusted therapy parameter value corresponding to the therapy adjustment and an associated therapy parameter value associated with the posture state is less than a threshold difference.

19. The system of claim 18, further comprising means for analyzing, if the difference between an adjusted therapy parameter value corresponding to the therapy adjustment and an associated therapy parameter value associated with the posture state is greater than the threshold difference, one or more previous therapy adjustments associated with postures that fall within the posture state and splitting the posture state into two or more new posture states based on the analysis.

20. The system of claim 18, further comprising:
means for determining, if the difference between an adjusted therapy parameter value corresponding to the therapy adjustment and an associated therapy parameter value associated with the posture state is less than the threshold difference, whether a distance between the posture state and an adjacent posture states is below a threshold distance;

means for determining, if the difference between an adjusted therapy parameter value corresponding to the therapy adjustment and an associated therapy parameter value associated with the posture state is less than the threshold difference, whether a difference between the adjusted therapy parameter value corresponding to the therapy adjustment and an adjacent therapy parameter value associated with the adjacent posture state is less than the threshold difference; and means for merging the posture state and adjacent posture state based on the determinations.

21. The system of claim 16, wherein, if the posture falls outside of the posture state, the means for updating the set of posture state definitions comprises means for at least one of expanding the posture state to include the posture or creating a new posture state that includes the posture.

22. The system of claim 16, further comprising means for associating the therapy adjustment with a posture of the at least one updated posture state definition.

23. The system of claim 16, further comprising an implantable medical device comprising the means for recording the therapy adjustment and the posture of a patient corresponding to the therapy adjustment, the means for determining whether the posture falls within the defined posture state, the means for comparing the therapy adjustment to therapy parameter information associated with the defined posture state, and the means for updating the at least one posture state definition based on the determination and the comparison.

24. The system of claim 23, further comprising an external programmer comprising means for receiving the therapy adjustment from the patient.

25. The system of claim 16, further comprising an external programmer comprising the means for recording the therapy adjustment and the posture of a patient corresponding to the therapy adjustment, the means for determining whether the posture falls within the defined posture state, the means for comparing the therapy adjustment to therapy parameter information associated with the defined posture state, and the means for updating the at least one posture state definition based on the determination and the comparison.

26. A device comprising:
a posture state module configured to record a current posture of a patient; and
a processor configured to receive a therapy adjustment to a therapy parameter, associate a posture that the posture state module recorded when the processor received the therapy adjustment with the therapy adjustment, determine whether the posture falls within a defined posture state, compare the therapy adjustment to therapy parameter information associated with the defined posture state, and update at least one posture state definition based on the determination and the comparison.

27. The device of claim 26, wherein the device is an implantable medical device configured to be implanted within the patient.

28. An external programmer comprising:
a user interface configured to receive a therapy adjustment to a therapy parameter; and
a processor configured to record a current posture of a patient, associate the posture that the processor recorded when the user interface received the therapy adjustment with the therapy adjustment, determine whether the posture falls within a defined posture state, compare the therapy adjustment to therapy parameter information associated with the defined posture state, and update at least one posture state definition based on the determination and the comparison.

* * * * *